US007384642B2

(12) United States Patent
Minke et al.

(10) Patent No.: US 7,384,642 B2
(45) Date of Patent: Jun. 10, 2008

(54) CANINE INFLUENZA VACCINES

(75) Inventors: Jules Maarten Minke, Corbas (FR); Kemal Karaca, Athens, GA (US); Jiansheng Yao, North York (CA)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/211,983

(22) Filed: Aug. 25, 2005

(65) Prior Publication Data

US 2007/0048819 A1 Mar. 1, 2007

(51) Int. Cl.

*A61K 39/145* (2006.01)
*A61K 39/00* (2006.01)
*A61K 39/285* (2006.01)

(52) U.S. Cl. .............................. 424/210.1; 424/133.1; 424/134.1; 424/206.1; 424/209.1; 424/132.1

(58) Field of Classification Search .................... None
See application file for complete search history.

(56) References Cited

OTHER PUBLICATIONS

Enzo Paoletti, Applications of pox virus vectors to vaccination: An update, Proceedings of the National Academy of Sciences of the United States of America, Oct. 1996, vol. 93, pp. 11349-11353.*
Youngner et al., Derivation and characterization of a live attenuated equine influenza vaccine virus, American Journal of Veterinary Research, Aug. 2001, vol. 62, No. 8, pp. 1290-1294.*
Daly et al., Current perspectives on control of equine influenza, Veterinary Research, 2004, vol. 35, pp. 411-423.*
Karaca et al., Recombinatn canarypox vectored West Nile virus (WNV) vaccine protects dogs and cats against a mosquito WNV challenge, Vaccine, Mar. 2005, vol. 23, pp. 3808-3813.*
Sarah Carey, UF Researchers: Equine Influenza Virus Involved In Recent Respiratory Disease Outbreak In Racing Greyhounds, University of Florida News, Apr. 22, 2004.*
Appel et al. Immune response to vaccinia virus and recombinant virus products in dogs. American Journal of Veterinary Research, Nov. 1988, vol. 49, No. 11, pp. 1932-1934.*
Science Daily, University of Florida news release, Apr. 29, 2004, 2 pages.*
Cornell Veterinary Magazine, [Online] 2004, pp. 10-13, Retrieved from the Internet: URL:http://www.vet.cornell.edu/news/cvmagazine/Fall04/detectives.pdf> See p. 11, last sentence of first (incomplete) paragraph.
Dubovi EJ, Crawford PC, Donis RO, Castelman WL, Stephenson I, Gibbs EPJ: "Isolation of Equine Influenza Virus from Racing Greyhounds with Fatal Hemorrhagic Pneumonia" Proceedings of the 47th Annual Meeting of American Association of Veterinary Laboratory Diagnosticians, Oct. 2004, p. 158.
Edlund Toulemonde C et al: "Efficacy of a recombinant equine influenza vaccine against challenge with an American lineage H3N8 influenza virus responsible for the 2003 outbreak in the United Kingdom." The Veterinary Record Mar. 19, 2005, vol. 156, No. 12, Mar. 19, 2005, pages 367-371.
Stephensen CB et al.: "Canine Distemper Virus (CDV) infection of ferrets as a model for testing Morbillivirus strategies: NYVAC- and ALVAC-based CDV recombinants protect against symptomatic infection" Journal of Virology, The American Society for Microbiology, US, vol. 71, No. 2, Feb. 1997, pp. 1506-1513.
Wood J Met Al: "The standardization of inactivated equine influenza vaccines by single-radial immunodiffusion" Journal of Biological Standardization, Academic Press, London, GB, vol. 11, No. 2, Apr. 1983, pp. 133-136.

* cited by examiner

*Primary Examiner*—Bruce R. Campell
*Assistant Examiner*—Sharon Hurt
(74) *Attorney, Agent, or Firm*—Judy Jarecki-Black; Merial Limited; Thomas Kowalski

(57) ABSTRACT

The present invention encompasses influenza vaccines, in particular canine influenza vaccines. The vaccine may be a recombinant poxvirus vaccine or an inactivated vaccine. The invention also encompasses recombinant poxvirus vectors encoding and expressing influenza antigens, epitopes or immunogens which can be used to protect animals, in particular dogs, against influenza.

16 Claims, 14 Drawing Sheets

FIGURE 1

GTATTCTAAACTAGGAATAGATGAAATTATGTGCAAAGGAGATACCTTTAGATATGGATCTGATTTAT
TTGGTTTTTCATAATCATAATCTAACAACATTTTCACTATACTATACCTTCTTGCACAAGTCGCCATTA
GTAGTATAGACTTATACTTTGTAACCATAGTATACTTTAGCGCGTCATCTTCTTCATCTAAAACAGATT
TACAACAATAATCATCGTCGTCATCTTCATCTTCATTAAAGTTTTCATATTCAATAACTTTCTTTTCTAA
AACATCATCTGAATCAATAAACATAGAACGGTATAGAGCGTTAATCTCCATTGTAAAATATACTAACG
CGTTGCTCATGATGTACTTTTTTTTCATTATTTAGAAATTATGCATTTTAGATCTTTATAAGCGGCCGT
GATTAACTAGTCATAAAAACCCGGGATCGATTCTAGACTCGAGCGGCCGCCAGTGTGATGGATATCT
GCAGAATTCGGCTTTGGTCCTTACTCAAATGCAAATGTTGCACCTGATGTTGCCTTTTTGGCAAGCCC
ACATAATGAAACCCAATAGAACAACGCAAATTAAGAAGCATGATATGGCGAATGAAATCCACAGTAT
CCAATCTTTGTAGCCTGATTTCAACTCAACACTTTTGATTTGAAATCGGTTGTTTAATGCTTCATCTCT
GTATATGTAATGGTCATATGTCCCATTTCTTATTGATCCAATGCATGCATTATCACATTTGTGGTAAAT
CTTGAAACATCCACCTCCCATGTCTTCCGCGTTTTCTCTTAACTGGCGCCTAGTCTTCTCGAATAATTT
ATTCATTTCTGCATCTGTTAAGTCAATTGTATGTTGATTTTCTAGAGCCACCAGCAATTCTGCATTGTA
GGACCATAGGTCTATTTTGGTGTCTTCTACATACTTCTCCAAATCCTGGATTCTCCCTTCTACTTCTGA
GAATTCCTTTTCTATTTGATGGAATTTCTCATTGGTCCTTTCAATCACTCTGTTTAATTTTCCATTGATC
TGGTCTATGGCTGCTTGAGTGCTCTTTAGATCTGCAGCTTGTCCTGTTCCTTCCGAGTTTTGATATCG
GAATCCATACCACCCATCAACCATTCCTTCCCAGCCGTTTTCTATGAATCCCGCTATTGCTCCAAAGA
TTCCTCTGATTTGCTTTTCTGGTACATTCCTCATCCCAGTGGCCAGCTTTAAAGTGTTTTGCCTGATAT
ACTTGGGGCATTTTCCATATGTAATTTTGTTCACATTTTGAAATGGTTTGTCGTTGGGGATGCTTCCAT
TTGGTGTAATACATTCAGACACACAAGTGTCTATGAGTGCATCTGATCTCATTACAGAGCTTTTCCCT
GTTCTCAATTTAAAATATCCCCGCGGTGCAACTAAGTTGCCATTACTGTTTATCATTAGAATATCTCCA
GGTTTTACAATGGTCCAGTATATGCTTATCCTGCCTGATTGACCCCTGACCCACGGCCTAGATCCGAT
GTTAGGGATTACTGTTTGTTGACTTCTTTCTGTTGAGACTGTTACTCGTCCTGATTCTTGGATATATAA
TTTTGTCTGCTCTTTGTTTGAGCTCGGGTGATGAATCCCCCAGATGTATAGTTTATCGAAATTTTTATT
GTTAGGCATTGTCACATTCAATATGGGGTAAGAATTTCCAGATTTTGTTAGCCAATTCAGTCGGCTAA
AGAAACTATCGGCTGATCCCCTTTTGCAGGCTCCACTTCTTCCGTTTTGAGTGACACCTGTCCATGTG
AACCCCTCTGCTGTGAATTCTAATGTTCCTGAGGATGCTACAATGGACCGGAGCGATGCATAGTCAG
GGATGTCATATGGGTAGCAATTGCTGAAAGCGCTGCTTCTTTCTATGAAGAGGTCCCAATTCTCATAC
TGAAAATCATCACAATGGGGGTCTCCTAGCATTGCATCTATTAATGTGCAATTTCTTCCATCTAGAAC
CCTATATGAGTTGTTGCATATTTTCCCTATTGAAATGCTCTGGACTAATTCAGTAGCATTTGTCACCTC
AATTTGGTCATCAGTTATTGTTTTTACCAATGTTCCATTTGCTACTGCATGGTGTCCCAGACATAATGT
GGCTGTGTTGTTGCCACTGGTTGGGTTTTGACTGTAGACCCAATGGGTCAGTAGTATCAAAATAATG
GTTGTCTTCATTACGATACAAACTTAACGGATATCGCGATAATGAAATAATTTATGATTATTTCTCGCT
TTCAATTTAACACAACCCTCAAGAACCTTTGTATTTATTTTCACTTTTTAAGTATAGAATAAAGAAGCT
CTAATTAATTAACGAGCAGATAGTCTCGTTCTCGCCCTGCCTGATGACTAATTAATTAACCCGGATCC
TTTTTATAGCTAATTAGTCACGTACCTTTGAGAGTACCACTTCAGCTACCTCTTTTGTGTCTCAGAGTA
ACTTTCTTTAATCAATTCCAAAACAGTATATGATTTTCCATTTCTTTCAAAGATGTAGTTTACATCTGCT
CCTTTGTTGAAAAGTAGCCTGAGCACTTCTTTTCTACCATGAATTACAGCTGGCAAGATCAATTTTTCC
CAGTTCTGGACATTTTATTTTTTTTAAGTAGTGTGCTACATATTTCAATATTTCCAGATTGTACAGCGA
TCATTAAAGGAGTACGTCCCATGTTATCCAGCAAGTCAGTATCAGCACCTTTGTTCAATAGAAGTTTA
ACCATTGTTAAATTTTTATTTGATACGGCTATATGTAGAGGAGTTAACCGATCCGTGTTTGAAATATCT
ACATCCGCCGAATGAGCCAATAGAAGTTTAACCAAATTAACTTTGTTAAGGTAAGCTGCCAAACACAA
AGGAGTAAAGCCTCCGCTGTAAAGAACATTGTTTACATAGTTATTCTTCAACAGATCTTTCACTATTTT
GTAGTCGTCTCTCAACACCGCATCATGCAGACAAGAAGTTGTGCATTCAGTAACTACAGGTTTAGCT
CCATACCTCATCAAGATTTTTATAGCCTCGGTATTCTTGAACATTACAGCCATTTCAAGAGGAGATTG
TAGAGTACCATATTCCGTGTTAGGGTCGAATCCATTGTCCAAAAACCTATTTAGAGATGCATTGTCAT
TATCCATGATAGCCTCACAGACGTATATGTAAGCCATCTTGAATGTATAATTTTGTTGTTTTCAACAAC
CGCTCGTGAACAGCTTCTATACTTTTTCATTTTCTTCATGATTAATATAGTTTACGGAATATAAGTATA
CAAAAAGTTTATAGTAATCTCATAATATCTGAAACACATACATAAAACATGGAAGAATTACACGATGT
CGTTGAGATAAATGGCTTTTTATTGTCATAGTTTACAAATTCGCAGTAATCTTCATCTTTTACGAATAT

Continuation of FIGURE 1

TGCAGAATCTGTTTTATCCAACCAGTGATTTTTGTATAATATAACTGGTATCCTATCTTCCGATAGAAT
GCTGTTATTTAACATTTTTGCACCTATTAAGTTACATCTGTCAAATCCATCTTTCCAACTGACTTTATGT
AACGATGCGAAATAGCATTTATCACTATGTCGTACCCAATTATCATGACAAGATTCTCTTAAATACGTA
ATCTTATTATCTCTTGCATATTCGTAATAGTAATTGTAAAGAGTATACGATAACAGTATAGATATACAC
GTGATATAAATATTTAACCCCATTCCTGAGTAAAATAATTACGATATTACATTTCCTTTTATTATTTTTA
TGTTTTAGTTATTTGTTAGGTTATACAAAAATTATGTTTATTTGTGTATATTTAAAGCGTCGTTAAGAAT
AAGCTTAGTTAACATATTATCGCTTAGGTTTTGTAGTATTTGAATCCTTTCTTTAAATGGATTATTTTTC
CAATGCATATTTATAGCTTCATCCAAAGTATAACATTTAACATTCA (SEQ ID NO: 1)

FIGURE 2

GTATTCTAAACTAGGAATAGATGAAATTATGTGCAAAGGAGATACCTTTAGATATGGATCTGATTTATTTGGTTTTT
CATAATCATAATCTAACAACATTTTCACTATACTATACCTTCTTGCACAAGTCGGCATTAGTAGTATAGACTTATAC
TTTGTAACCATAGTATACTTTAGCGCGTCATCTTCTTCATCTAAAACAGATTTACAACAATAATCATCGTCGTCATC
TTCATCTTCATTAAAGTTTTCATATTCAATAACTTTCTTTTCTAAAACATCATCTGAATCAATAAACATAGAACGGT
ATAGAGCGTTAATCTCCATTGTAAAATATACTAACGGGTTGCTCATGATGTACTTTTTTTTTCATTATTTAGAAATTA
TGCATTTTAGATCTTTATAAGCGGCCGTGATTAACTAGTCATAAAAACCCGGGATCGATTCTAGACTCGAGGGTACC
TCAAATGCAAATGTTGCATCTGATGTTGCCTTTTTGGCAAGCCCACATAATGAAACCCAATAGAACAACGCAAATTA
AGAAGCATGATATGGCGAATGAAATCCACAGTATCCAATCTTTGTAGCCTGATTTCAACTCAACACCTTTGATTTGA
AATCGGTTGTTTAATGCTTCATCTCTGTATATGTAATGGTCATATGTCCCATTTCTTATTGATCCAATGCATGCATT
ATCACATTTGTGGTAAATCTTGAAACATCCACCTCCCATGTCTTCCGCGTTTTCTCTTAACTGGCGTCTAGTCTTCT
CGAATAATTTATTCATTTCTGCATCTGTTAAGTCAATTGTATGTTGATTTTCTAGAGCCACCAGCAATTCTGCATTG
TAGGACCATAGGTCTATTTTGGTGTCTTCTACATACTTCTCCAAGTCCTGGATTCTCCCTTCTACTTCTGAGAATTC
CTTCTCTATTTGATGGAATTTCTCATTGGTCCTTTCAATCACTCTGTTTAATTTTCCATTAATCTGGTCGATGGCTG
CTTGAGTGCTCTTTAGATCTGCAGCTTGTCCTGTTCCTTCCGAGTTTTGATATCGGAATCCATACCACCCATCAACC
ATTCCTTCCCAGCCGTTTTCTATGAATCCCGCTATTGCTCCAAAGATTCCTCTGATTTGCTTTTCTGGTACATTCCT
CATCCCAGTGGCCAGCTTTAAAGTGTTTTGCCTGATATACTTGGGGCATTTTCCATATGTAACTTTGTTCACATTTT
GAAATGGTTTGTCGTTGGGGATGCTTCCATTTGGTGTAATACATTCAGACACACAAATGTCTATGGGTGCATCTGAT
CTCATTACAGAGCTTTTCCCTGTTTTCAATTTAAAATATCCCCGCGGTGCAACTAAGTTGCCATTACTGTTTATCAT
TAGGATATCTCCAGGTTTTACAATGGTCCAGTATATGCTTATCCTGCCTGATTGACCCCTGACCCACGGTCTAGATC
CGATATTAGGGATTATCGTTTGTTGACTTCTTTTTGTTGAGACTGTTACTCGTCCTGATTCTTGGATGTACAATTCT
GTTTGCTGTTGGTTTGAGCTCGGGTGATGAATCCCCCAGATGTATAGTTTGTCGAAATTTTTATTGTTAGGCATTGT
CACATTCAATGTGGGGTAAGAGTTTCCAGATTTTGTTAGCCAATTCAGTCGGCTAAAGAAACTATCGGCTGATCCCC
TTTTGCAGGCTCCACTTCTTCCGTTTTGAGTGACACCTGTCCATGTGAATCCCTCTGCTGTGAATTCCAATGTTCCT
GAGGATGCTACAATGGACCGGAGCGATGCATAGTCAGGGATGTCATATGGGTAGCAATTGCTGAAAGCGCTGCTTCT
TTCTATGAAGAGGTCCCAATTCTCATACTGAAAGACATCACAGTGGGGGTCTCCTAGCATTGCATCTATTAATGTGC
AATTTCTTCCATCTAGAACTCTATATGAGTTGTTGCATATTTTCCCTATTGAAATGCTCTGAACTAATTCAGTAGCA
TTTGTCACCTCAATTTGGTCATCAGTTATTGTTTTTACCAATGTTCCATTTGCTACTGCATGGTGTCCCAGACATAA
TGTGGCTGTGTTGTTGCCACTGGTTGGGTTTTGACTGTAGACCCAATGGGTCAGTAGTATCAAAATAATGGTTGTCT
TCATTACGATACAAACTTAACGGATATCGCGATAATGAAATAATTTATGATTATTTCTCGCTTTCAATTTAACACAA
CCCTCAAGAACCTTTGTATTTATTTTCACTTTTTAAGTATAGAATAAAGAAGCTCTAATTAATTAACGAGCAGATAG
TCTCGTTCTCGCCCTGCCTGATGACTAATTAATTAACCCGGATCCTTTTTATAGCTAATTAGTCACGTACCTTTGAG
AGTACCACTTCAGCTACCTCTTTTGTGTCTCAGAGTAACTTTCTTTAATCAATTCCAAAACAGTATATGATTTTCCA
TTTCTTTCAAAGATGTAGTTTACATCTGCTCCTTTGTTGAAAAGTAGCCTGAGCACTTCTTTTCTACCATGAATTAC
AGCTGGCAAGATCAATTTTTCCCAGTTCTGGACATTTTATTTTTTTTAAGTAGTGTGCTACATATTTCAATATTTCC
AGATTGTACAGCGATCATTAAAGGAGTACGTCCCATGTTATCCAGCAAGTCAGTATCAGCACCTTTGTTCAATAGAA
GTTTAACCATTGTTAAATTTTTATTTGATACGGCTATATGTAGAGGAGTTAACCGATCCGTGTTTGAAATATCTACA
TCCGCCGAATGAGCCAATAGAAGTTTAACCAAATTAACTTTGTTAAGGTAAGCTGCCAAACACAAAGGAGTAAAGCC
TCCGCTGTAAAGAACATTGTTTACATAGTTATTCTTCAACAGATCTTTCACTATTTTGTAGTCGTCTCTCAACACCG
CATCATGCAGACAAGAAGTTGTGCATTCAGTAACTACAGGTTTAGCTCCATACCTCATCAAGATTTTTATAGCCTCG
GTATTCTTGAACATTACAGCCATTTCAAGAGGAGATTGTAGAGTACCATATTCCGTGTTAGGGTCGAATCCATTGTC
CAAAAACCTATTTAGAGATGCATTGTCATTATCCATGATAGCCTCACAGACGTATATGTAAGCCATCTTGAATGTAT
AATTTTGTTGTTTTCAACAACCGCTCGTGAACAGCTTCTATACTTTTTCATTTTCTTCATGATTAATATAGTTTACG
GAATATAAGTATACAAAAAGTTTATAGTAATCTCATAATATCTGAAACACATACATAAAACATGGAAGAATTACACG
ATGTCGTTGAGATAAATGGCTTTTTATTGTCATAGTTTACAAATTCGCAGTAATCTTCATCTTTTACGAATATTGCA
GAATCTGTTTTATCCAACCAGTGATTTTTGTATAATATAACTGGTATCCTATCTTCCGATAGAATGCTGTTATTTAA
CATTTTTGCACCTATTAAGTTACATCTGTCAAATCCATCTTTCCAACTGACTTTATGTAACGATGCGAAATAGCATT
TATCACTATGTCGTACCCAATTATCATGACAAGATTCTCTTAAATACGTAATCTTATTATCTCTTGCATATTCGTAA
TAGTAATTGTAAAGAGTATACGATAACAGTATAGATATACACGTGATATAAATATTTAACCCCATTCCTGAGTAAAA
TAATTACGATATTACATTTCCTTTTATTATTTTTATGTTTTAGTTATTTGTTAGGTTATACAAAAATTATGTTTATT
TGTGTATATTTAAAGCGTCGTTAAGAATAAGCTTAGTTAACATATTATCGCTTAGGTTTTGTAGTATTTGAATCCTT
TCTTTAAATGGATTATTTTTCCAATGCATATTTATAGCTTCATCCAAAGTATAACATTTAACATTCA (SEQ ID NO:2)

FIGURE 3

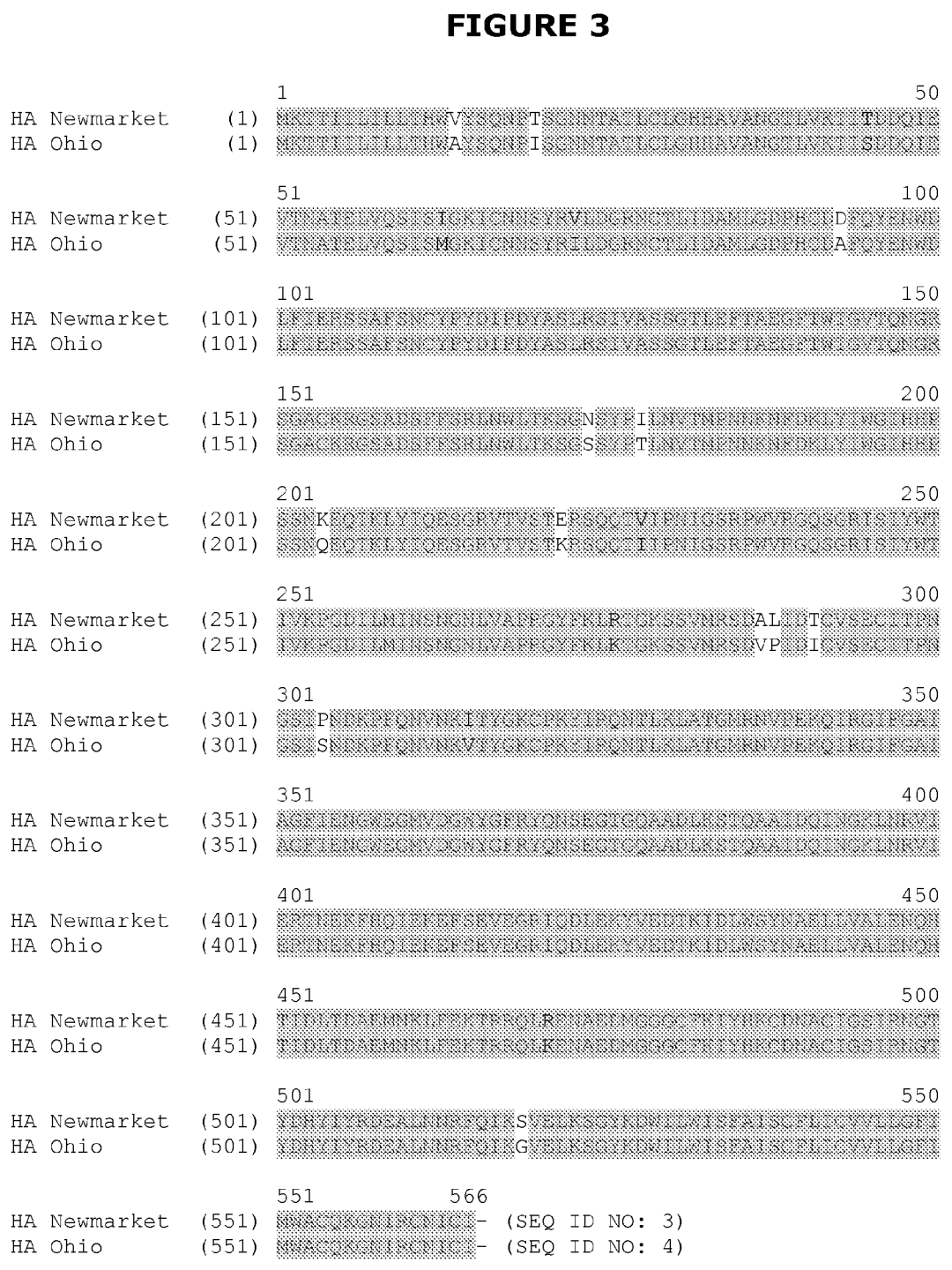

```
                     1                                                50
HA Newmarket   (1)  [illegible]V[illegible]T[illegible]T[illegible]
HA Ohio        (1)  [illegible]A[illegible]I[illegible]S[illegible]

                     51                                              100
HA Newmarket  (51)  [illegible]I[illegible]V[illegible]D[illegible]
HA Ohio       (51)  [illegible]M[illegible]A[illegible]

                     101                                             150
HA Newmarket (101)  [illegible]
HA Ohio      (101)  [illegible]

                     151                                             200
HA Newmarket (151)  [illegible]N[illegible]I[illegible]
HA Ohio      (151)  [illegible]S[illegible]T[illegible]

                     201                                             250
HA Newmarket (201)  [illegible]K[illegible]E[illegible]V[illegible]
HA Ohio      (201)  [illegible]Q[illegible]K[illegible]

                     251                                             300
HA Newmarket (251)  [illegible]R[illegible]AL[illegible]T[illegible]
HA Ohio      (251)  [illegible]K[illegible]VP[illegible]I[illegible]

                     301                                             350
HA Newmarket (301)  [illegible]P[illegible]I[illegible]
HA Ohio      (301)  [illegible]S[illegible]

                     351                                             400
HA Newmarket (351)  [illegible]
HA Ohio      (351)  [illegible]

                     401                                             450
HA Newmarket (401)  [illegible]
HA Ohio      (401)  [illegible]

                     451                                             500
HA Newmarket (451)  [illegible]R[illegible]
HA Ohio      (451)  [illegible]K[illegible]

                     501                                             550
HA Newmarket (501)  [illegible]S[illegible]
HA Ohio      (501)  [illegible]G[illegible]

                     551            566
HA Newmarket (551)  [illegible]- (SEQ ID NO: 3)
HA Ohio      (551)  [illegible]- (SEQ ID NO: 4)
```

Isolate the synthetic EIV H3 HA from a plasmid, pEIV H3N8 HA by EcoRV/XhoI digestion, ligate to EcoRV/XhoI digested pALVAC C5 donor plasmid Remove the multiple cloning sites consisting of XhoI, Xba I, Cla I and Sma I between the HA ORF and the T5AT sequence by ligation of re-filled XhoI site with Sma I site

FIGURE 5A

```
  1  MKTTIILILL THWAYSQNPI SGNNTATLCL GHHAVANGTL VKTISDDQIE
 51  VTNATELVQS ISMGKICNNS YRILDGRNCT LIDAMLGDPH CDAFQYENWD
101  LFIERSSAFS NCYPYDIPDY ASLRSIVASS GTLEFTAEGF TWTGVTQNGR
151  SGACKRGSAD SFFSRLNWLT KSGSSYPTLN VTMPNNKNFD KLYIWGIHHP
201  SSNQEQTKLY IQESGRVTVS TKRSQQTIIP NIGSRPWVRG QSGRISIYWT
251  IVKPGDILMI NSNGNLVAPR GYFKLKTGKS SVMRSDVPID ICVSECITPN
301  GSISNDKPFQ NVNKVTYGKC PKYIRQNTLK LATGMRNVPE KQIRGIFGAI
351  AGFIENGWEG MVDGWYGFRY QNSEGTGQAA DLKSTQAAID QINGKLNRVI
401  ERTNEKFHQI EKEFSEVEGR IQDLEKYVED TKIDLWSYNA ELLVALENQH
451  TIDLTDAEMN KLFEKTRRQL KENAEDMGGG CFKIYHKCDN ACIGSIRNGT
501  YDHYIYRDEA LNNRFQIKGV ELKSGYKDWI LWISFAISCF LICVVLLGFI
551  MWACQKGNIR CNICI* (SEQ ID NO: 5)
```

FIGURE 5B

```
           M13R                                                C5R
  1   GGAAACAGCT ATGACCATGA TTACGAATTG CGGCCGCAAT TCTGAATGTT
      CCTTTGTCGA TACTGGTACT AATGCTTAAC GCCGGCGTTA AGACTTACAA

 51   AAATGTTATA CTTTGGATGA AGCTATAAAT ATGCATTGGA AAAATAATCC
      TTTACAATAT GAAACCTACT TCGATATTTA TACGTAACCT TTTTATTAGG

101   ATTTAAAGAA AGGATTCAAA TACTACAAAA CCTAAGCGAT AATATGTTAA
      TAAATTTCTT TCCTAAGTTT ATGATGTTTT GGATTCGCTA TTATACAATT

151   CTAAGCTTAT TCTTAACGAC GCTTTAAATA TACACAAATA AACATAATTT
      GATTCGAATA AGAATTGCTG CGAAATTTAT ATGTGTTTAT TTGTATTAAA

201   TTGTATAACC TAACAAATAA CTAAAACATA AAAATAATAA AAGGAAATGT
      AACATATTGG ATTGTTTATT GATTTTGTAT TTTTATTATT TTCCTTTACA

251   AATATCGTAA TTATTTTACT CAGGAATGGG GTTAAATATT TATATCACGT
      TTATAGCATT AATAAAATGA GTCCTTACCC CAATTTATAA ATATAGTGCA

301   GTATATCTAT ACTGTTATCG TATACTCTTT ACAATTACTA TTACGAATAT
      CATATAGATA TGACAATAGC ATATGAGAAA TGTTAATGAT AATGCTTATA
                                                 7927.DC
351   GCAAGAGATA ATAAGATTAC GTATTTAAGA GAATCTTGTC ATGATAATTG
      CGTTCTCTAT TATTCTAATG CATAAATTCT CTTAGAACAG TACTATTAAC
      7927.DC
401   GGTACGACAT AGTGATAAAT GCTATTTCGC ATCGTTACAT AAAGTCAGTT
      CCATGCTGTA TCACTATTTA CGATAAAGCG TAGCAATGTA TTTCAGTCAA

451   GGAAAGATGG ATTTGACAGA TGTAACTTAA TAGGTGCAAA AATGTTAAAT
      CCTTTCTACC TAAACTGTCT ACATTGAATT ATCCACGTTT TTACAATTTA
                 7696.CXL
501   AACAGCATTC TATCGGAAGA TAGGATACCA GTTATATTAT ACAAAAATCA
      TTGTCGTAAG ATAGCCTTCT ATCCTATGGT CAATATAATA TGTTTTTAGT

551   CTGGTTGGAT AAAACAGATT CTGCAATATT CGTAAAAGAT GAAGATTACT
      GACCAACCTA TTTTGTCTAA GACGTTATAA GCATTTTCTA CTTCTAATGA

601   GCGAATTTGT AAACTATGAC AATAAAAAGC CATTTATCTC AACGACATCG
      CGCTTAAACA TTTGATACTG TTATTTTTCG GTAAATAGAG TTGCTGTAGC

651   TGTAATTCTT CCATGTTTTA TGTATGTGTT TCAGATATTA TGAGATTACT
      ACATTAAGAA GGTACAAAAT ACATACACAA AGTCTATAAT ACTCTAATGA

701   ATAAACTTTT TGTATACTTA TATTCCGTAA ACTATATTAA TCATGAAGAA
      TATTTGAAAA ACATATGAAT ATAAGGCATT TGATATAATT AGTACTTCTT
```

Continuation of FIGURE 5B

```
 751  AATGAAAAAG TATAGAAGCT GTTCACGAGC GGTTGTTGAA AACAACAAAA
      TTACTTTTTC ATATCTTCGA CAAGTGCTCG CCAACAACTT TTGTTGTTTT
                           7926.DC
 801  TTATACATTC AAGATGGCTT ACATATACGT CTGTGAGGCT ATCATGGATA
      AATATGTAAG TTCTACCGAA TGTATATGCA GACACTCCGA TAGTACCTAT

 851  ATGACAATGC ATCTCTAAAT AGGTTTTTGG ACAATGGATT CGACCCTAAC
      TACTGTTACG TAGAGATTTA TCCAAAAACC TGTTACCTAA GCTGGGATTG

 901  ACGGAATATG GTACTCTACA ATCTCCTCTT GAAATGGCTG TAATGTTCAA
      TGCCTTATAC CATGAGATGT TAGAGGAGAA CTTTACCGAC ATTACAAGTT

 951  GAATACCGAG GCTATAAAAA TCTTGATGAG GTATGGAGCT AAACCTGTAG
      CTTATGGCTC CGATATTTTT AGAACTACTC CATACCTCGA TTTGGACATC
                      7697.CXL
1001  TTACTGAATG CACAACTTCT TGTCTGCATG ATGCGGTGTT GAGAGACGAC
      AATGACTTAC GTGTTGAAGA ACAGACGTAC TACGCCACAA CTCTCTGCTG

1051  TACAAAATAG TGAAAGATCT GTTGAAGAAT AACTATGTAA ACAATGTTCT
      ATGTTTTATC ACTTTCTAGA CAACTTCTTA TTGATACATT TGTTACAAGA

1101  TTACAGCGGA GGCTTTACTC CTTTGTGTTT GGCAGCTTAC CTTAACAAAG
      AATGTCGCCT CCGAAATGAG GAAACACAAA CCGTCGAATG GAATTGTTTC

1151  TTAATTTGGT TAAACTTCTA TTGGCTCATT CGGCGGATGT AGATATTTCA
      AATTAAACCA ATTTGAAGAT AACCGAGTAA GCCGCCTACA TCTATAAAGT

1201  AACACGGATC GGTTAACTCC TCTACATATA GCCGTATCAA ATAAAAATTT
      TTGTGCCTAG CCAATTGAGG AGATGTATAT CGGCATAGTT TATTTTTAAA
                             7925.DC
1251  AACAATGGTT AAACTTCTAT TGAACAAAGG TGCTGATACT GACTTGCTGG
      TTGTTACCAA TTTGAAGATA ACTTGTTTCC ACGACTATGA CTGAACGACC

1301  ATAACATGGG ACGTACTCCT TTAATGATCG CTGTACAATC TGGAAATATT
      TATTGTACCC TGCATGAGGA AATTACTAGC GACATGTTAG ACCTTTATAA

1351  GAAATATGTA GCACACTACT TAAAAAAAAT AAAATGTCCA GAACTGGGAA
      CTTTATACAT CGTGTGATGA ATTTTTTTTA TTTTACAGGT CTTGACCCTT

1401  AAATTGATCT TGCCAGCTGT AATTCATGGT AGAAAAGAAG TGCTCAGGCT
      TTTAACTAGA ACGGTCGACA TTAAGTACCA TCTTTTCTTC ACGAGTCCGA

1451  ACTTTTCAAC AAAGGAGCAG ATGTAAACTA CATCTTTGAA AGAAATGGAA
      TGAAAAGTTG TTTCCTCGTC TACATTTGAT GTAGAAACTT TCTTTACCTT
                                                 7792.SL
1501  AATCATATAC TGTTTTGGAA TTGATTAAAG AAAGTTACTC TGAGACACAA
      TTAGTATATG ACAAAACCTT AACTAATTTC TTTCAATGAG ACTCTGTGTT
        7792.SL
```

Continuation of FIGURE 5B

```
1551  AAGAGGTAGC TGAAGTGGTA CTCTCAAAGG TACGTGACTA ATTAGCTATA
      TTCTCCATCG ACTTCACCAT GAGAGTTTCC ATGCACTGAT TAATCGATAT

1601  AAAAGGATCC GGGTTAATTA ATTAGTCATC AGGCAGGGCG AGAACGAGAC
      TTTTCCTAGG CCCAATTAAT TAATCAGTAG TCCGTCCCGC TCTTGCTCTG
                                  H6
1651  TATCTGCTCG TTAATTAATT AGAGCTTCTT TATTCTATAC TTAAAAAGTG
      ATAGACGAGC AATTAATTAA TCTCGAAGAA ATAAGATATG AATTTTTCAC

1701  AAAATAAATA CAAAGGTTCT TGAGGGTTGT GTTAAATTGA AAGCGAGAAA
      TTTTATTTAT GTTTCCAAGA ACTCCCAACA CAATTTAACT TTCGCTCTTT
                                                 H3 HA  M ·
1751  TAATCATAAA TTATTTCATT ATCGCGATAT CCGTTAAGTT TGTATCGTAA
      ATTAGTATTT AATAAAGTAA TAGCGCTATA GGCAATTCAA ACATAGCATT
          11670JY
      .. K  T  T   I  I  L   I  L  L  T   H  W  A   Y  S  Q
1801  TGAAAACCAC CATCATCCTG ATCCTGCTGA CCCACTGGGC CTACAGCCAG
      ACTTTTGGTG GTAGTAGGAC TAGGACGACT GGGTGACCCG GATGTCGGTC
          11671JY
       N  P  I  S   G  N  N   T  A  T   L  C  L  G   H  H  A ·
1851  AACCCTATCA GCGGCAACAA CACCGCCACC CTGTGCCTGG GCCACCACGC
      TTGGGATAGT CGCCGTTGTT GTGGCGGTGG GACACGGACC CGGTGGTGCG

      . V  A  N   G  T  L  V   K  T  I   S  D  D   Q  I  E  V ·
1901  CGTGGCCAAC GGCACCCTGG TCAAGACCAT CAGCGACGAC CAGATCGAAG
      GCACCGGTTG CCGTGGGACC AGTTCTGGTA GTCGCTGCTG GTCTAGCTTC

      .. T  N  A   T  E  L   V  Q  S  I   S  M  G   K  I  C
1951  TGACCAACGC CACCGAGCTG GTGCAGAGCA TCAGCATGGG CAAGATCTGC
      ACTGGTTGCG GTGGCTCGAC CACGTCTCGT AGTCGTACCC GTTCTAGACG

       N  N  S  Y   R  I  L   D  G  R   N  C  T  L   I  D  A ·
2001  AACAACAGCT ACCGCATCCT GGACGGCAGA AACTGCACCC TGATCGACGC
      TTGTTGTCGA TGGCGTAGGA CCTGCCGTCT TTGACGTGGG ACTAGCTGCG

      . M  L  G   D  P  H  C   D  A  F   Q  Y  E   N  W  D  L ·
2051  CATGCTGGGC GACCCCCACT GCGACGCCTT CCAGTACGAG AACTGGGACC
      GTACGACCCG CTGGGGGTGA CGCTGCGGAA GGTCATGCTC TTGACCCTGG

      .. F  I  E   R  S  S   A  F  S  N   C  Y  P   Y  D  I
2101  TGTTCATCGA GAGGAGCAGC GCCTTCAGCA ACTGCTACCC CTACGACATC
      ACAAGTAGCT CTCCTCGTCG CGGAAGTCGT TGACGATGGG GATGCTGTAG

       P  D  Y  A   S  L  R   S  I  V   A  S  S  G   T  L  E ·
2151  CCTGACTACG CCAGCCTGAG AAGCATCGTG GCCAGCAGCG GCACCCTGGA
      GGACTGATGC GGTCGGACTC TTCGTAGCAC CGGTCGTCGC CGTGGGACCT
       11672JY
      . F  T  A   E  G  F  T   W  T  G   V  T  Q   N  G  R  S ·
```

Continuation of FIGURE 5B

```
2201  GTTCACCGCC GAGGGCTTCA CCTGGACCGG CGTGACCCAG AACGGCAGAA
      CAAGTGGCGG CTCCCGAAGT GGACCTGGCC GCACTGGGTC TTGCCGTCTT
          11673JY
      ..G  A  C   K  R  G   S  A  D  S   F  F  S   R  L  N
2251  GCGGCGCCTG CAAGAGAGGC AGCGCCGACA GCTTCTTCAG CCGCCTGAAC
      CGCCGCGGAC GTTCTCTCCG TCGCGGCTGT CGAAGAAGTC GGCGGACTTG

       W  L  T  K   S  G  S   S  Y  P   T  L  N  V   T  M  P·
2301  TGGCTGACCA AGAGCGGCAG CAGCTACCCC ACCCTGAACG TGACCATGCC
      ACCGACTGGT TCTCGCCGTC GTCGATGGGG TGGGACTTGC ACTGGTACGG

      .N  N  K   N  F  D  K   L  Y  I   W  G  I   H  H  P  S·
2351  CAACAACAAG AACTTCGACA AGCTGTACAT CTGGGGCATC CACCACCCCA
      GTTGTTGTTC TTGAAGCTGT TCGACATGTA GACCCCGTAG GTGGTGGGGT

      ..S  N  Q   E  Q  T   K  L  Y  I   Q  E  S   G  R  V
2401  GCAGCAACCA GGAGCAGACC AAGCTGTACA TCCAGGAGAG CGGCAGAGTG
      CGTCGTTGGT CCTCGTCTGG TTCGACATGT AGGTCCTCTC GCCGTCTCAC

       T  V  S  T   K  R  S   Q  Q  T   I  I  P  N   I  G  S·
2451  ACCGTGTCCA CCAAGAGAAG CCAGCAGACC ATCATCCCCA ACATCGGCAG
      TGGCACAGGT GGTTCTCTTC GGTCGTCTGG TAGTAGGGGT TGTAGCCGTC

      .R  P  W   V  R  G  Q   S  G  R   I  S  I   Y  W  T  I·
2501  CAGACCTTGG GTGCGCGGCC AGTCCGGCAG GATCAGCATC TACTGGACCA
      GTCTGGAACC CACGCGCCGG TCAGGCCGTC CTAGTCGTAG ATGACCTGGT

      ..V  K  P   G  D  I   L  M  I  N   S  N  G   N  L  V
2551  TCGTGAAGCC TGGCGACATC CTGATGATCA ACAGCAACGG CAACCTGGTG
      AGCACTTCGG ACCGCTGTAG GACTACTAGT TGTCGTTGCC GTTGGACCAC
          11674JY
       A  P  R  G   Y  F  K   L  K  T   G  K  S  S   V  M  R·
2601  GCCCCCAGAG GCTACTTCAA GCTGAAAACC GGCAAGAGCA GCGTGATGAG
      CGGGGGTCTC CGATGAAGTT CGACTTTTGG CCGTTCTCGT CGCACTACTC
          11675JY
      .S  D  V   P  I  D  I   C  V  S   E  C  I   T  P  N  G·
2651  AAGCGACGTG CCCATCGACA TCTGCGTGTC CGAGTGCATC ACCCCTAACG
      TTCGCTGCAC GGGTAGCTGT AGACGCACAG GCTCACGTAG TGGGGATTGC

      ..S  I  S   N  D  K   P  F  Q  N   V  N  K   V  T  Y
2701  GCAGCATCAG CAACGACAAG CCCTTCCAGA ACGTGAACAA AGTGACCTAC
      CGTCGTAGTC GTTGCTGTTC GGGAAGGTCT TGCACTTGTT TCACTGGATG

       G  K  C  P   K  Y  I   R  Q  N   T  L  K  L   A  T  G·
2751  GGCAAGTGCC CCAAGTACAT CCGCCAGAAC ACCCTGAAGC TGGCCACCGG
      CCGTTCACGG GGTTCATGTA GGCGGTCTTG TGGGACTTCG ACCGGTGGCC

      .M  R  N   V  P  E  K   Q  I  R   G  I  F   G  A  I  A·
```

Continuation of FIGURE 5B

2801 CATGAGAAAC GTGCCCGAGA AGCAGATCAG AGGCATCTTC GGCGCCATCG
GTACTCTTTG CACGGGCTCT TCGTCTAGTC TCCGTAGAAG CCGCGGTAGC

..G F I E N G W E G M V D G W Y G
2851 CCGGCTTCAT CGAGAACGGC TGGGAGGGCA TGGTGGACGG CTGGTACGGC
GGCCGAAGTA GCTCTTGCCG ACCCTCCCGT ACCACCTGCC GACCATGCCG

F R Y Q N S E G T G Q A A D L K S·
2901 TTCAGATACC AGAACAGCGA GGGCACCGGC CAGGCCGCCG ACCTGAAGAG
AAGTCTATGG TCTTGTCGCT CCCGTGGCCG GTCCGGCGGC TGGACTTCTC

.T Q A A I D Q I N G K L N R V I E·
2951 CACCCAGGCC GCCATCGACC AGATCAACGG CAAGCTGAAC CGCGTGATCG
GTGGGTCCGG CGGTAGCTGG TCTAGTTGCC GTTCGACTTG GCGCACTAGC
11676JY

..R T N E K F H Q I E K E F S E V
3001 AGCGCACCAA CGAGAAGTTC CACCAGATCG AGAAGGAGTT CAGCGAAGTG
TCGCGTGGTT GCTCTTCAAG GTGGTCTAGC TCTTCCTCAA GTCGCTTCAC
11677JY

E G R I Q D L E K Y V E D T K I D·
3051 GAGGGCAGAA TCCAGGACCT GGAGAAGTAC GTGGAGGACA CCAAGATCGA
CTCCCGTCTT AGGTCCTGGA CCTCTTCATG CACCTCCTGT GGTTCTAGCT

.L W S Y N A E L L V A L E N Q H T·
3101 CCTGTGGAGC TACAACGCCG AGCTGCTGGT CGCCCTGGAG AACCAGCACA
GGACACCTCG ATGTTGCGGC TCGACGACCA GCGGGACCTC TTGGTCGTGT

..I D L T D A E M N K L F E K T R
3151 CCATCGACCT GACCGACGCC GAGATGAACA AGCTGTTCGA AAAGACCAGG
GGTAGCTGGA CTGGCTGCGG CTCTACTTGT TCGACAAGCT TTTCTGGTCC

R Q L K E N A E D M G G G C F K I·
3201 CGCCAGCTGA AGGAAAACGC CGAGGACATG GGCGGCGGCT GCTTCAAGAT
GCGGTCGACT TCCTTTTGCG GCTCCTGTAC CCGCCGCCGA CGAAGTTCTA

.Y H K C D N A C I G S I R N G T Y·
3251 CTACCACAAG TGCGACAACG CCTGCATCGG CTCCATCAGG AACGGCACCT
GATGGTGTTC ACGCTGTTGC GGACGTAGCC GAGGTAGTCC TTGCCGTGGA

..D H Y I Y R D E A L N N R F Q I
3301 ACGACCACTA CATCTACAGG GACGAGGCCC TGAACAACCG CTTCCAGATC
TGCTGGTGAT GTAGATGTCC CTGCTCCGGG ACTTGTTGGC GAAGGTCTAG

K G V E L K S G Y K D W I L W I S·
3351 AAGGGCGTGG AGCTGAAGAG CGGCTACAAG GACTGGATCC TGTGGATCAG
TTCCCGCACC TCGACTTCTC GCCGATGTTC CTGACCTAGG ACACCTAGTC

.F A I S C F L I C V V L L G F I M·

Continuation of FIGURE 5B

```
3401   CTTCGCCATC AGCTGCTTCC TGATCTGCGT GGTGCTGCTG GGCTTCATCA
       GAAGCGGTAG TCGACGAAGG ACTAGACGCA CCACGACGAC CCGAAGTAGT
                                  11678JY
       .. W  A  C   Q  K  G   N  I  R  C   N  I  C   I(SEQ ID NO: 5)
3451   TGTGGGCCTG CCAGAAGGGC AACATCCGCT GCAACATCTG CATCTGATGA
       ACACCCGGAC GGTCTTCCCG TTGTAGGCGA CGTTGTAGAC GTAGACTACT
                                  11679JY   C5L
3501   CTCGAGGGTT TTTATGACTA GTTAATCACG GCCGCTTATA AAGATCTAAA
       GAGCTCCCAA AAATACTGAT CAATTAGTGC CGGCGAATAT TTCTAGATTT
                                               7928.DC
3551   ATGCATAATT TCTAAATAAT GAAAAAAAGT ACATCATGAG CAACGCGTTA
       TACGTATTAA AGATTTATTA CTTTTTTTCA TGTAGTACTC GTTGCGCAAT

3601   GTATATTTTA CAATGGAGAT TAACGCTCTA TACCGTTCTA TGTTTATTGA
       CATATAAAAT GTTACCTCTA ATTGCGAGAT ATGGCAAGAT ACAAATAACT
                                7793.SL
3651   TTCAGATGAT GTTTTAGAAA AGAAAGTTAT TGAATATGAA AACTTTAATG
       AAGTCTACTA CAAAATCTTT TCTTTCAATA ACTTATACTT TTGAAATTAC

3701   AAGATGAAGA TGACGACGAT GATTATTGTT GTAAATCTGT TTTAGATGAA
       TTCTACTTCT ACTGCTGCTA CTAATAACAA CATTTAGACA AAATCTACTT

3751   GAAGATGACG CGCTAAAGTA TACTATGGTT ACAAAGTATA AGTCTATACT
       CTTCTACTGC GCGATTTCAT ATGATACCAA TGTTTCATAT TCAGATATGA

3801   ACTAATGGCG ACTTGTGCAA GAAGGTATAG TATAGTGAAA ATGTTGTTAG
       TGATTACCGC TGAACACGTT CTTCCATATC ATATCACTTT TACAACAATC

3851   ATTATGATTA TGAAAAACCA AATAAATCAG ATCCATATCT AAAGGTATCT
       TAATACTAAT ACTTTTTGGT TTATTTAGTC TAGGTATAGA TTTCCATAGA

3901   CCTTTGCACA TAATTTCATC TATTCCTAGT TTAGAATACC TGCAGCCAAG
       GGAAACGTGT ATTAAAGTAG ATAAGGATCA AATCTTATGG ACGTCGGTTC

3951   CTTGGCACTG GCCGTCGTTT TAC (SEQ ID NO: 6)
       GAACCGTGAC CGGCAGCAAA ATG (SEQ ID NO: 7)
                 M13F
```

CANINE INFLUENZA VACCINES

INCORPORATION BY REFERENCE

All documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention encompasses influenza vaccines, in particular canine influenza vaccines. The vaccine may be a recombinant poxvirus vaccine or an inactivated vaccine.

BACKGROUND OF THE INVENTION

Respiratory diseases resembling influenza has infected thousands of dogs in the U.S. Recurrent outbreaks of severe respiratory disease characterized by coughing and fever have occurred in greyhounds at racing kennels. Pathological findings included severe pulmonary and plural hemorrhage, accurate to subacute erosive to hyperplastic tracheitis, bronchitis and bronchiolitis and bronchopneumonia. In 2004, eight greyhounds in Jacksonville, Fla. were killed by an equine influenza virus that jumped the species barrier from horses to dogs.

Equine influenza is a disease of horses, and the virus is in the same group of viruses that cause flu in people. The disease is present in horse populations throughout Europe, North America and parts of Asia, with horses typically developing a fever and a dry hacking cough. In the early stages of the disease, horses are reluctant to eat or drink for several days, but usually recover in two to three weeks.

H3N8 subtypes of equine influenza were previously isolated from lungs of two dogs from Florida and one dog from Texas who had died from the infection. Genetic sequence analyses and phylogenetic comparisons determined that all three canine isolates were closely related and evolved from contemporary strains of equine influenza H3N8. Immunohistochemistry demonstrated influenza antigen in bronchial gland epithelial cells, bronchial and bronchiolar epithelial cells and in alveolar macrophages. Seroconversion to canine influenza virus was demonstrated by hemagglutination inhibition and microneutralization assays.

In 2005, a mutated form of the Bird Flu (H3N8 Virus) was reported to have killed greyhounds in Massachusetts.

Accordingly, there is a need for an effective vaccine against influenza in canines.

Citation or identification of any document in this application is not an admission that such document is available as prior art to the present invention.

SUMMARY OF THE INVENTION

The present invention encompasses canine influenza vaccines, which may be a recombinant canine influenza vaccine or an inactivated canine influenza vaccine.

In an embodiment wherein the canine influenza vaccine is a recombinant vaccine, advantageously, the vector is an avipox expression vector which may comprise a polynucleotide encoding an influenza antigen, epitope or immunogen.

The influenza antigen, epitope or immunogen, be a a hemagglutinin, matrix protein, neuraminidase, nonstructural protein, nucleoprotein, polymerase or any fragment thereof.

In an advantageous embodiment, the canine influenza antigen, epitope or immunogen is derived from a canine infected with influenza. For example, but not by limitation, influenza virus may be isolated from the broncho alveolar lavage and/or lung tissues of an affected dog. Isolation and characterization of the nucleotide sequence of the influenza infecting the dog may be done by routine experimentation by a person of ordinary skill in the art.

The canine influenza antigen, epitope or immunogen may be isolated from an equine influenza. The equine influenza may be an Ohio equine influenza, Kentucky equine influenza or a Newmarket equine influenza.

The avipox expression vector may be an attenuated avipox expression vector. In one embodiment, the avipox expression vector may be a canarypox vector, advantageously ALVAC. The influenza antigen, epitope or immunogen may be a hemagglutinin, such as H3. The canarypox vector may be CP 2242, CP1529 or CP1533.

The present invention also encompasses an inactivated influenza vaccine. The inactivated influenza vaccine may be an inactivated canine influenza. In another embodiment, the inactivated influenza vaccine may be an equine influenza, advantageously an Ohio equine influenza, Kentucky equine influenza or a Newmarket equine influenza.

The invention also relates to method of eliciting an immune response against influenza in a canine, which may comprise administering a formulation comprising any one of the above recombinant influenza vaccine or inactivated vaccine and a pharmaceutically or veterinarily acceptable carrier, excipient or vehicle in an effective amount for eliciting an immune response. In an advantageous embodiment, an adjuvant may be added.

The invention further relates to method of inducing an immune response against influenza in a canine, which may comprise administering a formulation comprising any one of the above recombinant influenza vaccine or inactivated vaccine and a pharmaceutically or veterinarily acceptable carrier, excipient or vehicle in an effective amount for inducing an immune response. In an advantageous embodiment, an adjuvant may be added.

The invention further encompasses a kit for performing a method of eliciting or inducing an immune response which may comprise any one of the recombinant influenza vaccines or inactivated vaccines and instructions for performing the method.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 illustrates the sequence of the insert in PJT004 (SEQ ID NO: 1);

FIG. 2 illustrates the sequence of the insert in PJT005 (SEQ ID NO: 2);

FIG. 3 illustrates a comparison of the amino acid sequence of EIV Ohio 03 strain HA to that of New Market strain H3 HA (SEQ ID NOS: 3 and 4);

FIG. 5A illustrates a predicted amino acid sequence of product(s): EIV H3 HA;

FIG. 5B illustrates a nucleotide sequence of arms and insert with translation

DETAILED DESCRIPTION

Figure 4A:
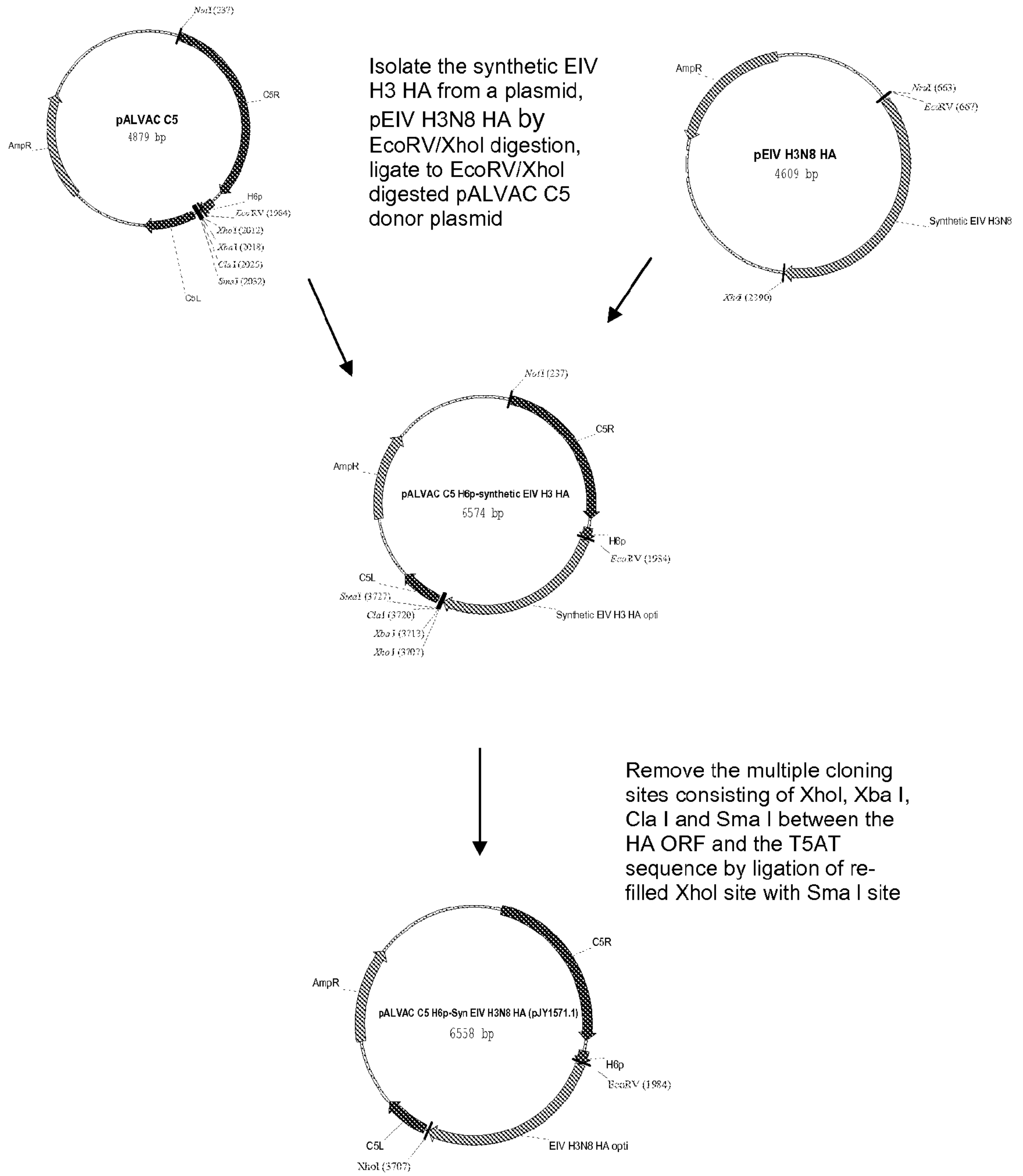
FIG. 4A illustrates a construction of an ALVAC donor plasmid for generation of an ALVAC recombinant expressing codon optimized EIV H3 HA (Ohio 03)

The present invention is based, in part, on Applicants' studies demonstrating a recombinant canarypox expressing equine influenza HA is immunogenic in dogs.

The present invention encompasses any influenza antigen, epitope or immunogen that elicits an immunogenic response in an animal, advantageously a vertebrate, more advantageously a dog. The influenza antigen, epitope or immunogen may be any influenza antigen, epitope or immunogen, such as, but not limited to, a protein, peptide or fragment thereof, that elicits, induces or stimulates a response in an animal, advantageously a vertebrate, more advantageously a dog.

In an advantageous embodiment, the canine influenza antigen, epitope or immunogen is derived from a canine infected with influenza. For example, but not by limitation, influenza virus may be isolated from the broncho alveolar lavage and/or lung tissues of an affected dog. Isolation and characterization of the nucleotide sequence of the influenza infecting the dog may be done by routine experimentation by a person of ordinary skill in the art.

In another advantageous embodiment, the canine influenza, antigen, epitope or immunogen may be derived from an equine infected with influenza or an equine influenza strain. Advantageously, the equine influenza strain is an Ohio equine influenza, Kentucky equine influenza strain or a Newmarket equine influenza strain. The canine influenza antigen, epitope or immunogen may be determined by one of ordinary skill of the art from the nucleotide sequences of Examples 4 and 5. Advantageously, the canine influenza antigen, epitope or immunogen is a hemagglutinin (HA) (e.g., HA precursor, H1, H2, protein, matrix protein (e.g., matrix protein M1 or M2), neuraminidase, nonstructural (NS) protein (e.g., NS1 or NS2), nucleoprotein (NP) and polymerase (e.g., PA polymerase, PB1 polymerase 1 or PB2 polymerase 2).

Examples of Kentucky equine influenza strains that may be used in methods of the present invention include, but are not limited to, equine influenza strains A/eq/Kentucky/98 (see, e.g., Crouch et al., Vaccine. 2004 Dec. 2; 23(3):418-25), A/Equi 2 (Kentucky 81) (see, e.g., Short et al., J Vet Pharmacol Ther. 1986 December; 9(4):426-32, Horner & Ledgard, N Z Vet J. 1988 December; 36(4):205-6), A/equine/Kentucky/1/81 (Eq/Ky) (see, e.g., Breathnach et al., Vet Immunol Immunopathol. 2004 April; 98(3-4):127-36), A/Equine/Kentucky/1/81 (H3N8) (see, e.g., Olsen et al., Vaccine. 1997 July; 15(10):1149-56, Morley et al. Vet Microbiol. 1995 June; 45(1):81-92, Ozaki et al., Vet Microbiol. 2001 September 20; 82(2):111-9, Sugiura et al., J Virol Methods. 2001 October; 98(1):1-8, see, e.g., Sugiura et al., J Virol Methods. 2001 October; 98(1):1-8, Goto et al., J Vet Med Sci. 1993 February; 55(1):33-7, Goto et al., J Vet Med Sci. 1993 February; 55(1):33-7), A/Equine/Kentucky/1/91 (H3N8) (see, e.g., Youngner et al., Am J Vet Res. 2001 August; 62(8):1290-4), A/Equine/Kentucky/1277/90 (Eq/Kentucky) (see, e.g., Webster & Thomas, Vaccine. 1993; 11(10):987-93), A/Equine/Kentucky/2/91 (H3N8) (see, e.g., Donofrio et al., J Vet Diagn Invest. 1994 January; 6(1):39-43), A/Equine/Kentucky/79 (H3N8) (see, e.g., Donofrio et al., J Vet Diagn Invest. 1994 January; 6(1):39-43), A/equine/Kentucky/81 (see, e.g., Sugiura et al., J Virol Methods. 2001 October; 98(1):1-8), A/equine/Kentucky/91 (H3N8) (see, e.g., Gross et al., Equine Vet J. 1998 November; 30(6):489-97), A/equine-2/Kentucky/95 (H3N8) (see, e.g., Heldens et al., Vet J. 2004 March; 167(2):150-7) and A/equine-2/Kentucky/98 (see, e.g., Chambers et al., Equine Vet J. 2001 November; 33(7):630-6), the disclosures of which are incorporated by reference in their entireties.

Examples of Newmarket equine influenza strains that may be used in methods of the present invention include, but are not limited to, equine influenza strains A/eq/Newmarket/1/77 (see, e.g., Lindstrom et al., Arch Virol. 1998; 143(8):1585-98), A/eq/Newmarket/5/03 (see, e.g., Edlund Toulemonde et al., Vet Rec. 2005 March 19; 156(12):367-71), A/Equi 2 (H3N8), Newmarket 1/93 (see, e.g., Mohler et al., Biotechnol Bioeng. 2005 April 5; 90(1):46-58, Nayak et al., J Chromatogr B Analyt Technol Biomed Life Sci. 2005 July 8), A/equi-2/Newmarket-1/93 (see, e.g., Heldens et al., J Immunol Methods. 2002 June 1; 264(1-2):11-7), A/equine/Newmarket/2/93 (see, e.g., Wattrang et al., Viral Immunol. 2003; 16(1):57-67), A/equine/Newmarket/79 (H3N8) (see, e.g., Duhaut & Dimmock, Virology. 2000 September 30; 275(2):278-85, Noble & Dimmock, J Gen Virol. 1994 December; 75 (Pt 12):3485-91, Duhaut & Dimmock, Virology. 1998 September 1; 248(2):241-53, Hannant & Mumford, Vet Immunol Immunopathol. 1989 July; 21(3-4):327-37, Hannant et al., Vet Microbiol. 1989 April; 19(4):293-303, Hannant et al., Vet Rec. 1988 February 6; 122(6):125-8, Richards et al., Vet Immunol Immunopathol. 1992 June; 33(1-2):129-43, Heldens et al., Vet J. 2004 March; 167(2):150-7), A/equine/Newmarket/1/77 (H7N7) (see, e.g., Goto et al., J Vet Med Sci. 1993 February; 55(1):33-7, Sugiura et al., J Virol Methods. 2001 October; 98(1):1-8, Sugiura et al., J Virol Methods. 2001 October; 98(1):1-8) and A/equine-2/Newmarket-2/93 (see, e.g., Heldens et al., Vet J. 2004 March; 167(2):150-7), the disclosures of which are incorporated by reference in their entireties.

The present invention also encompasses other equine influenza viruses, such as, but not limited to, equine influenza virus A/eq/Miami/63 (H3N8) (see, e.g., van Maanen et al., Vet Microbiol. 2003 June 10; 93(4):291-306), A/equi 1 (Prague strain) (see, e.g., Horner & Ledgard, N Z Vet J. 1988 December; 36(4):205-6, Short et al., J Vet Pharmacol Ther. 1986 December; 9(4):426-32), A/Equi 2 (Miami) (see, e.g., Short et al., J Vet Pharmacol Ther. 1986 December; 9(4):426-32), A/equi-1/Prague/56 (Pr/56) (see, e.g., Heldens et al., J Immunol Methods. 2002 June 1; 264(1-2):11-7), A/equi-2/Suffolk/89 (Suf/89) (see, e.g., Heldens et al., J Immunol Methods. 2002 June 1; 264(1-2):11-7), A/Equine 2/Sussex/89 (H3N8) (see, e.g., Mumford et al., Vet Rec. 1994 February 12; 134(7):158-62), A/equine/Sussex/89 (see, e.g., Wattrang et al., Viral Immunol. 2003; 16(1):57-67), A/equine-2/Saskatoon/90 (see, e.g., Chambers et al., Equine Vet J. 2001 November; 33(7):630-6), A/Equine/Prague/1/56 (H7N7) (see, e.g., Donofrio et al., J Vet Diagn Invest. 1994 January; 6(1):39-43, Morley et al. Vet Microbiol. 1995 June; 45(1):81-92), A/equine/Miami/1/63 (H3N8) (see, e.g., Morley et al. Vet Microbiol. 1995 June; 45(1):81-92, Ozaki et al., Vet Microbiol. 2001 September 20; 82(2):111-9, Thomson et al., Vet Rec. 1977 May 28; 100(22):465-8, Mumford et al., Epidemiol Infect. 1988 June; 100(3):501-10, Donofrio et al., J Vet Diagn Invest. 1994 January; 6(1):39-43, Mumford et al., J Hyg (Lond). 1983 June; 90(3):385-95), A/Aichi/2/68 (H3N2) (see, e.g., Ozaki et al., Vet Microbiol. 2001 September 20; 82(2):111-9), A/equine/Tokyo/2/71 (H3N8) (see, e.g., Goto et al., J Vet Med Sci. 1993 February; 55(1):33-7), A/eq/LaPlata/1/88 (see, e.g., Lindstrom et al., Arch Virol. 1998; 143(8):1585-98), A/Equine/Jilin/1/89 (Eq/Jilin) (see, e.g., Webster & Thomas, Vaccine. 1993; 11(10):987-93), A/Equine/Alaska/1/91 (H3N8) (see, e.g., Webster & Thomas, Vaccine. 1993; 11(10):987-93), A/equine/Saskatoon/1/91 (H3N8) (see, e.g., Morley et al. Vet Microbiol. 1995 June; 45(1):81-92), A/equine/Rome/5/91 (H3N8) (see, e.g., Sugiura et al., J Virol Methods. 2001 October; 98(1):1-8), A/equine/La Plata/1/93 (H3N8) (see, e.g., Ozaki et al., Vet Microbiol. 2001 September 20; 82(2):111-9), A/equine/La Plata/1/93 (LP/93) (see, e.g., Sugiura et al., J Virol Methods. 2001 October; 98(1):1-8), A/eq/Holland/1/95 (H3N8) (see, e.g., van Maanen et al., Vet Microbiol. 2003 June 10; 93(4):291-306) and A/eq/Holland/2/95 (H3N8) (see, e.g., van Maanen et al., Vet Microbiol. 2003 June 10; 93(4):291-306), the disclosures of which are incorporated by reference in their entireties.

In another advantageous embodiment, the canine influenza, antigen, epitope or immunogen may be derived from an equine infected with influenza or an equine influenza strain derived from a recent isolate.

The influenza antigen, epitope or immunogen may also be isolated from any influenza strain such as, but not limited to, avian H5N1 influenza virus, A/Hong Kong/156/97 (A/HK/156/97) (see, e.g., Leneva et al., Antimicrob Agents Chemother. 2001 April; 45(4):1216-24), avian H7N1 influenza strain (see, e.g., Foni et al., New Microbiol. 2005 January; 28(1):31-5), avian H9N2 influenza virus (see, e.g., Leneva et al., Antimicrob Agents Chemother. 2001 April; 45(4):1216-24), avian influenza virus A/Chicken/HK/G9/97 (H9N2) (see, e.g., Leneva et al., Antimicrob Agents Chemother. 2001 April; 45(4):1216-24), avian influenza virus A/Quail/HK/G1/97 (H9N2) (see, e.g., Leneva et al., Antimicrob Agents Chemother. 2001 April; 45(4):1216-24), avian influenza virus A/Teal/HK/W312/97 (H6N1) (see, e.g., Leneva et al., Antimicrob Agents Chemother. 2001 April; 45(4):1216-24), avian pandemic influenza A viruses of avian origin (see, e.g., Audsley & Tannock, Expert Opin Biol Ther. 2004 May; 4(5):709-17), cold-adapted (ca) and temperature sensitive (ts) master donor strain, A/Leningrad/134/17/57 (H2N2) (see, e.g., Youil et al., Virus Res. 2004 June 15; 102(2):165-76), equine influenza virus (A/Equi 2 (H3N8), Newmarket 1/93) (see, e.g., Mohler et al., Biotechnol Bioeng. 2005 April 5; 90(1):46-58; Nayak et al., J Chromatogr B Analyt Technol Biomed Life Sci. 2005 July 8), equine-2 influenza virus (EIV; subtype H3N8) (see, e.g., Virology. 2001 August 15; 287(1):202-13), equine-2 influenza virus, A/Equine/Kentucky/1/91 (H3N8) (see, e.g., Youngner et al., Am J Vet Res. 2001 August; 62(8):1290-4), human influenza virus A(H3N2) isolates (see, e.g., Abed et al., J Infect Dis. 2002 October 15; 186(8):1074-80), human influenza virus A/Memphis/1/71 (H3N2) (see, e.g., Suzuki et al., Biochem J. 1996 September 1; 318 (Pt 2):389-93), human influenza virus A/Nanchang/933/95 (H3N2) virus (see, e.g., Scholtissek et al., J Virol. 2002 February; 76(4):1781-6), human influenza virus A/PR/8/34 (H1N1) virus (see, e.g., Scholtissek et al., J Virol. 2002 February; 76(4):1781-6), human influenza virus A/Singapore/57 (H2N2) virus (see, e.g., Scholtissek et al., J Virol. 2002 February; 76(4):1781-6), influenza virus A (see, e.g., Chare et al., J Gen Virol. 2003 October; 84(Pt 10):2691-703), influenza virus A PR/8/34 (PR8) virus (H1N1 subtype) (see, e.g., Mantani et al., Planta Med. 2001 April; 67(3):240-3), influenza virus A/Aichi/2/68(H3N2) (see, e.g., Miyamoto et al., Antiviral Res. 1998 August; 39(2):89-100), influenza virus A/Ann Arbor/6/60 cold-adapted virus (see, e.g., Treanor et al., J Virol. 1994 December; 68(12):7684-8), influenza virus A/Beijing 32/92 (H3N2) (see, e.g., Zakay-Rones et al., J Altern Complement Med. 1995 Winter; 1(4):361-9), influenza virus A/Charlottesville/31/95 (H1N1) (see, e.g., Gubareva et al., J Gen Virol. 2002 November; 83(Pt 11):2683-92), influenza virus A/Kawasaki/86 (H1N1) virus (see, e.g., Staschke et al., Virology. 1998 September 1; 248(2):264-74), influenza virus A/Korea/82 (H3N2) (see, e.g., Treanor et al., J Virol. 1994 December; 68(12):7684-8), influenza virus A/Leningrad/134/57 (see, e.g., Egorov et al., J Virol. 1998 August; 72(8):6437-41), influenza virus A/NWS/33 (H1N1) (see, e.g., Sidwell et al., Antiviral Res. 1998 February; 37(2):107-20), influenza virus A/PR/8/34 (H1N1) (see, e.g., Miyamoto et al., Antiviral Res. 1998 August; 39(2):89-100), influenza virus A/PR8/34 (see, e.g., Nunes-Correia et al., Biochemistry. 1999 January 19; 38(3):1095-101, Tree et al., Vaccine. 2001 May 14; 19(25-26):3444-50), influenza virus A/Puerto Rico (PR)/8/34 (see, e.g., Egorov et al., J Virol. 1998 August; 72(8):6437-41), influenza virus A/Puerto Rico/8-Mount Sinai (see, e.g., Mazanec et al., J Virol. 1995 February; 69(2):1339-43), influenza virus A/Shangdong 9/93 (H3N2) (see, e.g., Zakay-Rones et al., J Altern Complement Med. 1995 Winter; 1(4):361-9, Sidwell et al., Antiviral Res. 1998 February; 37(2):107-20), influenza virus A/Shingapol/1/57(H2N2) (see, e.g., Miyamoto et al., Antiviral Res. 1998 August; 39(2):89-100), influenza virus A/Singapore 6/86 (H1N1) (see, e.g., Zakay-Rones et al., J Altern Complement Med. 1995 Winter; 1(4):361-9), influenza virus A/Singapore/1/57 (H2N2) (see, e.g., Bantia et al., Antimicrob Agents Chemother. 1998 April; 42(4):801-7), influenza virus A/Texas 36/91 (H1N1) (see, e.g., Zakay-Rones et al., J Altern Complement Med. 1995 Winter; 1(4):361-9), influenza virus A/Texas/36/91 (H1N1) virus (see, e.g., Gubareva et al., J Infect Dis. 2001 February 15; 183(4):523-31, Halperin et al., Vaccine. 1998 August; 16(13):1331-5), influenza virus A/Texas/36/91 (H1N1) (see, e.g., Hayden et al., Antiviral Res. 1994 October; 25(2):123-31), influenza virus A/Udorn/72 virus infection (see, e.g., Shimizu et al., Virology. 1999 February 15; 254(2):213-9), influenza virus A/Victoria/3/75 (H3N2) (see, e.g., Sidwell et al., Antiviral Res. 1998 February; 37(2):107-20), influenza virus A/Virginia/88(H3N2) (see, e.g., Hayden et al., Antiviral Res. 1994 October; 25(2):123-31), influenza virus A/WSN/33 (H1N1) (see, e.g., Lu et al., Arch Virol. 2002; 147(2):273-84), influenza virus A/WSN/33 (see, e.g., Gujuluva et al., Virology. 1994 November 1; 204(2):491-505), influenza virus B (see, e.g., Chare et al., J Gen Virol. 2003 October; 84(Pt 10):2691-703), influenza virus B/Ann Arbor 1/86 (see, e.g., Zakay-Rones et al., J Altern Complement Med. 1995 Winter; 1(4):361-9), influenza virus B/Harbin/7/94 (see, e.g., Halperin et al., Vaccine. 1998 August; 16(13):1331-5, influenza virus B/Hong Kong/5/72 (see, e.g., Sidwell et al., Antiviral Res. 1998 February; 37(2):107-20), influenza virus B/Lee/40 (see, e.g., Miyamoto et al., Antiviral Res. 1998 August; 39(2):89-100), influenza virus B/Victoria group (see, e.g., Nakagawa et al., J Virol Methods. 1999 April; 79(1):113-20), influenza virus B/Yamagata 16/88 (see, e.g., Zakay-Rones et al., J Altern Complement Med. 1995 Winter; 1(4):361-9), influenza virus B/Yamagata group (see, e.g., Nakagawa et al., J Virol Methods. 1999 April; 79(1):113-20), influenza virus B/Yamanashi/166/98 (see, e.g., Hoffmann et al., Proc Natl Acad Sci USA. 2002 August 20; 99(17):11411-6), influenza virus C (see, e.g., Chare et al., J Gen Virol. 2003 October; 84(Pt 10):2691-703), influenza virus strain A/Equi/2/Kildare/89 (see, e.g., Quinlivan et al., J Clin Microbiol. 2004 February; 42(2): 759-63), influenza virus type B/Panama 45/90 (see, e.g., Zakay-Rones et al., J Altern Complement Med. 1995 Winter; 1(4):361-9), live, cold-adapted, temperature-sensitive (ca/ts) Russian influenza A vaccines (see, e.g., Palker et al., Virus Res. 2004 October; 105(2):183-94), Madin Darby Canine Kidney (MDCK)-derived cell line (see, e.g., Halperin et al., Vaccine. 2002 January 15; 20(7-8):1240-7), mouse-adapted influenza virus A/Guizhou/54/89 (H3N2 subtype) (see, e.g., Nagai et al., Biol Pharm Bull. 1995 February; 18(2):295-9), mouse-adapted influenza virus A/PR/8/34 (A/PR8) (see, e.g., Nagai et al., Antiviral Res. 1995 January; 26(1): 11-25), mouse-adapted influenza virus B/Ibaraki/2/85 (see, e.g., Nagai et al., Biol Pharm Bull. 1995 February; 18(2):295-9), Russian live attenuated influenza vaccine donor strains A/Leningrad/134/17/57, A/Leningrad/134/47/57 and B/USSR/60/69 (see, e.g., Audsley & Tannock, J Virol Methods. 2005 February; 123(2):187-93), swine H1 and H3 influenza viruses (see, e.g., Gambaryan et al., Virus Res. 2005 July 1), swine influenza A viruses (see, e.g., Landolt et al., Am J Vet Res. 2005 January; 66(1):119-24), swine influenza virus (SIV) (see, e.g., Clavijo et al., Can J Vet Res. 2002 April; 66(2): 117-21), swine influenza virus A/Sw/Ger 2/81 (see, e.g., Zakay-Rones et al., J Altern Complement Med. 1995 Winter; 1(4):361-9), swine influenza virus A/Sw/Ger 8533/91 (see, e.g., Zakay-Rones et al., J Altern Complement Med. 1995 Winter; 1(4):361-9), turkey influenza virus A/Tur/Ger 3/91 (see, e.g., Zakay-Rones et al., J Altern Complement Med. 1995 Winter; 1(4):361-9) and turkey influenza virus A/turkey/Minnesota/833/80 (H4N2) (see, e.g., Gubareva et al., J Virol. 1997 May; 71(5):3385-90), the disclosures of which are incorporated by reference.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also refers includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in the PCT Application Serial No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996) J. Immunol. 157:3242-3249; Suhrbier, A. (1997) Immunol. and Cell Biol. 75:402-408; Gardner et al. (1998) 12th World AIDS Conference, Geneva, Switzerland, Jun. 28-Jul. 3, 1998. Immunogenic fragments, for purposes of the present invention, will usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of an influenza protein or polyprotein. A polynucleotide encoding a fragment of the total protein or polyprotein, more advantageously, comprises or consists essentially of or consists of a minimum of 21 nucleotides, advantageously at least 42 nucleotides, and preferably at least 57, 87 or 150 consecutive or contiguous nucleotides of the sequence encoding the total protein or polyprotein. Epitope determination procedures, such as, generating overlapping peptide libraries (Hemmer B. et al., Immunology Today, 1998, 19 (4), 163-168), Pepscan (Geysen et al., (1984) Proc. Nat. Acad. Sci. USA, 81, 3998-4002; Geysen et al., (1985) Proc. Nat. Acad. Sci. USA, 82, 178-182; Van der Zee R. et al., (1989) Eur. J. Immunol., 19, 43-47; Geysen H. M., (1990) Southeast Asian J. Trop. Med. Public Health, 21, 523-533; MultipinR™ Peptide Synthesis Kits de Chiron) and algorithms (De Groot A. et al., (1999) Nature Biotechnology, 17, 533-561), and in PCT Application Serial No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The invention further comprises a complementary strand to a polynucleotide encoding an influenza antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

Hybridization reactions can be performed under conditions of different "stringency." Conditions that increase stringency of a hybridization reaction are well known. See for example, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the influenza polypeptides and functionally equivalent fragments thereof which may enhance, decrease or not significantly affect properties of the polypeptides encoded thereby. These functionally equivalent variants, derivatives, and fragments display the ability to retain influenza activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the influenza polynucleotide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}$=8; $N_{dif}$=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the influenza polynucleotides contained in a vector molecule or an expression vector and operably linked to a promoter element and optionally to an enhancer.

The vector is advantageously a poxvirus, particularly a vaccinia virus or an avipox virus, such as fowlpox virus and canarypox virus. Advantageously, the virus is a canarypox virus. Advantageous canarypox strains may be an attenuated strain. The vector can express at least one epitope from Kentucky strains, Newmarket strains and/or Ohio strains. Advantageous canarypox constructs include, but are not limited to, vCP 1529, vCP 1533 and vCP 2242. Recombinant avipox viruses (see, e.g., U.S. Pat. Nos. 5,505,941 and 5,756,103), such as an attenuated recombinant canarypox virus, for instance ALVAC, or an attenuated fowlpox virus, for instance TROVAC, are especially advantageous. In one advantageous embodiment, the recombinant ALVAC vaccine described by Edlund Toulemonde et al., Vet Rec. 2005 March 19; 156(12):367-71 may be used as a canine influenza vaccine. Other viruses that may be used in methods of the invention include, but are not limited to, vaccinia viruses, such as an attenuated vaccinia virus, for instance NYVAC, adenoviruses, such as canine adenoviruses (CAV), and herpesviruses, such as canine herpesvirus (CHV) or a feline herpesvirus (FHV).

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector needs not be capable of replication in the ultimate target cell or subject. The term includes cloning vectors also included are viral vectors.

The term "recombinant" means a polynucleotide semi-synthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an influenza antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an influenza peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986;

WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-influenza peptides or fragments thereof to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of influenza antigens, epitopes or immunogens. Advantageously, the vector contains and expresses a polynucleotide that includes, consists essentially of, or consists of a polynucleotide coding for (and advantageously expressing) an influenza antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an influenza antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of an influenza antigen, epitope or immunogen, the vector or vectors expressing the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different canine influenza isolates encoding the same proteins and/or for different proteins, but advantageously the same proteins. Preparations containing one or more vectors containing, consisting essentially of or consisting of polynucleotides encoding, and advantageously expressing, advantageously in vivo, an influenza antigen, fusion protein or an epitope thereof. The invention is also directed at mixtures of vectors that contain, consist essentially of, or consist of coding for, and express, different influenza antigens, epitopes or immunogens, e.g., an influenza antigen, epitope or immunogen from different species such as, but not limited to, humans, pigs, in addition to avian species including chicken, ducks and geese.

According to one embodiment of the invention, the expression vector is a viral vector, in particular an in vivo expression vector. In an advantageous embodiment, the expression vector is an adenovirus vector. Advantageously, the adenovirus is a human Ad5 vector, an E1-deleted and/or an E3-deleted adenovirus.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the attenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a particular embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol 7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1$\alpha$ can also be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promege Corp. comprising the human β-globin gene donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an influenza antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COS7 cells, MCF-7 cells, MCF-10A cells, Madin-Darby canine kidney (MDCK) lines, mink lung (Mvl Lu) cells, MRC-5 cells, U937 cells and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of an influenza antigen, epitope or immunogen in a target cell. Determination of the therapeutically effective amount is routine experimentation for one of ordinary skill in the art. In one embodiment, the formulation comprises an expression vector comprising a polynucleotide that expresses an influenza antigen, epitope or immunogen and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

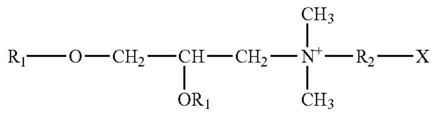

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5:about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1: about 5, and advantageously about 1: about 1 and about 1: about 2, e.g., 1:1 and 1:2.

The invention also provides for inactivated canine influenza vaccines. As used herein, the term "inactivated vaccine" means a vaccine composition containing an infectious organism or pathogen that is no longer capable of replication or growth. Inactivation may be accomplished by a variety of methods sufficient to prevent replication or growth of the organism while maintaining its immunogenicity.

The inactivated vaccine may be an inactivated form of an isolate of an influenza virus from an affected dog. The virus may be isolated from the alveoli or lung of an affected dog. In another embodiment, the inactivated vaccine may be an inactivated equine influenza. In an advantageous embodiment, the equine influenza is a Kentucky or Newmarket equine influenza. The inactivated vaccine may be an inactivated version of any one of the influenza strains described above.

An inactivated vaccine may be prepared as well from the harvested culture fluid. The virus may be produced either by inoculation of 10-11-day embryonated eggs (J. Violay et al U.S. Pat. No. 6,048,537) or by inoculation of BHK-21 cell culture (C. Ross et al Archiv. Für die gesamte Virusforschung 1970, 30, 82-88; T. Tolstova et al Acta Virol. 1966, 10, 315-321; Ho. Merten et al Adv. Exp. Med. Biol. 1996, 397, 141-151), of MDCK cell culture (J. Tree et al Vaccine 2001, 19, 3444-3450; Y. Ghendon et al Vaccine 2005, 23, 4678-4684; R. Brands et al Dev. Biol. Stand. 1999, 98, 93-100; R. Youil et al J. Virol. Methods 2004, 120, 23-31), of Vero cell culture (O. Kistner et al Vaccine 1998, 16, 960-968; E. Govorkova et al J. Virol. 1996, 70, 5519-5524). The allantoic fluid or the cell culture supernatant can be clarified by low centrifugation and/or filtration. The virus can be concentrated by ultrafiltration and can be purified by zonal centrifugation on sucrose gradient (J. Violay et al U.S. Pat. No. 6,048,537; O. Kistner et al idem), by gel filtration (D. Nayak et al J. Chromatogr. B Analyt. Technol. Biomed. Life Sci. 2005, 823, 75-81; S. Tomita et al Kitasato Arch. Exp. Med. 1971, 44, 185-196).

Inactivation may be achieved by treating the viruses by any of the methods commonly employed to make inactivated vaccines. These methods include but are not limited to formaldehyde treatment (O. Kistner et al idem; A. Garcia et al Avian Diseases 1998, 42, 248-256), betapropriolactone treatment (B. Bdowsky et al Vaccine 1991, 9, 398-402 and Vaccine 1993, 11, 343-348; N. Keverin et al Arch. Virol. 2000, 145, 1059-1066), ethylene-imine treatment (D. Swayne et al Avian Diseases 2001, 45, 355-365), treatment with organic solvents, treatment with detergents, treatment with Tween-ether or treatment with Triton X-100 (J. Vilay et al idem) for allantoic fluid. For the inactivation the concentration can be about 0.01-0.2% w/v for the formaldehyde; about 0.03-0.2% w/v for the betapropiolactone; about 0.5-20 mM for ethyleneimine. The methods recited herein serve as art-known examples for inactivating virus. Inactivated virus vaccines are usually administered mixed with an adjuvant. The inactivated vaccine can be administered to the animal by any of a plurality of methods which include but are not limited to inoculation intramuscularly or subcutaneously, spraying, ocularly, nasally, orally, or in ovo.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman et al., Proc. Natl. Acad. Sci., USA, 1996, 93, 2879-2883; WO98/16247), (3) an oil in water emulsion, such as the SPT emulsion described on p 147 of “Vaccine Design, The Subunit and Adjuvant Approach” published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778-780, Jun. 4, 1960.

With regard to structure, the acrylic or methacrylic acid polymers and EMA are preferably formed by basic units having the following formula:

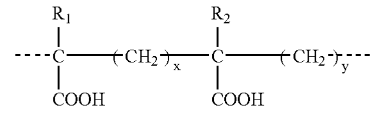

in which:

$R_1$ and $R_2$, which can be the same or different, represent H or $CH_3$ x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFN α), interferon β (IFN β), interferon γ, (IFN γ), interleukin-1α (IL-1 α), interleukin-1 β (IL-1 β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β (TNF β), and transforming growth factor β (TGF β). It is understood that cytokines can be co-administered and/or sequentially administered with the immunogenic or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to dogs).

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose can comprise, consist essentially of or consist of, in general terms, about in 1 μg to about 2000 μg, advantageously about 50 μg to about 1000 μg and more advantageously from about 100 μg to about 800 μg of plasmid expressing the influenza antigen, epitope or immunogen. When the therapeutic and/or pharmaceutical compositions based on a plasmid vector is administered with electroporation the dose of plasmid is generally between about 0.1 μg and 1 mg, advantageously between about 1 μg and 100 μg, advantageously between about 2 μg and 50 μg. The dose volumes can be between about 0.1 and about 2 ml, advantageously between about 0.2 and about 1 ml. These doses and dose volumes are suitable for the treatment of canines and other mammalian target species such as equines and felines.

The therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing an influenza antigen, epitope or immunogen. In the case of therapeutic and/or pharmaceutical compositions based on a poxvirus, a dose can be between about $10^2$ pfu and about $10^9$ pfu. The pharmaceutical composition contains per dose from about $10^5$ to $10^9$, advantageously from about $10^6$ to $10^8$ pfu of poxvirus or herpesvirus recombinant expressing the influenza antigen, epitope or immunogen.

The dose volume of compositions for target species that are mammals, e.g., the dose volume of canine compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

With inactivated compositions of the virus or organism or pathogen produced on the new cell culture, the animal may be administered approximately $10^4$-$10^9$ equivalent $CCID_{50}$ (titer before inactivation), advantageously approximately $10^5$-$10^8$ equivalent $CCID_{50}$ in a single dosage unit. The volume of one single dosage unit can be between 0.2 ml and 5.0 ml and advantageously between 0.5 ml and 2.0 ml and more advantageously about 2.0 ml. One or more administrations can be done; e.g. with two injections at 2-4 weeks interval, and advantageously with a boost about 3 weeks after the first injection.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oregon, USA)). Another approach to administer plasmid compositions is to use electroporation (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158). In another embodiment, the therapeutic composition is delivered to the animal by gene gun or gold particle bombardment. In an advantageous embodiment, the animal is a vertebrate. In a more advantageous embodiment, the vertebrate is a dog.

One embodiment of the invention is a method of eliciting an immune response against influenza in an animal, comprising administering a formulation for delivery and expression of a recombinant poxvirus influenza vaccine or inactivated influenza vaccine in an effective amount for eliciting an immune response. Still another embodiment of the invention is a method of inducing an immunological or protective response against influenza in an animal, comprising administering to the animal an effective amount of a formulation for delivery and expression of an influenza antigen, epitope or immunogen wherein the formulation comprises recombinant poxvirus influenza vaccine or inactivated influenza vaccine and a pharmaceutically or veterinarily acceptable carrier, vehicle or excipient.

The invention relates to a method to elicit, induce or stimulate the immune response of an animal, advantageously a vertebrate. In one embodiment, the vertebrate is cat, dog, Another embodiment of the invention is a kit for performing a method of inducing an immunological or protective response against influenza in an animal comprising a recombinant influenza poxvirus vaccine or an inactivated influenza vaccine and instructions for performing the method of delivery in an effective amount for eliciting an immune response in the animal.

The invention will now be further described by way of the following non-limiting examples.

EXAMPLE 1

Vaccination of Dogs with Canarypox Expressing H3 Genes

A study was conducted in which dogs were vaccinated dogs on days 0 and 21 with a canarypox expressing H3 genes from Kentucky (CP1529) and Newmarket (CP1533) equine influenza. The construction of CP1529 and CP1533 is described in Examples 1 (c5 locus), 4 and 5 of International Patent Publication WO99/44633, the disclosure of which is incorporated by reference. The nucleotide sequence of the donor plasmids pJT004 and pJT005 are presented in FIGS. 1 and 2.

Sera was collected and tested against H3N8 influenza viruses and the other viruses. As shown in Table 1, canarypox expressing hemagglutinin H3 genes induced a substantial amount of antibodies which specifically reacted with H3N8 strains but not with H1N1 or H7N7. Importantly antibodies were detectable within two weeks after the first immunization.

Accordingly, a canarypox expressing an influenza HA gene is immunogenic in dogs.

The purpose was the construction of an ALVAC donor plasmid for generation of an ALVAC recombinant expressing codon optimized EIV H3 HA (Ohio 03). The plasmid name was pALVAC C5 H6p-synthetic EIV H3 HA, pJY1571.1. The plasmid backbone is pALVAC C5 H6p. The promoter was a H6 promoter.

Figure 4B:
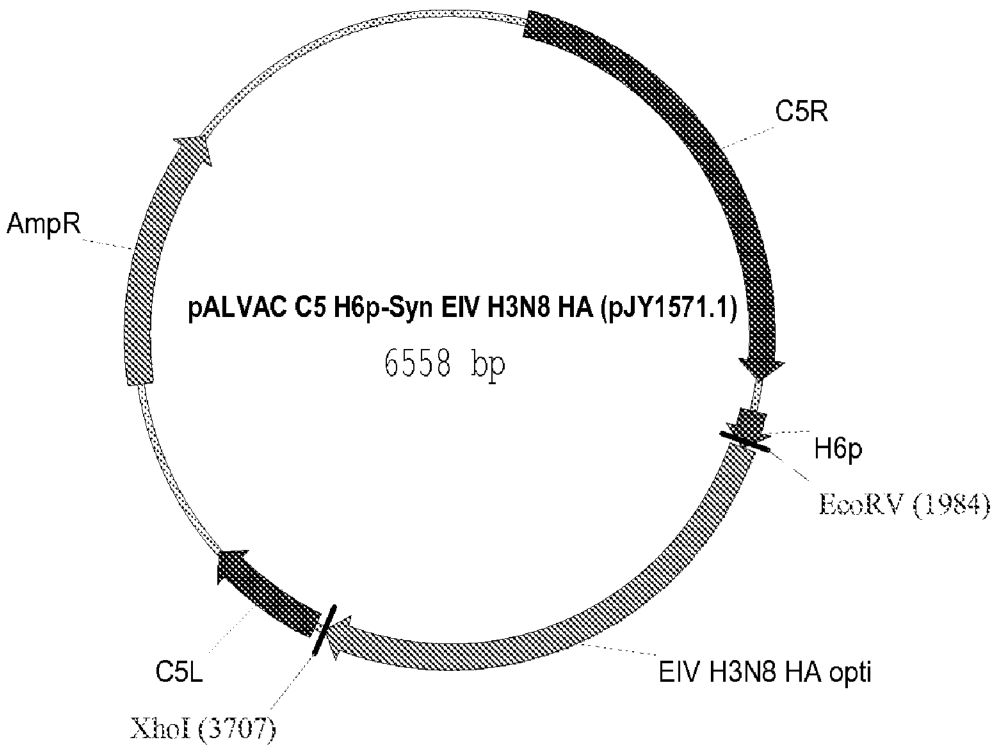
FIG. 4B illustrates pALVAC C5 H6p-synthetic EIV H3 HA, pJY1571.1.

The description of plasmid construction was as follows and presented schematically in FIG. 4A. The synthetic EIV H3 HA (Ohio 03) was isolated from a plasmid pEIV H3N8 HA by EcoRV/XhoI digestion, and ligated to EcoRV/XhoI digested donor plasmid pALVAC C5 H6p to create pALVAC C5 H6p-Synthetic EIV H3 HA. In the resulting plasmid, there are multiple cloning sites consisting of XhoI, Xba I, Cla I and Sma I between the HA ORF and the T5AT sequence which serves as the transcription termination signal. To bring the HA ORF and the T5AT sequence close together, those cloning sites were then subsequently removed by ligation of re-filled XhoI site with Sma I site. The resulting plasmid pJY1571.1 was then sequenced and confirmed to contain the correct sequence. A diagram of the resulting plasmid is presented in FIG. 4B. The predicted amino acid sequence of EIV H3 HA is shown in FIG. 5A and the nucleotide sequence of arms and insert with translation is shown in FIG. 5B.

TABLE 1

Vaccination of dogs with canarypox expressing H3 hemaglutinin genes

| Antigen | Bleed | VACCINATED GROUP | | | | | CONTROL GROUP | | | | |
|---|---|---|---|---|---|---|---|---|---|---|---|
| N/1/93 (H3N8) | D0 | 0 | 0 | 0 | 0 | 0 | 0 | 0 | 0 | 0 | 0 |
| | D14 | 0 | 63.8 | 69.9 | 31.4 | 96.7 | n.s. | n.s. | n.s. | n.s. | n.s. |
| | D21 | 104.1 | 91.4 | 121.5 | 74.6 | 121.5 | n.s. | n.s. | n.s. | n.s. | n.s. |
| | D36 | 106 | 96.7 | 111.7 | 69.9 | 123.6 | n.s. | n.s. | n.s. | n.s. | n.s. |
| | D51 | 76.2 | 55.1 | 74.6 | 38.3 | 69.9 | n.s. | n.s. | n.s. | n.s. | n.s. |
| N/2/93 (H3N8) | D0 | 0 | 0 | 0 | 0 | 0 | 0 | 0 | 0 | 0 | 0 |
| | D14 | 0 | 25.1 | 59.4 | 29.2 | 60.8 | n.s. | n.s. | n.s. | n.s. | n.s. |
| | D21 | 86.2 | 71.4 | 102.2 | 65.3 | 406 | n.s. | n.s. | n.s. | n.s. | n.s. |
| | D36 | 82.8 | 74.6 | 96.7 | 62.3 | 100.4 | n.s. | n.s. | n.s. | n.s. | n.s. |
| | D51 | 52.3 | 37.1 | 66.8 | 26.1 | 57.9 | n.s. | n.s. | n.s. | n.s. | n.s. |
| Pr/56 (H7N7) | D0 | 0 | 0 | 0 | 0 | 0 | 0 | 0 | 0 | 0 | 0 |
| | D14 | 0 | 19.3 | 0 | 24.1 | 0 | n.s. | n.s. | n.s. | n.s. | n.s. |
| | D21 | 0 | 0 | 0 | 0 | 0 | n.s. | n.s. | n.s. | n.s. | n.s. |
| | D36 | 0 | 0 | 0 | 0 | 0 | n.s. | n.s. | n.s. | n.s. | n.s. |
| | D51 | 0 | 0 | 0 | 0 | 0 | n.s. | n.s. | n.s. | n.s. | n.s. |
| PR8 (H1N1) | D0 | 0 | 0 | 0 | 0 | 0 | 0 | 0 | 0 | 0 | 0 |
| | D14 | 0 | 16.7 | 0 | 19.3 | 0 | n.s. | n.s. | n.s. | n.s. | n.s. |
| | D21 | 0 | 0 | 0 | 0 | 0 | n.s. | n.s. | n.s. | n.s. | n.s. |
| | D36 | 0 | 0 | 0 | 0 | 0 | n.s. | n.s. | n.s. | n.s. | n.s. |
| | D51 | 0 | 0 | 0 | 0 | 0 | 0 | 0 | 0 | 0 | 0 |

n.s. = no sample

EXAMPLE 2

Construction of the Donor Plasmid: pALVAC C5 H6p-Synthetic EIV H3 HA, pJY1571.1)

The HA gene was derived from equine influenza virus (EIV) H3N8 Ohio 03 strain isolated from a horse in 2003. The HA gene was synthetic with codon optimization for expression in mammalian cells. The amino acid sequence of EIV Ohio 03 strain HA was compared to that of New Market strain H3 HA and is presented in FIG. 3.

EXAMPLE 3

Construction of the Recombinant Canarypox vCP2242

The purpose of this example was the generation and characterization of ALVAC recombinant containing EIV H3N8 codon optimized HA inserted at C5 loci of ALVAC (vCP2242). The parental virus was ALVAC, the donor plasmid was pJY1571.1, the insertion site was a C5 Locus, the promoter was a H6 promoter and cells for in vitro recombination were primary chicken embryo fibroblast cells (1°CEF).

The in vitro recombination (IVR) was performed by transfection of 1°CEF cells with 15 μg of Not I-linearized donor plasmid pJY1571.1. The transfected cells were subsequently infected with ALVAC as rescue virus at MOI of 10. After 24 hr, the transfected-infected cells were harvested, sonicated and used for recombinant virus screening.

Recombinant plaques were screened based on the plaque lift hybridization method using a 821 bp EIV syn HA specific probe labeled with horse radish peroxidase (HRP) according to the manufacturer's protocol. After four sequential rounds of plaque purification, the recombinant designated as vCP2242 was generated and confirmed by hybridization as 100% positive for the EIV syn HA insert and 100% negative for the C5 ORF.

Figure 6:
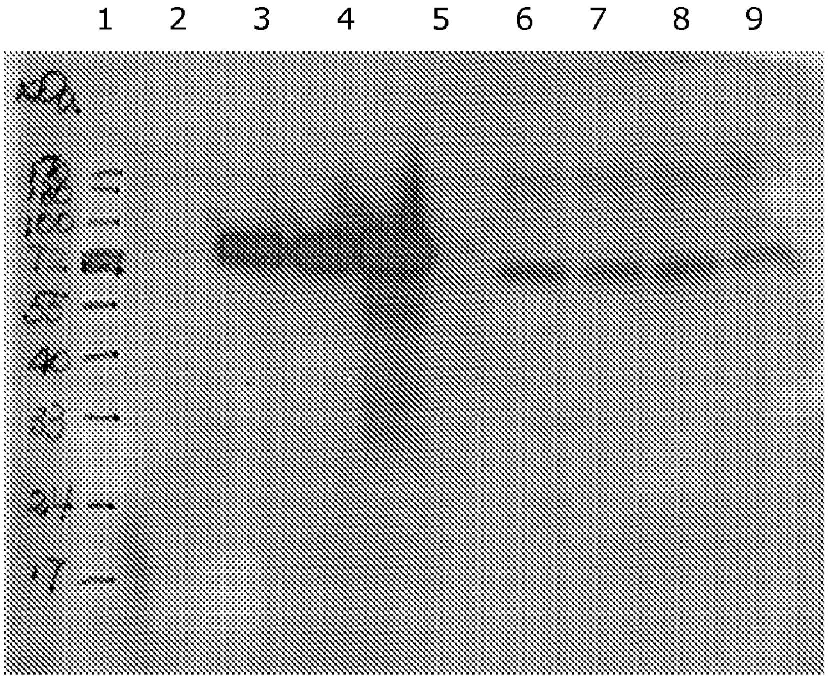
FIG. 6 illustrates a vCP2242 Western blot analysis. A 1/1,000 dilution of pooled anti-EIV antibody was used for the analysis. Lane 1: 5 μl Fermentas Prestain protein marker, lane 2: 15 μl ALVAC cell pellet, lane 3: 15 μl vCP2242. cell pellet, lane 4: 15 μl vCP2242. cell pellet, lane 5: 15 μl vCP1533 cell pellet, lane 6: space, lane 7: 40 μl ALVAC supernatant, lane 8: 40 μl vCP2242. supernatant, lane 9: 40 μl vCP2242. supernatant and lane 10: 40 μl vCP1533 supernatant.

Expression analysis and sequence analysis were performed. Expression analysis was performed by Western blot. Primary CEF cells were infected with vCP2242 stock at MOI of 10 and incubated at 37 C for 26.5 hrs. The cells and culture supernatant were then harvested. Sample proteins were separated on a 10% SDS-PAGE gel, transferred to Immobilon nylon membrane, and probed with a pool of monoclonal mouse anti-EIV HA antibodies (anti Eq/AK/91: 124-1D9-1, 124-3E3-3, 124-4F3-2 and H3N8 A Eq/miami/63 pool at 1/1,000 dilution). Peroxidase-conjugated goat anti-mouse antiserum was used as a secondary antibody and the bands were visualized using luminol reagents. vCP2242 showed a protein expression profile with a 80 kDa protein expressed in cell pellet, but not in the culture medium as presented in FIG. 6.

Results of the sequence analysis demonstrated that the sequences of the EIV syn HA and C5L and C5R of ALVAC were correct.

EXAMPLE 5

Kentucky Equine Influenza Nucleotide Sequences

```
DEFINITION Influenza A virus (A/equine/Kentucky/5/02(H3N8))
nonstructural protein gene, complete cds.
ACCESSION AY855345;
                                                        SEQ ID NO: 8
   1 agcaaaagca gggtgacaaa aacataatgg attccaacac tgtgtcaagc tttcaggtag

  61 actgttttct ttggcatgtc cgcaaacgat tcgcagacca agaactgggt gatgccccat

 121 tccttgaccg gcttcgccga gaccagaagt ccctaagggg aagaggtatc actcttggtc

 181 tggacatcga aacagccact catgcaggaa agcagatagt ggagcagatt ctggaaaagg

 241 aatcagatga ggcacttaaa atgaccattg cctctgttcc tacttcacgc tacttaactg

 301 acatgactct tgatgagatg tcaagagact ggttcatgct catgcccaag caaaaagtaa

 361 caggctccct atgtataaga atggaccagg caatcatgga taagaacatc atacttaaag

 421 caaactttag tgtgattttc gaaaggctgg aaacactaat actacttaga gccttcaccg

 481 aagaaggagc agtcgttggc gaaatttcac cattaccttc tcttccagga catactaatg

 541 aggatgtcaa aaatgcaatt ggggtcctca tcggaggact taaatggaat gataatacgg

 601 ttagaatctc tgaaactcta cagagattcg cttggagaag cagtcatgag aatgggagac

 661 cttcattccc ttcaaagcag aaatgaaaaa tggagagaac aattaagcca gaaatttgaa

 721 gaaataagat ggttgattga agaagtgcga catagattga aaaatacaga aaatagtttt

 781 gaacaaataa catttatgca agccttacaa ctattgcttg aagtagaaca agagataaga

 841 actttctcgt ttcagcttat ttaatgataa aaaacaccct tgtttctact

DEFINITION Influenza A virus (A/equine/Kentucky/5/02(H3N8)) matrix
protein gene, complete cds.
ACCESSION AY855344;
                                                        SEQ ID NO: 9
   1 agcaaaagca ggtagatatt taaagatgag tcttctgacc gaggtcgaaa cgtacgttct

  61 ctctatcgta ccatcaggcc ccctcaaagc cgagatcgcg cagagacttg aagatgtctt

 121 tgcagggaag aacaccgatc ttgaggcact catggaatgg ctaaagacaa gaccaatcct

 181 gtcacctttg actaaaggga ttttaggatt tgtattcacg ctcaccgtgc ccagtgagcg

 241 aggactgcag cgtagacgct ttgtccaaaa tgcccttagt ggaaacggag atccaaacaa

 301 catggacaga gcagtaaaac tgtacaggaa gcttaaaaga gaaataacat tccatggggc

 361 aaaagaggtg gcactaagct attccactgg tgcactagcc agctgcatgg gactcatata

 421 caacagaatg ggaactgtga caaccgaagt ggcatttggc ctggtatgcg ccacatgtga

 481 acagattgct gattcccagc atcgatctca caggcagatg gtgacaacaa ccaacccatt
```

-continued

```
 541 aatcagacat gaaaacagaa tggtattagc cagtaccacg gctaaagcca tggaacagat

 601 ggcaggatca agtgagcagg cagcagaggc catggaggtt gctagtaagg ctaggcagat

 661 ggtacaggca atgagaacca ttgggaccca ccctagctcc agtgccggtt tgaaagatga

 721 tctccttgaa aatttacagg cctaccagaa acggatggga gtgcaaatgc agcgattcaa

 781 gtgatcctct cgttattgca gcaagtatca ttgggatctt gcacttgata ttgtggattc

 841 ttgatcgtct tttcttcaaa ttcatttatc gtcgccttaa atacgggttg aaaagagggc

 901 cttctacgga aggagtacct gagtctatga gggaagaata tcggcaggaa cagcagaatg

 961 ctgtggatgt tgacgatggt cattttgtca acatagagct ggagtaaaaa actaccttgt

1021 ttctact
```

DEFINITION Influenza A virus (A/equine/Kentucky/5/02(H3N8)) neuraminidase gene, complete cds.
ACCESSION AY855343;

SEQ ID NO: 10

```
   1 agcaaaagca ggagtttaaa atgaatccaa atcaaaagat aatagcaatt ggatttgcat

  61 cattggggat attaatcatt aacgtcattc tccatgtagt cagcattata gtaacagtac

 121 tggtcctcaa taacaatgga acaggtctga actgcaaagg gacgatcata agagagtaca

 181 atgaaacagt aagagtagaa aaaattactc aatggtataa taccagtgca attaagtaca

 241 tagagagacc tccaaatgaa tactacatga acaacaccga accactttgt gaggcccaag

 301 gctttgcacc attttccaaa gataatggaa tacgaattgg gtcgagaggc catgtttttg

 361 tgataagaga accttttgta tcatgttcgc cctcagaatg tagaaccttt ttcctcacac

 421 agggctcatt actcaatgac aaacattcta acggcacagt aaaggaccga agtccatata

 481 ggactttgat gagtgtcaaa atagggcaat cacctaatgt gtatcaagct aggtttgaat

 541 cggtggcatg gtcagcaaca gcatgccatg atggaaaaaa atggatgaca gttggagtca

 601 cagggcccga caatcaagca attgcagtag tgaactatgg aggtgttccg gttgatatta

 661 ttaattcatg ggcaggggat atcttaagaa cccaagaatc atcatgcacc tgcattaaag

 721 gagactgtta ttgggtaatg actgatggac cggcaaatag gcaagctaaa tataggatat

 781 tcaaagcaaa agatggaaga gtaattggac agactgatat aagtttcaat gggggacaca

 841 tagaggagtg ttcttgttac cccaatgaag ggaaggtgga atgcatatgc agggacaatt

 901 ggactggaac aaatagacca attctggtaa tatcttctga tctatcgtac acagttggat

 961 atttgtgtgc tggcattccc actgacactc ctaggggaga ggatagtcaa ttcacaggct

1021 catgtacaag acctttggga aataaaggat acggtgtaaa aggtttcggg tttcgacaag

1081 gaactgacgt atgggccgga aggacaatta gtaggacttc aagatcagga ttcgaaataa

1141 taaaaatcag gaatggttgg acacagaaca gtaaagacca aatcaggagg caagtgatta

1201 tcgatgaccc aaattggtca ggatatagcg gttctttcac attgccggtt gaactaacaa

1261 aaaagggatg tttggtcccc tgtttctggg ttgaaatgat tagaggtaaa cctgaagaaa

1321 caacaatatg gacctctagc agctccattg tgatgtgtgg agtagatcat aaaattgcca

1381 gttggtcatg gcacgatgga gctattcttc cctttgacat cgataagatg taatttacga

1441 aaaaactcct tgtttctact
```

DEFINITION Influenza A virus (A/equine/Kentucky/5/02(H3N8)) nucleoprotein gene, complete cds.
ACCESSION AY855342;

SEQ ID NO: 11

```
   1 agcaaaagca gggtagataa tcactcactg agtgacatca aagtcatggc gtctcaaggc

  61 accaaacgat cctatgaaca gatggaaact gatggggaac gccagaatgc aactgaaatc
```

-continued 121 agagcatctg tcggaaggat ggtgggagga atcggccggt tttatgttca gatgtgtact 181 gagcttaaac taaacgacca tgaagggcgg ctgattcaga acagcataac aatagaaagg 241 atggtacttt cggcattcga cgaaagaaga aacaagtatc tcgaggagca tcccagtgct 301 ggaaaagacc ctaagaaaac gggaggcccg atatacagaa ggaaagatgg gaaatggatg 361 agggaactca tcctccatga taaagaagaa atcatgagaa tctggcgtca ggccaacaat 421 ggtgaagacg ctactgctgg tcttactcat atgatgatct ggcactccaa tctcaatgac 481 accacatacc aaagaacaag ggctcttgtt cggactggga tggatcccag aatgtgctct 541 ctgatgcaag gctcaaccct cccacggaga tctggagccg ctggtgctgc agtaaaaggt 601 gttggaacaa tggtaatgga actcatcaga atgatcaaac gcggaataaa tgatcggaat 661 ttctggagag gtgaaaatgg tcgaaggacc agaattgctt atgaaagaat gtgcaatatc 721 ctcaaaggga aatttcagac agcagcacaa cgggctatga tggaccaggt gagggaaggc 781 cgcaatcctg gaaacgctga gattgaggat ctcattttct tagcacgatc agcacttatt 841 ttgagaggat cagtagccca taaatcatgc ctacctgcct gtgtttatgg ccttgcagta 901 accagtgggt atgactttga gaaggaagga tactctctgg ttggaattga tcctttcaaa 961 ctactccaga acagtcaaat tttcagtcta atcagaccaa aagaaaaccc agcacacaag 1021 agccagttgg tgtggatggc atgccattct gcagcatttg aggacctgag agttttgaat 1081 ttcattagag gaaccaaagt aatcccaaga ggacagttaa caaccagagg agttcaaatt 1141 gcttcaaatg aaaacatgga gacaatagat tctagcacac ttgaactgag aagcaaatat 1201 tgggcaataa ggaccagaag tggaggaaac accagtcaac agagagcatc tgcaggacag 1261 ataagtgtgc aacctacttt ctcagtacag agaaatcttc cctttgagag agcaaccatt 1321 atggctgcat tcactggtaa cactgaaggg aggacttccg acatgagaac ggaaatcata 1381 aggatgatgg aaagtgccaa atcagaagat gtgtctttcc aggggcgggg agtcttcgag 1441 ctctcggacg aaaaggcaac gaacccgatc gtgccttcct ttgacatgag caatgaaggg 1501 tcttatttct tcggagacaa tgctgaggaa tttgacagtt aaagaaaaat acccttgttt 1561 ctact DEFINITION Influenza A virus (A/equine/Kentucky/5/02(H3N8))
hemagglutinin precursor, gene, complete cds.
ACCESSION AY855341;

SEQ ID NO: 12

1 agcaaaagca ggggatattt ctgtcaatca tgaagacaac cattattttg atactactga 61 cccattgggc ctacagtcaa aacccaatca gtggcaacaa cacagccaca ttgtgtctgg 121 gacaccatgc agtagcaaat ggaacattgg taaaaacaat aagtgatgat caaattgagg 181 tgacaaatgc tacagaatta gttcagagca tttcaatggg gaaaatatgc aacaactcat 241 atagaattct agatggaaga aattgcacat taatagatgc aatgctagga gacccccact 301 gtgacgtctt tcagtatgag aattgggacc tctttataga aagaagcagc gctttcagca 361 attgctaccc atatgacatc cctgactatg catcgctccg atccattgta gcatcctcag 421 gaacattgga attcacagca gagggattca catggacagg tgtcactcaa aacggaagaa 481 gtggagcctg caaaagggga tcagccgata gtttctttag ccgactgaat tggctaacaa 541 aatctggaaa ctcttacccc acattgaatg tgacaatgcc taacaataaa aatttcgaca 601 agctatacat ctgggggatt catcacccga gctcaaatca agagcagaca aaattgtaca 661 tccaagaatc aggacgagta acagtctcaa caaaaagaag tcaacaaaca ataatcccta 721 acatcggatc tagaccgtgg gtcagaggtc aatcaggcag gataagcata tactggacca -continued 781 ttgtaaaacc tggagatatc ctaatgataa acagtaatgg caacttagtt gcaccgcggg 841 gatattttaa attgaaaaca gggaaaagct ctgtaatgag atcagatgca cccatagaca 901 tttgtgtgtc tgaatgtatt acaccaaatg gaagcatctc caacgacaag ccattccaaa 961 atgtgaacaa agttacatat ggaaaatgcc ccaagtatat caggcaaaac actttaaagt 1021 tggccactgg gatgaggaat gtaccagaaa agcaaatcag aggaatcttt ggagcaatag 1081 cgggattcat cgaaaacggc tgggaaggaa tggttgatgg gtggtatggg ttccgatatc 1141 aaaactctga aggaacaggg caagctgcag atctaaagag cactcaagca gccatcgacc 1201 agattaatgg aaagttaaac agagtgattg aaagaaccaa tgagaaattc catcaaatag 1261 agaaggaatt ctcagaagta gaaggaagaa ttcaggactt ggagaaatat gtagaagaca 1321 ccaaaataga cctatggtcc tacaatgcag aattgctggt ggctctagaa aatcaacata 1381 caattgactt aacagatgca gaaatgaata aattattcga gaagactaga cgccagttaa 1441 gagaaaacgc agaagacatg ggaggtggat gtttcaagat ttaccacaaa tgtgataatg 1501 catgcattgg atcaataaga aatgggacat atgaccatta catatacaga gatgaagcat 1561 taaacaaccg atttcaaatc aaaggtgttg agttgaaatc aggctacaaa gattggatac 1621 tgtggatttc attcgccata tcatgcttct taatttgcgt tgttctattg ggtttcatta 1681 tgtgggcttg ccaaaaaggc aacatcagat gcaacatttg catttgagta aactgatagt 1741 taaaaacacc cttgtttcta ct DEFINITION Influenza A virus (A/equine/Kentucky/5/02(H3N8)) PA polymerase gene, complete cds.
ACCESSION AY855340;

SEQ ID NO: 13

1 agcgaaagca ggtactgatc caaaatggaa gactttgtgc gacagtgctt caatccaatg 61 atcgtcgagc ttgcggaaaa ggcaatgaaa gaatatggag aggacccgaa aatcgaaaca 121 aacaaatttg cagcaatatg cactcacttg gaagtctgct tcatgtactc ggatttccac 181 tttattaatg aactgggtga gtcagtggtc atagagtctg gtgacccaaa tgctcttttg 241 aaacacagat ttgaaatcat tgaggggaga gatcgaacaa tggcatggac agtggtaaac 301 agcatctgca acaccacaag agctgaaaaa cctaaatttc ttccagattt atacgactat 361 aaggagaaca gatttgttga aattggtgtg acaaggagag aagttcacat atactacctg 421 gagaaggcca acaaaataaa gtctgagaaa acacatatcc acattttctc atttacagga 481 gaggaaatgg ctacaaaagc ggactatact cttgatgaag agagtagagc caggatcaag 541 accagactat tcactataag acaagaaatg gccagtagag gcctctggga ttcctttcgt 601 cagtccgaga gaggcgaaga gacaattgaa gaaagatttg aaatcacagg gacgatgcgc 661 aagcttgcca attacagtct cccaccgaac ttctccagcc ttgaaaattt tagagtctat 721 gtggatggat tcgaaccgaa cggctgcatt gagagtaagc tttctcaaat gtccaaagaa 781 gtaaatgcca gaatcgaacc attttcaaag acaacacccc gaccactcaa aatgccaggt 841 ggtccaccct gccatcagcg atctaaattc ttgctaatgg atgctctgaa actgagcatt 901 gaggacccaa gtcacgaggg agagggaata ccactatatg atgcaatcaa atgcatgaaa 961 actttctttg gatggaaaga gcccagtatt gttaaaccac atgaaaaggg tataaacccg 1021 aactatctcc aaacttggaa gcaagtatta gaagaaatac aagaccttga gaacgaagaa 1081 aggaccccca agaccaagaa tatgaaaaaa acaagccaat tgaaatgggc actaggtgaa 1141 aatatggcac cagagaaagt ggattttgag gattgtaaag acatcagtga tttaaaacag 1201 tatgacagcg atgagccaga aacaaggtct cttgcaagtt ggattcaaag tgagttcaac -continued 1261 aaagcttgtg agctgacaga ttcaagctgg atagagctcg atgaaattgg ggaggatgtc 1321 gccccaatag aatacattgc gagcatgagg agaaattatt ttactgctga gatttcccat 1381 tgtagagcaa cagaatatat aatgaaagga gtgtacatca acactgctct actcaatgca 1441 tcctgtgctg cgatggatga atttcaatta attccgatga taagtaaatg caggaccaaa 1501 gaagggagaa ggaaaacaaa tttatatgga ttcataataa agggaaggtc ccatttaaga 1561 aatgatactg acgtggtgaa ctttgtaagt atggaatttt ctctcactga tccaagattt 1621 gagccacaca aatgggaaaa atactgcgtt ctagaaattg gagacatgct tctaaggact 1681 gctgtaggtc aagtgtcaag acccatgttt ttgtatgtaa ggacaaatgg aacctctaaa 1741 attaaaatga aatggggaat ggaaatgagg cgctgcctcc ttcagtctct gcaacagatt 1801 gaaagcatga tcgaagctga gtcctcagtc aaagaaaagg acatgaccaa agaatttttt 1861 gagaacaaat cagagacatg gcctatagga gagtccccca aaggagtgga agagggctca 1921 atcgggaagg tttgcaggac cttattagca aaatctgtgt ttaacagttt atatgcatct 1981 ccacaactgg aagggttttc agctgaatct aggaaattac ttctcattgt tcaggctctt 2041 agggataacc tggaacctgg aacctttgat attggggggt tatatgaatc aattgaggag 2101 tgcctgatta atgatccctg ggttttgctt aatgcatctt ggttcaactc cttccttaca 2161 catgcactga agtagttgtg gcaatgctac tatttgctat ccatactgtc caaaaaagta 2221 ccttgtttct act DEFINITION Influenza A virus (A/equine/Kentucky/5/02(H3N8)) PB1 polymerase 1 gene, complete cds.
ACCESSION AY855339;

SEQ ID NO: 14

1 agcgaaagca ggcaaaccat ttgaatggat gtcaatccga ctctactttt cttaaaggtg 61 ccagcgcaaa atgctataag cacaacattc ccttatactg gagatcctcc ctacagtcat 121 ggaacaggga caggatacac catggatact gtcaacagaa cacaccaata ttcagaaaag 181 gggaaatgga caacaaacac tgagattgga gcaccacaac ttaatccaat cgatggacca 241 cttcctgaag acaatgaacc aagtgggtac gcccaaacag attgtgtatt ggaagcaatg 301 gctttccttg aagaatccca tcccggaatc tttgaaaatt cgtgtcttga aacgatggag 361 gtgattcagc agacaagagt ggacaaacta acacaaggcc gacaaactta tgattggacc 421 ttgaatagga atcaacctgc cgcaacagca cttgctaata caattgaagt gttcagatca 481 aatggtctga cttccaatga atcagggagg ttgatggact tcctcaaaga tgtcatggag 541 tccatgaaca aggaagaaat ggaaataaca acacacttcc aacgaaagag aagagtaaga 601 gacaacatga caaagagaat ggtaacacag agaaccatag ggaagaaaaa acaacgatta 661 aacagaaaga gttatctaat cagaacatta accctaaaca caatgaccaa ggacgctgag 721 agagggaaat tgaaacgacg agcaatcgca accccaggga tgcagataag aggatttgta 781 tattttgttg aaacactagc ccgaagaata tgtgaaaagc ttgaacaatc aggattgcca 841 gttggcggta atgagaaaaa ggccaaactg gctaatgtcg tcagaaaaat gatgactaat 901 tcccaagaca ctgaactctc cttcaccatc actggggaca ataccaaatg gaatgaaaat 961 cagaacccac gcatattcct ggcaatgatc acatacataa ctagaaacca gccagaatgg 1021 ttcagaaatg ttctaagcat tgcaccgatt atgttctcaa ataaaatggc aagactgggg 1081 aaaggatata tgtttgaaag caaaagtatg aaactgagag ctcaaatacc agcagaaatg 1141 ctagcaagca ttgacctgaa atatttcaat gattcaacaa aaaagaaaat taaaaagata 1201 cgaccacttc tggttgacgg gactgcttca ctgagtcctg gcatgatgat gggaatgttc -continued 1261 aacatgttga gcactgtgct gggtgtatcc atattaaacc tgggccagag gaaatacaca 1321 aagaccacat actggtggga tggtctgcaa tcatccgatg actttgcttt gatagtgaat 1381 gcgcctaatc atgaaggaat acaagctgga gtagacagat tctatagaac ttgcaaactg 1441 gtcgggatca acatgagcaa aaagaagtcc tacataaata gaaccggaac attcgaattc 1501 acaagctttt tctaccggta tggttttgta gccaatttca gcatggaact acccagtttt 1561 ggggtttccg gaataaatga atctgcagac atgagcattg gagtgacagt catcaaaaac 1621 aacatgataa ataatgatct cggtcctgcc acggcacaaa tggcactcca actcttcatt 1681 aaggattacc ggtacacata ccggtgccat agaggtgata cccagataca aaccagaaga 1741 tcttttgagt tgaagaaact gtgggaacag actcgatcaa agactggtct actggtatca 1801 gatgggggtc caaacctata taacatcaga aacctacaca tcccggaagt ttgtttaaaa 1861 tgggagctaa tggatgaaga ttataagggg aggctatgca atccattaaa tcctttcgtt 1921 agtcacaaag aaattgaatc agtcaacagt gcagtagtaa tgcctgcgca tggccctgcc 1981 aaaagcatgg agtatgatgc tgttgcaaca acacattctt ggatccccaa gaggaaccgg 2041 tccatattga acacaagcca aaggggaata ctcgaagatg agcagatgta tcagaaatgc 2101 tgcaacctgt ttgaaaaatt cttccccagc agctcataca gaagaccagt cggaatttct 2161 agtatggttg aggccatggt gtccagggcc cgcattgatg cacgaattga cttcgaatct 2221 ggacggataa agaaggatga gttcgctgag atcatgaaga tctgttccac cattgaagag 2281 ctcagacggc aaaaatagtg aatttagctt gatcttcatg aaaaaatgcc ttgtttctac 2341 t DEFINITION Influenza A virus (A/equine/Kentucky/5/02(H3N8)) PB2 polymerase 2 gene, complete cds.
ACCESSION AY855338;

SEQ ID NO: 15

1 agcgaaagca ggtcaaatat attcaatatg gagagaataa aagaactgag agatctgatg 61 ttacaatccc gcacccgcga gatactaaca aaaactactg tggaccacat ggccataatc 121 aagaaataca catcaggaag acaagagaag aaccctgcac ttaggatgaa atggatgatg 181 gcaatgaaat acccaattac agcagataag aggataatgg agatgattcc tgagagaaat 241 gaacagggac aaaccctttg gagcaaaacg aacgatgctg gctcagaccg cgtaatggta 301 tcacctctgg cagtgacatg gtggaatagg aatggaccaa caacgagcac aattcattat 361 ccaaaagtct acaaaactta ttttgaaaag gttgaaagat tgaaacacgg aacctttggc 421 cccgttcatt ttaggaatca agtcaagata agacgaagag ttgatgtaaa ccctggtcac 481 gcggacctca gtgccaaaga agcacaagat gtgatcatgg aagttgtttt cccaaatgaa 541 gtgggagcca gaattctaac atcggaatca caactaacaa taaccaaaga gaaaaaggaa 601 gaacttcagg actgcaaaat tgctcccttg atggtagcat acatgctaga aagagagttg 661 gtccgaaaaa caaggttcct cccagtggca ggcggaacaa gcagtgtata cattgaagtg 721 ttgcatctga ctcagggaac atgctgggag caaatgtaca ccccaggagg agaagttaga 781 aacgatgata ttgatcaaag tttaattatt gcagcccgga acatagtgag aagagcgaca 841 gtatcagcag atccactagc atccctactg gaaatgtgcc acagtacaca gattggtgga 901 ataaggatgg tagacatcct taagcagaat ccaacagagg aacaagctgt ggatatatgc 961 aaagcagcaa tgggattgag aattagctca tcattcagct ttggtggatt caccttcaaa 1021 agaacaagtg gatcatcagt caagagagaa gaagaaatgc ttacgggcaa ccttcaaaca 1081 ttgaaaataa gagtgcatga gggctatgaa gaattcacaa tggtcggaag aagagcaaca -continued 1141 gccattctca gaaaggcaac cagaagattg attcaattga tagtaagtgg gagagatgaa 1201 caatcaattg ctgaagcaat aattgtagcc atggtgtttt cgcaagaaga ttgcatgata 1261 aaagcagttc gaggcgattt gaactttgtt aatagagcaa atcagcgttt gaaccccatg 1321 catcaactct tgaggcattt ccaaaaagat gcaaaagtgc ttttccaaaa ttggggaatt 1381 gaacccatcg acaatgtaat gggaatgatt ggaatattgc ctgacatgac cccaagcacc 1441 gagatgtcat tgagaggagt gagagtcagc aaaatgggag tggatgagta ctccagcact 1501 gagagagtgg tggtgagcat tgaccgtttt ttaagagttc gggatcaaag gggaaacata 1561 ctactgtccc ctgaagaagt cagtgaaaca caaggaacgg aaaagctgac aataatttat 1621 tcgtcatcaa tgatgtggga gattaatggt cccgaatcag tgttggtcaa tacttatcaa 1681 tggatcatca ggaactggga aattgtaaaa attcagtggt cacaggaccc cacaatgtta 1741 tacaataaga tagaatttga gccattccag tccctggtcc ctagggccac cagaagccaa 1801 tacagcggtt tcgtaagaac cctgtttcag caaatgcgag atgtacttgg aacatttgat 1861 actgctcaaa taataaaact cctccctttt gccgctgctc ctccggaaca gagtaggatg 1921 cagttctctt ctttgactgt taatgtaaga ggatcgggaa tgaggatact tgtaagaggc 1981 aattccccag tgttcaacta caataaagcc actaaaaggc tcacagtcct cggaaaggat 2041 gcaggtgcgc ttactgagga cccagatgaa ggtacggctg gagtagaatc tgctgttcta 2101 agagggtttc tcattttagg taaagaaaac aagagatatg gcccagcact aagcatcaat 2161 gaactaagca aacttgcaaa aggggagaaa gccaatgtac taattgggca aggggacgta 2221 gtgttggtaa tgaaacggaa acgtgactct agcatactta ctgacagcca gacagcgacc 2281 aaaaggattc ggatggccat caattagtgt tgaattgttt aaaaacgacc ttgtttctac 2341 t DEFINITION Influenza A virus (A/equine/Kentucky/1/91 (H3N8))
hemagglutinin precursor (HA) gene, complete cds.
ACCESSION L39918;

SEQ ID NO: 16

1 agcaaaagca ggggatattt ctgtcaatca tgaagacaac cattattttg atactactga 61 cccattgggt ctacagtcaa aacccaacca gtggcaacaa cacagccaca ttatgtctgg 121 gacaccatgc agtagcaaat ggaacattgg taaaaacaat aactgatgac caaattgagg 181 tgacaaatgc tactgaatta gttcagagca tttcaatagg gaaaatatgc aacaactcat 241 atagagttct agatggaaga aattgcacat taatagatgc aatgctagga gacccccact 301 gtgatgtctt tcagtatgag aattgggacc tcttcataga aagaagcagc gctttcagca 361 gttgctaccc atatgacatc cctgactatg catcgctccg gtccattgta gcatcctcag 421 gaacattgga attcacagca gagggattca catggacagg tgtcactcaa aacggaagaa 481 gtggatcctg caaaagggga tcagccgata gtttctttag ccgactgaat tggctaacaa 541 aatctggaaa ctcttacccc acattgaatg tgacaatgcc taacaataaa aatttcgaca 601 aactatacat ctgggggatt catcacccga gctcaaacga agagcagaca aaattgtaca 661 tccaagaatc aggacgagta acagtctcaa caaaaagaag tcaacaaaca ataatcccta 721 acatcggatc tagaccgtgg gtcaggggtc aatcaggcag gataagcata tactggacca 781 ttgtaaaacc tggagatatc ctaatgataa acagtaatgg caacttagtt gcaccgcggg 841 gatattttaa attgaaaaca gggaaaagct ctgtaatgag atcagatgca cccatagaca 901 tttgtgtgtc tgaatgtatt acaccaaatg gaagcatccc caacgacaaa ccatttcaaa 961 atgtgaacaa agttacatat ggaaaatgcc ccaagtatat caggcaaaac actttaaagc -continued

```
1021 tggccactgg gatgaggaat gtaccagaaa agcaaatcag aggaatcttt ggagcaatag

1081 cgggattcat agaaaacggc tgggaaggaa tggttgatgg gtggtatgga ttccgatatc

1141 aaaactcgga aggaacagga caagctgcag atctaaagag cactcaagca gccatcgacc

1201 agatcaatgg aaaattaaac agagtgattg aaaggaccaa tgagaaattc catcaaatag

1261 agaaggaatt ctcagaagta gaagggagaa tccaggattt ggagaagtat gtagaagaca

1321 ccaaaataga cctatggtcc tacaatgcag aattgctggt ggctctagaa aatcaacata

1381 caattgactt aacagatgca gaaatgaata aattattcga gaagactaga cgccagttaa

1441 gagaaaacgc ggaagacatg ggaggtggat gtttcaagat ataccacaaa tgtgataatg

1501 catgcattgg atcaataaga aatgggacat atgaccatta catatacaga gatgaagcat

1561 taaacaaccg gtttcaaatc aaaggtgttg agttgaaatc aggctacaaa gattggatac

1621 tgtggatttc attcgccata tcatgcttct taatttgcgt tgttctattg ggtttcatta

1681 tgtgggcttg ccaaaaaggc aacatcagat gcaacatttg catttgagta aactgatagt

1741 taaaaacacc cttgtttcta ct
```

DEFINITION Influenza A virus (A/equine/Kentucky/1/92(H3N8))
hemagglutinin precursor (HA) gene, complete cds.
ACCESSION L39917;

SEQ ID NO: 17

```
   1 agcaaaagca ggggatattt ctgtcaatca tgaagacaac cattattttg atactactga

  61 cccattgggt ctacagtcaa aacccaacca gtggcaacaa cacagccaca ttatgtctgg

 121 gacaccatgc agtagcaaat ggaacattgg taaaaacaat aactgatgac caaattgagg

 181 tgacaaatgc tactgaatta gttcagagca tttcaatagg gaaaatatgc aacaactcat

 241 atagggttct agatggaaga aattgcacat taatagatgc aatgctagga gaccccccact

 301 gtgatgtctt tcagtatgag aattgggacc tcttcataga aagaagcagc gctttcagca

 361 attgctaccc atatgacatc cctgactatg catcgctccg gtccattgta gcatcctcag

 421 gaacattaga attcacagca gagggattca catggacagg tgtcactcaa aacggaagaa

 481 gtggagcctg caaaagggga tcagccgata gtttctttag ccgactgaat tggctaacaa

 541 aatctggaaa ctcttacccc acattgaatg tgacaatgcc taacaataaa aatttcgaca

 601 aactatacat ctgggggatt catcacccga gctcaaacaa tgagcagaca aaattgtata

 661 tccaagaaac aggacgagta acagtctcaa caaaaagaag tcaacaaaca ataatcccta

 721 acatcggatc tagaccgtgg gtcaggggtc aatcaggcag gataagcata tactggacca

 781 ttgtaaaacc tggagatatc ctaatgataa acagcaatgg caacttagtt gcaccgcggg

 841 gatattttaa attgagaaca gggagaagct ctgtaatgag atcagatgca cccatagaca

 901 tttgtgtgtc tgaatgtatt acaccaaatg gaagcatccc caacgacaaa ccatttcaaa

 961 atgtgaacaa agttacatat ggaaaatgcc ccaaatatat caggcaaaac actttaaagc

1021 tggccactgg gatgaggaat gtaccagaaa agcaaatcag aggaatcttt ggagcaatag

1081 cgggattcat agaaaacggc tgggaaggaa tggttgatgg gtggtatgga ttccgatatc

1141 aaaactcgga aggaacagga caagctgcag atctaaagag cactcaagca gccatcgacc

1201 agatcaatgg aaaattaaac agagtgattg aaaggaccaa tgagaaattc catcaaatag

1261 agaaggaatt ctcagaagta gaagggagaa tccaggattt ggagaagtat gtagaagaca

1321 ccaaaataga cctatggtcc tacaatgcag aattgctagt ggctctagaa aatcaacata

1381 caattgactt aacagacgca gaaatgaata aattattcga gaagactaga cgccagttaa

1441 gagaaaacgc ggaagacatg ggaggtggat gtttcaagat ttaccacaaa tgtgataatg
```

-continued 1501 catgcattgg atcaataaga aatgggacat atgaccatta catatacaga gatgaagcat 1561 taaacaaccg atttcaaatc aaaggtgttg aattaaaatc aggctacaaa gattggatac 1621 tgtggatttc attcgccata tcatgcttct taatttgtgt tgttctattg ggtttcatta 1681 tgtgggcttg ccaaaaaggc aacatcagat gcaacatttg catttgagta aactgatagt 1741 taaaaacacc cttgtttcta ct DEFINITION Influenza A virus (A/equine/Kentucky/1/90(H3N8))
hemagglutinin precursor (HA) gene, complete cds.
ACCESSION L39915;

SEQ ID NO: 18

1 agcaaaagca ggggatattt ctgtcaatca tgaaaacaac cattattttg atactactga 61 cccattgggt ctacagtcaa aacccaacca gtggcaacaa cacagccaca ttatgtctgg 121 gacaccatgc agtagcaaat ggaacattgg taaaaacaat aactgatgac caaattgagg 181 tgacaaatgc tactgaatta gttcagagca tttcaatagg aaaaatatgc aacaactcat 241 atagggttct agatggaaga aattgcacat taatagatgc aatgctagga gaccctcact 301 gtgatgtctt tcagtatgag aattgggacc tcttcataga aagaagcagc gctttcagca 361 attgctaccc atatgacatc cctgactatg catcgctccg gtccattgta gcatcctcag 421 gaacattaga attcacagca gagggattca catggacagg tgtcactcaa aacggaggaa 481 gtggagcctg caaaagagga tcagccgata gtttctttag ccgactgaat tggctaacaa 541 aatctggaaa ctcttacccc acattgaatg tgacaatgcc taacaataaa aatttcgaca 601 aactatacat ctgggggatt catcacccga gctcaaacaa tgagcagaca aaattgtata 661 tccaagaatc aggacgagta acagtctcaa caaaaagaag tcaacaaaca ataatcccta 721 acatcggatc tagaccgtgg gtcaggggtc aatcaggcag gataagcata tactggacca 781 ttgtaaaacc tggagatatc ctaatgataa acagtaatgg caacttagtt gcaccgcggg 841 gatattttaa attgagaaca gggaaaagct ctgtaatgag atcagatgca cccatagaca 901 cttgtgtgtc tgaatgtatt acaccaaatg gaagcatccc caacgacaaa ccatttcaaa 961 atgtgaacaa agttacatat ggaaaatgcc ccaagtatat caggcaaaac actttaaagc 1021 tggccactgg gatgaggaat gtaccagaaa agcaaatcag aggaatcttt ggagcaatag 1081 cgggattcat agaaaacggc tgggaaggaa tggttgatgg gtggtatgga ttccgatatc 1141 aaaactcgga aggaacagga caagctgcag atctaaagag cactcaagca gccatcgacc 1201 agatcaatgg aaaattaaac agagtgattg aaaggaccaa tgagaaattc catcaaatag 1261 agaaggaatt ctcagaagta gaagggagaa tcaaggactt ggagaagtat gtagaagaca 1321 ccaaaataga cctatggtcc tacaatgcag aattgctggt ggctctagaa aatcaacata 1381 caattgactt aacagatgca gaaatgaata aattattcga gaagactaga cgccagttaa 1441 gagaaaacgc ggaagacatg ggaggtggat gtttcaagat ctaccacaaa tgtgataatg 1501 catgcattgg atcaataaga aatgggacat atgaccatta catatacaaa gatgaagcat 1561 taaacaaccg atttcaaatc aaaggtgttg agttgaaatc aggctacaaa gattggatac 1621 tgtggatttc attcgccata tcatgcttct taatttgcgt tgttctattg ggtttcatta 1681 tgtgggcttg ccaaaaaggc aacatcagat gcaacatttg catttgagta aactgatagt 1741 taaaaacacc cttgtttcta ct DEFINITION Influenza A virus (A/equine/Kentucky/1/94(H3N8))
hemagglutinin precursor (HA) gene, complete cds.
ACCESSION L39914;

SEQ ID NO: 19

1 agcaaaagca ggggatattt ctgtcaatca tgaagacaac cattattttg atactactga

-continued

```
  61 cccattgggt ctacagtcaa aacccaacca gtggcaacaa cacagccaca ttatgtctgg

 121 gacaccatgc agtagcaaat ggaacattgg taaaaacaat aactgatgac caaattgagg

 181 tgacaaatgc tactgaatta gttcagagca tttcaatagg gaaaatatgc aacaactcat

 241 atagagttct agatggaaga aattgcacat taatagatgc aatgctagga gaccccccact

 301 gtgatgtctt tcagtatgag aattgggacc tcttcataga aagaagcagc gctttcagca

 361 attgctaccc atatgacatc cctgactatg catcgctccg gtccattgta gcatcctcag

 421 gaacattgga attcacagca gagggattca catggacagg tgtcactcaa aacggaagaa

 481 gtggagcctg caaaagggga tcagccgata gtttctttag ccgactgaat tggctaacaa

 541 aatctggaaa ctcttacccc acattgaatg tgacaatgcc taacaataaa aatttcgaca

 601 aactatacat ctgggggatt catcacccga gctcaaacca acagcaaaca gaattgtaca

 661 tccaagaatc aggacgagta acagtctcaa caaaaagaag tcaacaaacg ataatcccta

 721 atatcggatc tagaccgtgg gtcaggggtc aatcaggcag gataagcata tactggacca

 781 ttgtaaaacc tggagatatc ctaatgataa acagtaatgg caacttagtt gcaccgcggg

 841 gatattttaa attgaaaaca gggaaaagct ctgtaatgag atcagatgca cccatagaca

 901 tttgtgtgtc tgaatgtatt acaccaaatg gaagcatccc caacgacaaa ccatttcaaa

 961 atgtgaacaa agttacatat ggaaaatgcc ccaagtatat caggcaaaac actttaaagc

1021 tggccactgg gatgaggaat gtaccagaaa agcaaatcag aggaatcttt ggagcaatag

1081 cgggattcat agaaaacggc tgggaaggaa tggttgatgg gtggtatgga ttccgatatc

1141 aaaactcgga aggaacagga caagctgcag atctaaagag cactcaagca gccatcgacc

1201 agattaatgg aaaattaaac agagtgattg aaaggaccaa tgagaaattc catcaaatag

1261 agaaggaatt ctcagaagta gaagggagaa tccaggactt ggagaagtat gtagaagaca

1321 ccaaaataga cctatggtcc tacaatgcag aattgctggt ggctctagaa aatcaacata

1381 caattgactt aacagatgca gaaatgaata aattattcga gaagactaga cgccagttaa

1441 gagaaaacgc ggaagacatg ggaggtggat gtttcaagat ttaccacaaa tgtgataatg

1501 catgcattgg atcaataaga aatgggacat atgaccatta catatacaga gatgaagcat

1561 taaacaaccg atttcaaatc aaaggtgttg agttgaaatc aggctacaaa gattggatac

1621 tgtggatttc attcgccata tcatgcttct taatttgcgt tgttctattg ggtttcatta

1681 tgtgggcttg ccaaaaaggc aacatcagat gcaacatttg catttgagta aactgatagt

1741 taaaaacacc cttgtttcta ct
```

DEFINITION Influenza A virus (A/equine/Kentucky/1/81(H3N8)) nucleo-
protein (NP) gene, complete cds.
ACCESSION AY291288;

SEQ ID NO: 20

```
   1 agcaaaagca gggtagataa tcactcactg agtgacatca aagtcatggc gtctcaaggc

  61 accaaacgat cttatgagca gatggaaact ggtggggaac gccagaatgc aactgaaatc

 121 agagcatctg ttggaaggat ggtgggagga atcggccggt tctatgttca aatgtgtact

 181 gagcttaaac tcaacgacca tgaagggcgg ctgattcaga acagcataac aatagaaagg

 241 atggtacttt cggcattcga cgaaagaaga aacaagtacc tcgaggagca tcccagtgct

 301 gggaaagacc ccaagaaaac gggaggcccg atatacagaa ggagagatgg gaaatggatg

 361 agagaactca tcctccatga taaagaagaa atcatgagga tctggcgtca ggccaacaat

 421 ggtgaagacg ctactgctgg tcttactcat atgatgatct ggcactccaa tctcaatgac

 481 accacctacc aaagaacaag ggctcttgtt cgggctggga tggatcccag aatgtgctct
```

-continued

```
 541 ctgatgcaag gatcaactct cccacggaga tctggagctg ccggtgctgc agtgaagggt

 601 gttggaacaa tggtaatgga actcatcagg atgatcaaac gcgggataaa tgatcgaaac

 661 ttctggagag gtgaaaatgg tcgaagaacc agaattgctt atgaaagaat gtgcaacatc

 721 ctcaagggga aattccaaac agcagcacaa cgagcaatga tggaccaagt gagggagggc

 781 cgcaatcctg gaaatgctga gattgaggat ctcattttct tggcacgatc agcactcatt

 841 ctgagaggat cagtagccca taaatcatgc ctacctgcct gtgtttatgg ccttgcagta

 901 gccagtgggt atgactttga gaaagaggga tactctctgg ttggaattga tcctttcaaa

 961 ctactccaga acagccaaat tttcagtcta atcagaccga aagaaaatcc agcacacaag

1021 agccagctgg tgtggatggc atgccattct gcagcatttg aggacctgag agtttcgaat

1081 ttcattagag gaaccaaagt aatcccaaga ggacagttag caaccagggg agtgcaaatt

1141 gcttcaaatg aaaacatgga gacaatagat tctagcacac tcgaactgag gagcagatat

1201 tggggcaataa ggaccaggag tgggggggaac accagtcaac agagagcatc tgcaggacag

1261 ataagtgtgc aacccacttt ctcagtgcag agaaatcttc cctttgaaag agcaaccatt

1321 atggctgcat tcactggaaa cactgagggg aggacttccg acatgagaac ggaaatcata

1381 aggatgatgg aaaatgccag atcagaagat gtgtctttcc aggggcgggg agtcttcgag

1441 ctctcggacg aaaaggcaac gaacccgatc gtgccttcct ttgacatgag caatgaaggg

1501 tcttatttct tcggagacaa tgctgaggag tttgacagtt aaagaaaaat acccttgttt

1561 ctact
```

DEFINITION Influenza A virus (A/Equine/Kentucky/1/92(H3N8)) gene for hemagglutinin precursor, partial cds.
ACCESSION D30683;

SEQ ID NO: 21

```
   1 gtcaatcatg aagacaacca ttattttgat actactgacc cattgggtct acagtcaaaa

  61 cccaaccagt ggcaacaaca cagccacatt atgtctggga caccatgcag tagcaaatgg

 121 aacattggta aaaacaataa ctgatgacca aattgaggtg acaaatgcta ctgaattagt

 181 tcagagcatt tcaataggga aaatatgcaa caactcatat agggttctag atggaagaaa

 241 ttgcacatta atagatgcaa tgctaggaga cccccactgt gatgtctttc agtatgagaa

 301 ttgggacctc ttcatagaaa gaagcagcgc tttcagcaat tgctacccat atgacatccc

 361 tgactatgca tcgctccggt ccattgtagc atcctcagga acattagaat tcacagcaga

 421 gggattcaca tggacaggtg tcactcaaaa cggaggaagt ggagcctgca aaaggggatc

 481 agccgatagt ttctttagcc gactgaattg gctaacaaaa tctggaaact cttaccccac

 541 attgaatgtg acaatgccta acaataaaaa tttcgacaaa ctatacatct gggggattca

 601 tcacccgagc tcaaacaatg agcagacaaa attgtatatc caagaaacag gacgagtaac

 661 agtctcaaca aaaagaagtc aacaaacaat aatccctaac atcggatcta gaccgtgggt

 721 caggggtcaa tcaggcagga taagcatata ctggaccatt gtaaaacctg gagatatcct

 781 aatgataaac agcaatggca acttagttgc accgcgggga tattttaaat tgagaacagg

 841 gagaagctct gtaatgagat cagatgcacc catagacatt tgtgtgtctg aatgtattac

 901 accaaatgga agcatcccca acgacaaacc atttcaaaat gtgaacaaag ttacatatgg

 961 aaaatgcccc aaatatatca ggcaaaacac tttaaagctg gccactggga tgaggaatgt

1021 accagaaaag caaatcagag gaatctttgg agcaatagcg ggattcatag aaaacggctg

1081 ggaaggaatg gttgat
```

DEFINITION Influenza A virus (A/equine/Kentucky/1/97(H3N8)) hemagglutinin precursor (HA1) mRNA, partial cds.

-continued

ACCESSION AF197249;

SEQ ID NO: 22

```
   1 agcaaaagca ggggatattt ctgtcaatca tgaagacaac cattattttg atactactga
  61 cccattgggc ctacagtcaa aacccaatca gtggcaacaa cacagccaca ttgtgtctgg
 121 gacaccatgc agtagcaaat ggaacattgg taaaaacaat aactgatgat caaattgagg
 181 tgacaaatgc tactgaatta gttcagagca tttcaatggg gaaaatatgc aacaactcat
 241 atagagttct agatggaaga aattgcacat taatagatgc aatgctagga gacccccact
 301 gtgatgtctt tcagtatgag aattgggacc tctttataga aagaagcagc gctttcagca
 361 attgctaccc atatgacatc cctgactatg catcgctccg gtccattgta gcatcctcag
 421 gaacattgga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca agagcagaca aaattgtaca
 661 tccaagaatc aggacgagta acagtctcaa caaaaagaag tcaacaaaca ataatcccta
 721 acatcggatc tagaccgtgg gtcaggggtc aatcaggcag gataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatctc caacgacaaa ccattccaaa
 961 atgtgaacaa agttacatat ggaaaatgcc ccaagtatat caggcaaaac actttaaagc
1021 tggccactgg gatgaggaat gaaccagaaa agcaaatcag a
```

DEFINITION Influenza A virus (A/equine/Kentucky/1/96(H3N8))
hemagglutinin precursor (HA1) mRNA, partial cds.
ACCESSION AF197248;

SEQ ID NO: 23

```
   1 agcaaaagca ggggatattt ctgtcaatca tgaagacaac cattattttg atactactga
  61 cccattgggt ctacagtcaa aacccaacca gtggcaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagagttct agatggaaga aattgcacat taatagatgc aatgctagga gacccccact
 301 gtgatgtctt ccagtatgag aattgggacc tcttcataga aagaagcagc gctttcagca
 361 attgctaccc atatgacatc cctgactatg catcgctccg gtccattgta gcatcctcag
 421 gaacattaga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca aaagcagaca gaattgtaca
 661 tccaagaatc aggacgagta acagtctcaa caaaaagaag tcaacaaacg ataatcccta
 721 atatcggatc tagaccgtgg gttaggggtc aatcaggcag gataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag a
```

DEFINITION Influenza A virus (A/equine/Kentucky/9/95(H3N8))
hemagglutinin precursor (HA1) mRNA, partial cds.

-continued

ACCESSION AF197247;

SEQ ID NO: 24

```
   1 agcaaaagca ggggatattt ctgtcaatca tgaagacaac cattattttg atactactga
  61 cccattgggt ctacagtcaa aacccaacca gtggaaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagagttct agatggaaga aattgcacat taatagatgc aatgctagga gacccccact
 301 gtgatgtctt ccagtatgag aattgggacc tcttcataga aagaagcagc gctttcagca
 361 attgctaccc atatgacatc cctgactatg catcgctccg gtccattgta gcatcctcag
 421 gaacattgga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctggggggatt catcacccga gctcaaacca aaagcagaca gaattgtaca
 661 tccaagaatc aggacgagta acagtctcaa caaaaagaag tcaacaaacg ataatcccta
 721 atatcggatc tagaccgtgg gtcaggggtc aatcaggcag gataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag a
```

DEFINITION Influenza A virus (A/equine/Kentucky/1/98(H3N8))
hemagglutinin precursor (HA1) mRNA, partial cds.
ACCESSION AF197241;

SEQ ID NO: 25

```
   1 agcaaaagca ggggatattt ctgtcaatca tgaagacaac cattattttg atactactga
  61 cccattgggt ctacagtcaa aacccaacca gtggaaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 ataaagttct agatggaaga aattgcacat taatagatgc aatgctagga gacccccact
 301 gtgatgtctt ccagtatgag aattgggacc tcttcataga aagaagcagc gctttcagca
 361 attgctaccc atatgacatc cctgactatg catcgctccg gtccattgta gcatcctcag
 421 gaacattaga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca acagcagaca gaattgtaca
 661 tccaagaatc aggacgagta acagtctcaa caaaaagaag tcaacaaacg atagtcccta
 721 atatcggatc tagaccgtgg gttaggggtc aatcaggcag gataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat ataccagaaa agcaaatcag a
```

DEFINITION Influenza A virus (A/eq/Kentucky/81(H3N8)) hemagglutinin
mRNA, complete cds.

-continued

ACCESSION U58195;

SEQ ID NO: 26

```
   1 agcaaaagca ggggatactt tctgtcaatc atgaagacaa ccattatttt gatactactg
  61 acccattggg tctacagtca aaacccaacc agtggcaaca acacagccac actatgtctg
 121 ggacaccatg cagtagcaaa tggaacattg gtaaaaacaa taactgatga ccaaattgag
 181 gtgacaaatg ctactgaatt agttcagagc acttcaatag ggaaaatatg caacaaccca
 241 tatagggttc tagatggaag aaactgcaca ttaatagatg caatgctagg agatccccac
 301 tgtgatgttt ttcagtatga gaattgggac ctcttcatag aaagaagcag cgctttcagc
 361 aattgctacc catatgacat ccctgactat gcatcgctcc ggtctattgt ggcatcttca
 421 ggaacattag aattcacagc agagggattc acatggacag gtgtcactca aaacggagga
 481 agtggagcct gcagaagggg gtcagccgat agtttcttta gccgactgaa ttggctaaca
 541 aaatctggaa attcttaccc cacattgaat gtaacaatgc ctaacaataa caatttcgat
 601 aaactataca tctgggggat ccatcacccg agcacaaaca atgagcagac aaaattgtat
 661 atccaagaat cagggcgagt aacagtctca acaaaaagaa gtcaacaaac aataatcccc
 721 aacatcggat ctagaccgtg ggtcaggggt caatcaggca ggataagcat atattggacc
 781 attgtgaaac ctggagatat cctaatgata aacagtaatg gcaacttagt tgcaccgcgg
 841 ggatatttta aaatgcgaac agggaaaagc tctgtaatga gatcagatgc acccatagac
 901 acttgtgtgt ccgagtgtat tacaccaaat ggaagcatcc ccaacgacaa accatttcaa
 961 aatgtgaaca aagttacata tggaaaatgc cccaagtata tcaagcagaa tactttgaag
1021 ctggccactg ggatgaggaa tgtaccagaa aagcaaatca gaggaatctt tggagcaata
1081 gcgggattca tagaaaacgg ctgggaagga atggttgatg ggtggtatgg attccgatat
1141 cagaattcgg aaggaacagg acaagctgca gatctaaaga gcactcaagc agccatcgac
1201 cagatcaatg gaaaattgaa cagagtgatt gaaaggacca atgagaaatt ccatcaaata
1261 gagaaggaat tctcagaagt agaagggaga atccaggact tggagaagta tgtagaagac
1321 accaaaatag acctatggtc ctacaatgca gagttactgg tggctctaga aaatcaacat
1381 acgattgact taacagatgc agaaatgaat aaattattcg agaagactag gcgccagtta
1441 agagaaaacg cggaagacat ggggggtgga tgtttcaaga tttatcacaa atgtgataat
1501 gcatgcattg gatcaataag aaatgggaca tatgaccatt acatatacag agatgaagca
1561 ttaaacaacc gatttcaaat taaaggtgtt gaattgaaat caggctacaa agattggata
1621 ctgtggattt cattcgccat atcatgcttc ttaatttgcg ttgttctatt gggtttcatc
1681 atgtgggctt gccaaaaagg caacatcaga tgcaacattt gcatttgagt aaactgataa
1741 ttaaaaacac ccttgtttct act
```

DEFINITION Influenza A virus (A/equine/Kentucky/2/86(H3N8)) membrane protein M1 and membrane protein M2 genes, complete cds.

ACCESSION M63540;

SEQ ID NO: 27

```
   1 agcaaaagca ggtagatatt taaagatgag tcttctaacc gaggtcgaaa cgtacgttct
  61 ctctattgta ccatcaggcc ccctcaaagc cgagatcgcg cagagacttg aagatgtctt
 121 tgcagggaag aacaccgatc ttgaggcact catggaatgg ctaaagacaa gaccaatcct
 181 gtcacctctg actaaaggga ttttaggatt tgtgttcacg ctcaccgtgc ccagtgagcg
 241 aggactgcaa cgtagacgct ttgtccaaaa tgcccttagt ggaaacggag atccaaataa
 301 catggacaga gcagtaaaac tgtacaagaa gcttaaaaga gaaataacat tccatggggc
 361 aaaagaggtg gcactcagct attccactgg tgcactagcc agctgcatgg gactcatata
```

-continued 421 caacagaatg gggactgtga caaccgaagt ggcatttggc ctggtatgcg ccacatgtga 481 acagattgct gattcccagc atcgatctca caggcagatg gtgacaacaa ccaacccact 541 aatcagacat gaaaacagaa tggtactagc cagtaccaca gctaaaacca tggagcaggt 601 ggcagggtcg agtgagcagg cagcagaggc catggaggtt gctagtaagg ccaggcagat 661 ggtgcaggca atgaggacca ttgggaccca ccctagctcc agtgccggtt tgaaagatga 721 tcttcttgaa aatttgcagg cctaccagaa acggatggga gtgcaaatgc agcggttcaa 781 gtgatcctct cgttattgca gcaagtatca ttgggatctt gcacttgata ttgtggattc 841 ttgatcgcct tttcttcaaa ttcatttatc gtctccttaa atacggtttg aaaagagggc 901 cttctacgga aggagtacct gagtctatga gggaagaata tcggcaggaa cagcagaatg 961 ctgtggatgt tgacgatggt cattttgtca acatagagct ggagtaaaaa actaccttgt 1021 ttctact DEFINITION Influenza A virus isolate A/equine/Kentucky/76 non-structural protein, complete cds.
ACCESSION M80971;

SEQ ID NO: 28

1 agcaaaagca gggtgacaaa aacataatgg attccaacac tgtgtcaagc tttcaggtag 61 actgttttct ttggcatgtc cgcaaacgat ttgcagacca agaactgggt gatgccccat 121 tccttgaccg gcttcgccga gaccagaagt ccctaaaagg aagaggcagc actcttggtc 181 tggacatcga aacagccact cgtgcaggaa agcagatagt ggagcggatt ctggaagagg 241 agtcagatga ggcacttaaa atgaccattg cctctgttcc tgcttcacgc tacttaactg 301 acatgactct tgatgagatg tcaagagact ggttcatgct catgcccaag cagaaagtaa 361 caggctccct atgtataagg atggaccagg caatcatgga taagaacatc atactaaaag 421 caaactttag tgtgattttc gaaaggctgg agacactaat actacttaga gctttcaccg 481 aagaaggagc agtcgttggc gaaatttcac cattgccttc tcttccagga catactaatg 541 aggatgtcaa aaatgcaatt ggggtcctca tcggaggact taaatggaat gataacacag 601 ttagaatctc tgaaactcta cagagattcg cttggagaag cagtcatgag aatgggagac 661 cttcattccc tccaaagcag aaacgaaaaa tggcgagaac aattgagtca gaagtttgaa 721 gaaataaggt ggttgattga agaagtgcga catagattga aaaatacaga aaatagtttt 781 gaacaaataa catttatgca agccttacaa ctattgcttg aagtagaaca agagataaga 841 actttctcgt ttcagcttat ttaatgataa aaaacaccct tgtttctact DEFINITION Influenza A virus (A/eq/Kentucky/92(H3N8)) matrix proteins M1 and M2 (M) gene, complete cds.
ACCESSION AF001683;

SEQ ID NO: 29

1 atgagtcttc tgaccgaggt cgaaacgtac gttctctcta tcgtaccatc aggccccctc 61 aaagccgaga tcgcgcagag acttgaagat gtctttgcag ggaagaacac cgatcttgag 121 gcactcatgg aatggctaaa gacaagacca atcctgtcac ctctgactaa agggatttta 181 ggattcgtat tcacgctcac cgtgcccagt gagcgaggac tgcagcgtag acgctttgtc 241 caaaatgccc ttagtggaaa cggagatcca aacaacatgg acagagcagt aaaactgtac 301 aggaaactta aaagagaaat aacattccat ggggcaaaag aggtggcact cagctattcc 361 actggtgcac tagccagctg catgggactc atatacaaca gaatgggaac tgtgacaacc 421 gaagtggcat ttggcctagt atgcgccaca tgtgaacaga ttgctgattc ccagcatcga 481 tctcacaggc agatggtgac aacaaccaac ccattaatca gacatgaaaa cagaatggta 541 ttagccagta ccacggctaa agccatggag cagatggcag ggtcgagtga gcaggcagca -continued 601 gaggccatgg aggttgctag taaggctagg cagatggtac aggcaatgag gaccattggg 661 acccacccta gctccagtgc cggtttgaaa aatgatctcc ttgaaaattt gcaggcctac 721 cagaaacgga tgggagtgca aatgcagcga ttcaagtgat cctctcgtta ttgcagcaag 781 tatcattggg atcttgcact tgatattgtg gattcttgat cgccttttct tcaaattcat 841 ttatcgtcgc cttaaatacg ggttgaaaag agggccttct acggaaggag tacctgagtc 901 tatgagggaa gaatatcggc aggaacagca gaatgctgtg gatgttgacg atggtcattt 961 tgtcaacata gagctggagt aa DEFINITION Influenza A virus (A/eq/Kentucky/81(H3N8)) matrix
proteins M1 and M2 (M) gene, complete cds.
ACCESSION AF001676;

SEQ ID NO: 30

1 atgagtcttc taaccgaggt cgaaacgtac gttctctcta tcgtaccatc aggccccctc 61 aaagccgaga tcgcgcagag acttgaagat gtctttgcag ggaagaacac cgatcttgag 121 gcactcatgg aatggctaaa gacaagacca atcctgtcac ctctgactaa agggatttta 181 ggatttgtgt tcacgctcac cgtgcccagt gagcgaggac tgcagcgtag acgctttgtc 241 caaaatgccc ttagtggaaa cggagatcca aacaacatgg acagagcagt aaaactgtac 301 aggaagctta aaagagaaat aacattccat ggggcaaaag aggtggcact cagctattcc 361 actggtgcac tagccagctg catgggactc atatacaaca gaatggggac tgtgacaacc 421 gaagtggcat ttggcctggt atgcgccaca tgtgaacaga ttgctgattc ccagcatcga 481 tctcacaggc agatggtgac aacaaccaac ccactaatca gacatgaaaa cagaatggta 541 ctagccagta ccacagctaa agccatggaa cagatggcag ggtcgagtga gcaggcagca 601 gaggccatgg aggttgctag taaggccagg cagatggtac aggcaatgag gaccattggg 661 acccacccta gctccagtgc cggtttgaaa gatgatcttc ttgaaaattt gcaggcctac 721 cagaaacgga tgggagtgca aatgcagcga ttcaagtgac cctctcgtta ttgcagcaag 781 tatcattggg atcttgcact tgatattgtg gattcttgat cgccttttct tcaaattcat 841 ttatcgtcgc cttaaatacg gtttgaaaag agggccttct acggaaggag tacctgagtc 901 tatgagggaa gaatatcggc aggaacagca gaatgctgtg gatgttgacg atggtcattt 961 tgtcaacata gagctggagt aa DEFINITION Influenza A virus (A/eq/Kentucky/92(H3N8)) nonstructural
proteins NS1 and NS2 (NS) gene, complete cds.
ACCESSION AF001671;

SEQ ID NO: 31

1 atggattcca acactgtgtc aagctttcag gtagactgtt ttctttggca tgtccgcaaa 61 cgattcgcag accaagaact gggtgatgcc ccattccttg accggcttcg ccgagaccag 121 aagtccctaa aaggaagagg tagcactctt ggtctggaca tcgaaacagc cactcgtgca 181 ggaaagcaga tagtggagca gattctggaa gaggaatcag atgaggcact taaaatgacc 241 attgcctctg ttcctgcttc acgctactta actgacatga ctcttgatga gatgtcaaga 301 gactggttca tgctcatgcc caagcagaaa gtaacaggct ccctatgtat aagaatggac 361 caggcaatca tggataagaa catcatactt aaagcaaact ttagtgtgat tttcgaaagg 421 ctggaaacac taatactact tagagccttc accgaagaag gagcagtcgt tggcgaaatt 481 tcaccattgc cttctcttcc aggacatact aatgaggatg tcaaaaaatgc aattggggtc 541 ctcatcggag gacttaaatg gaatgataat acggttagaa tctctgaaac tctacagaga 601 ttcgcttgga gaagcagtca tgagaatggg agaccttcat tccctccaaa gcagaaacga 661 aaaatggaga gaacaattga gccagaagtt tgaagaaata agatggttga ttgaagaagt -continued 721 gcgacataga ttgaaaaata cagaaaatag ttttgaacaa ataacattta tgcaagcctt 781 acaactattg cttgaagtag aacaagagat aagaactttc tcgtttcagc ttatttaa DEFINITION Influenza A virus (A/eq/Kentucky/1/88(H3N8)) nonstructural proteins NS1 and NS2 (NS) gene, complete cds.
ACCESSION AF001664;

SEQ ID NO: 32

1 atggattcca acactgtgtc aagctttcag gtagactgtt ttctttggca tgtccgcaaa 61 cgatttgcag accaagaact gggtgatgcc ccattccttg accggcttcg ccgagaccag 121 aagtccctaa aaggaagagg cagcactctt ggtctggaca tcgaaacagc cactcgtgca 181 ggaaagcaga tagtggagca gattctggaa gaggaatcag atgaggcact taaaatgacc 241 attgcctctg ttcctgcttc acgctactta actgacatga ctcttgatga gatgtcaaga 301 gactggttca tgctcatgcc caagcagaaa gtaacaggct ccctatgtat aaggatggac 361 caggcaatca tggataagaa catcatacta aaagcaaact ttagtgtgat tttcgaaagg 421 ctggagacac taatactact tagagccttc accgaagaag gagcagtcgt tggcgaaatt 481 tcaccattgc cttctcttcc aggacatact aatgaggatg tcaaaaatgc aattggggtc 541 ctcatcggag gacttaaatg gaatgataat acagttagag tctctgaaac tctacagaga 601 ttcgcttgga gaagcagtca tgagaatggg agaccttcat tccctccaaa gcagaaacga 661 aaaatggcga gaacaattga gccagaagtt tgaagaaata agatggttga ttgaagaagt 721 gcgacataga ttgaaaaata cagaaaatag ttttgaacaa ataacattta tgcaagcctt 781 acaactattg cttgaagtag aacaagagat aagaactttc tcgtttcagc ttatttaa DEFINITION Influenza A/equine/Kentucky/2/86(H3N8) nucleoprotein (seg 5) mRNA, complete cds.
ACCESSION M30751;

SEQ ID NO: 33

1 agcaaaagca gggtagataa tcactcactg agtgacatca aagtcatggc gtctcaaggc 61 accaaacgat cttatgagca gatggaaact ggtggggaac gccagaatgc aactgaaatc 121 agagcatctg tcggaaggat ggtgggagga atcggccggt tctatgttca gatgtgtact 181 gagcttaaac tcaacgacca tgaagggcgg ctgattcaga acagcataac aatagaaagg 241 atggtacttt cggcattcga cgaaagaaga aacaagtacc tcgaggagca tcccagtgct 301 gggaaagacc ccaagaaaac gggaggcccg atatacagaa ggaaagatgg gaaatggatg 361 agagaactca tcctccatga taaagaagaa atcatgagga tctggcgtca ggccaacaat 421 ggtgaagacg ctactgctgg tcttactcat atgatgatct ggcactccaa tctcaatgac 481 accacatacc aaagaacaag ggctcttgtt cgggctggga tggatcccag aatgtgctct 541 ctgatgcaag gatcaaccct cccacggaga tctggagctg ccggtgctgc agtaaaaggt 601 gttggaacaa tggtaatgga actcatcagg atgatcaaac gcgggataaa tgatcgaaat 661 ttctggagag gtgaaaatgg tcgaagaacc agaattgctt atgaaagaat gtgcaatatc 721 ctcaaaggga aattccaaac agcagcacaa cgggcaatga tggaccaagt gagggagggc 781 cgcaatcctg gaaatgctga gattgaggat ctcattttct tggcacgatc agcactcatt 841 ttgagaggat cagtagccca taaatcatgc ctacctgcct gtgtttatgg ccttgcagta 901 gccagtgggt atgactttga gaaggaagga tactctctgg ttggaattga tcctttcaaa 961 ctactccaga acagccaaat tttcagtcta atcagaccga aagaaaatcc agcacacaag 1021 agccagttgg tgtggatggc atgccattct gcagcatttg aggacctgag agttttgaat 1081 ttcattagag gaaccaaagt aatcccaaga ggacagttag caaccagagg agtgcaaatt 1141 gcttcaaatg aaaacatgga gacaatagat tctagcacac tcgaactgag gagcagatat -continued 1201 tgggcaataa ggaccaggag tggagggaac accagtcaac agagagcatc tgcaggacag 1261 ataagtgtgc aacccacttt ctcagtgcag agaaatcttc cctttgaaag agcaaccatt 1321 atggctgcat tcactgggaa cactgagcgg aggacttccg acatgagaac ggaaatcata 1381 aggatgatgg aaaatgccag atcagaagat gtgtctttcc aggggcgggg agtcttcgag 1441 ctctcggacg aaaaggcaac gaacccgatc gtgccttcct ttgacatgag caatgaaggg 1501 tcttatttct tcggagacaa tgctgaggag tttgacagtt aaagaaaaat acccttgttt 1561 ctact DEFINITION Influenza A/Equine/Kentucky/2/86(H3N8), PB2 polymerase, complete cds.
ACCESSION M73526 M36049;

SEQ ID NO: 34

1 agcaaaagca ggtcaaatat attcaatatg gagagaataa aagaactgag agatctaatg 61 tcacagtccc gcacccgcga gatactaaca aaaactactg tggaccatat ggccataatc 121 aagaaataca catcaggaag acaagagaag aaccccgcac ttaggatgaa gtggatgatg 181 gcaatgaaat acccaattac agcagataag aggataatgg aaatgattcc tgagagaaat 241 gaacaggggc aaaccctttg gagcaaaacg aacgatgctg gctcagaccg cgtaatggta 301 tcacctctgg cagtgacatg gtggaatagg aatggaccaa caacgagcac aattcattat 361 ccaaaagtct acaaaactta ttttgaaaaa gttgaaaggt taaaacacgg aacctttggc 421 cccgttcatt ttaggaatca agtcaagata agacggagag ttgacgtaaa ccctggtcac 481 gcggacctca gtgccaaaga agcacaagat gtgatcatgg aagttgtttt cccaaatgaa 541 gtgggagcca gaattctaac atcggaatca caactaacaa taaccaaaga gaaaaaagaa 601 gaacttcagg actgcaaaat tgccccottg atggtagcat acatgctaga aagagagttg 661 gtccgaaaaa caaggttcct cccagtggct ggcggaacaa gcagtgtata cattgaggtg 721 ttgcatctga ctcagggaac gtgctgggaa caaatgtaca ccccaggagg agaagttaga 781 aacgatgaca ttgatcaaag tttaattatt gctgcccgga acatagtgaa aagagcgaca 841 gtatcagcag atccactagc atccctgctg gagatgtgcc acagtacaca gattggtgga 901 ataaggatgg tagacatcct taagcagaat ccaacagagg aacaagctgt ggatatatgc 961 aaagcagcaa tggggttaag aattagctca tcattcagct ttggtggatt cacctttaag 1021 agaacaagtg gatcatcagt caagagagaa gaagaaatgc ttacgggcaa ccttcaaaca 1081 ttgaaaataa gagtgcatga gggctatgaa gaattcacaa tggtcggaag aagagcaaca 1141 gccattctca gaaagacaac cagaagattg attcaattga tagtaagtgg gagagatgaa 1201 cagtcaattg ctgaagcaat aattgtagcc atggtgtttt cgcaagaaga ttgcatgata 1261 aaagcagttc gaggcgattt gaacttcgtt aatagagcaa atcagcgctt gaaccccatg 1321 catcaactct tgaggcattt ccaaaaggat gcaaaagtgc ttttccagaa ttgggggatt 1381 gaacccatcg acaatgtgat gggaatgatc ggaatattgc ccgacatgac cccaagcacc 1441 gagatgtcat tgagaggagt gagagtcagc aaaatgggag tggatgagta ctccagcact 1501 gagagagtgg tggtgagcat tgaccgtttt ttaagagttc gggatcaaag gggaaacata 1561 ctactgtccc ctgaagaggt cagtgaaaca caaggaacgg aaaagctgac aataatttat 1621 tcatcatcaa tgatgtggga gattaatggt cccgagtcag tgttggtcaa tacttatcaa 1681 tggatcatca gaaactggga aattgtgaaa attcaatggt cacaggatcc cacaatgtta 1741 tacaataaga tagaatttga gccattccag tccctggtcc ctagggccac cagaagccaa 1801 tacagcggtt tcgtaaggac cctgtttcag caaatgcgag atgtacttgg aacatttgac -continued 1861 actgctcaaa taataaaact cctccctttt gccgctgctc ctccggaaca gagtagaatg 1921 cagttctctt ctttgactgt taatgtaaga ggatcgggaa tgaggatact tgtaagaggc 1981 aattccccag tgttcaacta caacaaagcc actaagaggc tcacagtcct cggaaaggat 2041 gcaggtgcgc ttactgaaga cccagatgaa ggtacggctg gagtagaatc tgctgttctg 2101 agagggtttc tcatcttagg taaagaaaac aagagatatg gcccagcact aagcatcaat 2161 gaactgagca aacttacaaa aggggagaaa gctaatgtgc taattgggca aggggacgtg 2221 gtgttggtaa tgaaacggaa acgtgactct agcatactta ctgacagtca gacagcgacc 2281 aaaaggattc ggatggccat caattagtgt tgaattgttt aaaaacgacc ttgtttctac 2341 t DEFINITION Influenza A/equine/Kentucky/1/87(H3N8) hemagglutinin (HA)
RNA (seg. 4), complete cds.
ACCESSION M24728 J04336;

SEQ ID NO: 35

1 agcaaaagca ggggatattt ctgtcaatca tgaagacaac cattgttttg atactactga 61 cccattgggt ctacagtcaa aacccaacca gtggcaacaa cacagccaca ttatgtctgg 121 gacaccatgc agtagcaaat ggaacactgg taaaaacaat aactgatgac cagattgagg 181 tgacaaatgc tactgaatta gttcagagca tttcaatagg gaaaatatgc aacaactcat 241 atagggttct agatggaaga aattgcacat taatagatgc aatgctagga gacccccact 301 gtgatgtttt tcngtatgag aattgggacc tcttcataga aagaagcagc gctttcagca 361 attgctaccc atatgacatc cctgactatg catcgctccg gtctattgtg gcatcctcag 421 gaacattaga attcacagca gagggattca catggacagg tgtcactcaa aacggaagaa 481 gtggagcctg caaaagggga tcagccgata gtttctttag ccgactgaat tggctaacaa 541 aatctggaaa ttcttacccc acattgaatg tgacaatgcc taacaataac aatttcgata 601 aactatacat ctgggggatt catcacccga gctcaaacaa tgagcagaca aaattgtata 661 tccaagaatc aggacgagta acagtctcaa caaaaagaag tcaacaaaca ataatcccca 721 acatcggatc tagaccgtgg gtcaggggtc aatcaggcag gataagcata tattggacca 781 ttgtgaaacc tggagatatc ctaatgataa acagtaatgg caacttagtt gcaccgcggg 841 gatatttcaa attgagaaca gggaaaagct ctgtaatgag atcagatgca cccatagaca 901 cttgtgtgtc tgaatgtatt acaccaaatg gaagcatccc caacgacaaa ccattccaaa 961 atgtgaacaa agttacatat ggaaaatgcc ccaagtatat caggcaaaac actttgaagc 1021 tggccactgg gatgaggaat gtaccagaaa agcaaatcag aggaatcttt ggagcaatag 1081 cgggattcat agaaaacggc tgggaaggaa tggttgatgg gtggtatgga ttccgatatc 1141 aaaattcgga aggaacagga caagctggag atctaaagag cactcaagca gccatcgacc 1201 agatcaatgg aaaattaaac agagtgattg aaaggaccaa tgagaaattc catcaaatag 1261 agaaggaatt ctcagaagta gaagggagaa tccaggactt ggagaagtat gtagaagaca 1321 ccaaaataga cctatggtcc tacaatgcag aattgctggt ggctctagaa aatcaacata 1381 caattgactt aacagatgca gaaatgaata aattattcga gaagactagg cgccagttaa 1441 gagaaaacgc ggaagacatg ggaggtggat gtttcaggat ttaccacaaa tgtgataatg 1501 catgcattgg atcaataaga aatgggacat atgaccatta catatacaga gatgaagcat 1561 taaacaaccg atttcaaatt aaaggtgttg agttgaaatc aggctacaaa gattggatac 1621 tgtggatttc attcgccata tcatgcttct taatttgcgt tgttctattg ggtttcatta 1681 tgtgggcttg ccaaaaaggc aacatcagat gcaacatttg catttgagta aactgatagt -continued

```
1741 taaaaacacc cttgtttcta ct
```

DEFINITION Influenza A/equine/Kentucky/2/86(H3N8) hemagglutinin (HA)
RNA (seg. 4), complete cds.
ACCESSION M24727 J04336;

SEQ ID NO: 36

```
   1 agcaaaagca ggggatattt ctgtcaatca tgaagacaac cattattttg atactactga

  61 cccattgggt ctacagtcaa aacccaacca gtggcaacaa cacagccaca ttatgtctgg

 121 gacaccatgc agtagcaaat ggaacattgg taaaaacaat aactgatgac caaattgagg

 181 tgacaaatgc tactgaatta gttcagagca tttcaatagg gaaaatatgc aacaactcat

 241 atagggttct agatggaaga aattgcacat taatagatgc aatgctagga gaccccccact

 301 gtgatgtttt tcngtatgag aattgggacc tcttcataga aagaagcagc gcttccagca

 361 attgctaccc atatgacatc cctgactatg catcgctccg gtctattgtg gcatcctcag

 421 gaacattaga attcacagca gagggattca catggacagg tgtcactcaa aacggaagaa

 481 gtggagcctg caaaagggga tcagccgata gtttctttag ccgactgaat tggctaacaa

 541 aatctggaaa ttcttacccc acattgaatg tgacaatgcc taacaataac aatttcgata

 601 agctatacat ctgggggatc catcacccga gctcaaacaa tgagcagaca aaattgtata

 661 tccaagaatc aggacgagta acagtctcaa caaaaagaag tcaacaaaca ataatcccca

 721 acatcggatc tagaccgtgg gtcaggggtc aatcaggcag gataagcata tattggacca

 781 ttgtgaaacc tggagatatc ctaataataa acagtaatgg caacttagtt gcaccgcggg

 841 gatatttcaa attgcgaaca gggaaaagct ctgtaatgag atcagatgca cccatagaca

 901 cttgtgtgtc tgaatgtatt acaccaaatg gaagcatccc caacgacaaa ccatttcaaa

 961 atgtgaacaa agttacatat ggaaaatgcc ccaagtatat caggcaaaac actttgaagc

1021 tggccactgg gatgaggaat gtaccagaaa agcaaatcag aggaatcttt ggagcaatag

1081 cgggattcat agaaaacggc tgggaaggaa tggttgatgg gtggtatgga ttccgatatc

1141 aaaactcgga aggaacagga caagctggag atctaaagag cactcaagca gccatcgacc

1201 agatcaatgg aaaattgaac agagtgattg aaaggaccaa tgagaaattc catcaaatag

1261 agaaggaatt ctcagaagta gaagggagaa tccaggactt ggagaagtat gtagaagaca

1321 ccaaaataga cctatggtcc tacaatgcag agttgctggt ggctctagaa aatcaacata

1381 caattgactt aacagatgca gaaatgaata aactattcga gaagactagg cgccagttaa

1441 gagaaaacgc ggaagacatg ggaggtggat gtttcaagat ttatcacaaa tgtgataatg

1501 catgcattgg atcaataaga aatgggacat atgaccatta catatacaga gatgaagcat

1561 taaacaaccg atttcaaatt aaaggtgtag agctgaaatc aggctacaaa gattggatac

1621 tgtggatttc attcgccata tcatgcttct taatttgcgt tgttctattg ggtttcatta

1681 tgtgggcttg ccaaaaaggc aacatcagat gcaacatttg catttgagta aactgatagt

1741 taaaaacacc cttgtttcta ct
```

EXAMPLE 5

Newmarket Equine Influenza Nucleotide Sequences

DEFINITION Influenza A virus (A/equine 2/Suffolk/89(H3N8)) NS1 gene.
ACCESSION X80060;

SEQ ID NO: 37

```
   1 atggattcca acactgtgtc aagctttcag gtagactgtt ttctttggca tgtccgcaaa
```

-continued

```
  61 cgatttgcag accaagaact gggtgatgcc ccattccttg accggcttcg ccgagaccag

 121 aagtccctaa aaggaagagg tagcactctt ggtctggaca tcgaaacagc cactcgtgca

 181 ggaaagcaga tagtggagca gattctggaa gaggaatcag atgaggcatt taaaatgacc

 241 attgcctctg ttcctgcttc acgctactta actgacatga ctcttgatga gatgtcaaga

 301 gactggttca tgctcatgcc caagcagaaa gtaacaggct ccctatgtat aagaatggac

 361 caggcaatca tggataagaa catcatactt aaagcaaact ttagtgtgat tttcgaaagg

 421 ctggagacac taatactact cagggccttc accgaagaag gagcagtcgt tggcgaaatt

 481 tcaccattgc cttctcttcc aggacatact aatgaggatg tcaaaaatgc aattggggtc

 541 ctcatcggag gacttaaatg gaatgataat acggttagag tctctgaaac tctacagaga

 601 ttcgcttgga gaagcagtca tgagaatggg agaccttcat tccctccaaa gcagaaacga

 661 aaaatggaga gaacaattga gtcagaagtt tga
```

DEFINITION Influenza A virus (A/eq/Newmarket/93/(H3N8)) HAI gene for
HAY subunit of haemagglutinin, genomic RNA.
ACCESSION X85089;

SEQ ID NO: 38

```
   1 atgaagacaa ccattatttt gatactactg acccattggg tctacagtca aaacccaacc

  61 agtggcaaca acacagccac attatgtctg ggacaccatg cagtagcaaa tggaacattg

 121 gtaaaaaacaa taactgatga ccaaattgag gtgacaaatg ctactgaatt agtccagagc

 181 atttcaatag ggaaaatatg caacaactca tatagggttc tagatggaag aaattgcaca

 241 ttaatagatg caatgctagg agacccccat tgtgatgatt ttcagtatga gaattgggac

 301 ctcttcatag aaagaagcag cgctttcagc aattgctacc catatgacat ccctgactat

 361 gcatcgctcc ggtccattgt agcatcctca ggaacattag aattcacagc agaggggttc

 421 acatggacag gtgtcactca aaacggagga agtggagcct gcaaaagggg atcagccgat

 481 agtttcttta gccgactgaa ttggctaaca aaatctggaa attcttaccc catattgaat

 541 gtgacaatgc ctaacaataa aaatttcgat aaactataca tctgggggat tcatcacccg

 601 agctcaaaca aagagcagac aaaattatat atccaagaat caggacgagt aacagtctca

 661 acagaaagaa gtcaacaaac agtaatccct aacatcggat ctaggccgtg ggtcaggggt

 721 caatcaggca ggataagcat atactggacc attgtaaaac ctggagatat tctaatgata

 781 aacagtaatg gcaacttagt tgcaccgcgg ggatatttta aattgagaac agggaaaagc

 841 tctgtaatga gatcagatgc actcatagac acttgtgtgt ctgaatgtat tacaccaaat

 901 ggaagcatcc ccaacgacaa accatttcaa aatgtgaaca aaattacata tggaaaatgc

 961 cccaagtata tcaggcaaaa cactttaaag ctggccactg ggatgaggaa tgtaccagaa

1021 aagcaaatca ga
```

DEFINITION Influenza A virus (A/eq/Newmarket/93/(H3N8)) HAI gene for
HAY subunit of haemagglutinin, genomic RNA.
ACCESSION X85088;

SEQ ID NO: 39

```
   1 atgaagacaa ccattatttt gatactactg acccattggg tctacagtca aaacccaacc

  61 agtggcaaca acacagccac attatgtctg ggacaccatg cagtagcaaa tggaacattg

 121 gtaaaaacaa taactgatga ccaaattgag gtgacaaatg ctactgaatt agttcagagc

 181 atttcaatag ggaaaatatg caacaactca tatagagttc tagatggaag aaattgcaca

 241 ttaatagatg caatgctagg agacccccac tgtgatgtct ttcagtatga gaattgggac

 301 ctcttcatag aaagaagcag cgctttcagc aattgctacc catatgacat ccctgactat

 361 gcatcgctcc ggtccattgt agcatcctca ggaacattgg aattcacagc agagggattc
```

-continued

```
 421 acatggacag gtgtcactca aaacggaaga agtggagcct gcaaaagggg atcagccgat

 481 agtttcttta gccgactgaa ttggctaaca aaatctggaa actcttaccc cacattgaat

 541 gtgacaatgc ctaacaataa aaatttcgac aaactataca tctgggggat tcatcacccg

 601 agctcaaacc aacagcagac agaattgtac atccaagaat caggacgagt aacagtctca

 661 acaaaaagaa gtcaacaaac gataatccct aatatcggat ctagaccatg ggtcaggggt

 721 caatcaggca ggataagcat atactggacc attgtaaaac ctggagatat cctaatgata

 781 aacagtaatg gcaacttagt tgcaccgcgg ggatatttta aattgaaaac agggaaaagc

 841 tctgtaatga gatcagatgc acccatagac atttgtgtgt ctgaatgtat tacaccaaat

 901 ggaagcatcc ccaacgacaa accatttcaa aatgtgaaca aagttacata tggaaaatgc

 961 cccaagtata tcaggcaaaa cactttaaag ctggccactg ggatgaggaa tgtaccagaa

1021 aagcaaatca ga
```

DEFINITION Influenza A virus (A/eq/Sussex/89/(H3N8)) HAI gene for HAY subunit of haemagglutinin, genomic RNA.
ACCESSION X85090;

SEQ ID NO: 40

```
   1 atgaagacaa ccattatttt gatactactg acccattggg tctacagtca aaacccaacc

  61 agtggcaaca acacagccac attatgtctg ggacaccatg cagtagcaaa tggaacattg

 121 gtaaaaacaa taactgatga ccaaattgag gtgacaaatg ctactgaatt agttcagagc

 181 atttcaatag ggaaaatatg caacaactca tatagggttc tagatggaag aaattgcaca

 241 ttaatagatg caatgctagg agacccccac tgtgatgttt ttcagtatga gaattgggac

 301 ctcttcatag aaagaagcag cgctttcagc aattgctacc catatgacat ccctgactat

 361 gcatcgctcc ggtccattgt agcatcctca ggaacattag aattcacagc agagggattc

 421 acatggacag gtgtcactca aaacggaaga agtggagcct gcaaaagggg atcagccgat

 481 agtttcttta gccgactgaa ttggctaaca aaatctggaa attcttaccc catattgaat

 541 gtgacaatgc ctaacaataa aaatttcgat aaactataca tctgggggat tcatcacccg

 601 agctcaaaca aagagcagac aaaattgtat atccaagaat caggacgagt aacagtctca

 661 acagaaagaa gtcaacaaac agtaatccct aacatcggat ctagaccgtg ggtcaggggt

 721 caatcaggca ggataagcat atactggacc attgtaaaac ctggagatat tctaatgata

 781 aacagtaatg gcaacttagt tgcaccgcgg ggatatttta aattgagaac agggaaaagc

 841 tctgtaatga gatcagatgc actcataggc acttgtgtgt ctgaatgtat tacaccaaat

 901 ggaagcatcc ccaacgacaa accatttcaa aatgtgaaca aagttacata tggaaaatgc

 961 cccaagtata tcaggcaaaa cactttaaag ctggccactg ggatgaggaa tgtaccagaa

1021 aagcaaatca ga
```

DEFINITION Influenza A virus (A/eq/Lambourn/92/(H3N8)) HAI gene for HAY subunit of haemagglutinin, genomic RNA.
ACCESSION X85087;

SEQ ID NO: 41

```
   1 atgaagacaa ccattatttt gatactactg acccattggg tctacagtca aaacccaacc

  61 agtggcaaca acacagccac attatgtctg ggacaccatg cagtagcaaa tggaacattg

 121 gtaaaaacaa taactgatga ccaaattgag gtgacaaatg ctactgaatt agttcagagc

 181 atttcaatag ggaaaatatg caacaactca tatagggttc tagatggaag aaattgcaca

 241 ttaatagatg caatgctagg agacccccat tgtgatgatt ttcagtatga gaattgggac

 301 ctcttcatag aaagaagcag tgctttcagc aattgctacc catatggcat ccctgactat

 361 gcatcgctcc ggtccattgt agcatcctca ggaacattag aattcacagc agaggggttc
```

-continued 421 acatggacag gtgtcactca aaacggaaga agtggagcct gcaaaagggg atcagccgat 481 agtttcttta gccgactcaa ttggctaaca aaatctggaa attcttaccc catattgaat 541 gtgacaatgc ctaacaataa aaatttcgat aaactataca tctgggggat tcatcacccg 601 agctcaaaca aagagcagac aaaattatat atccaagaat caggacgagt aacagtctca 661 acagaaagaa gtcaacaaac agtaatccct aacatcggat ctaggccgtg ggtcaggggt 721 caatcaggca ggataagcat atactggacc attgtaaaac ctggagatat tctaatgata 781 aacaataatg gcaacttagt tgcaccgcgg ggatatttta aattgagaac agggaaaagc 841 tctgtaatga gatcagatgc actcatagac acttgtgtgt ctgaatgtat tacaccaaat 901 ggaagcatcc ccaacgacaa accatttcaa aatgtgaaca aagttacata tggaaaatgc 961 cccaagtata tcaggcaaaa cactttaaag ctggccactg ggatgaggaa tataccagaa 1021 aagcaaatca ga DEFINITION Influenza A virus (A/eq/Ella/89/(H3N8)) HAI gene for HAY
subunit of haemagglutinin, genomic RNA.
ACCESSION X85086;

SEQ ID NO: 42

1 atgaagacaa ccattatttt gatactactg acccattggg tctacagtca aaacccaacc 61 agtggcaaca acacagccac attatgtctg ggacaccatg cagtagcaaa tggaacattg 121 gtaaaaacaa taactgatga ccaaattgag gtgacaaatg ctactgaatt agttcagagc 181 atttcaatag ggaaaatatg caacaactca tatagggttc tagatggaag aaattgcaca 241 ttaatagatg caatgctagg agacccccac tgtgatgttt ttcagtatga gaattgggac 301 ctcttcatag aaagaagcag cgctttcagc aattgctacc catatgacat ctctgactat 361 gcatcgctcc ggtccattgt agcatcctca ggaacattag aattcacagc agagggattc 421 acatggacag gtgtcactca aaacggaaga agtggagcct gcaaaagggg atcagccgat 481 agtttcttta gccgactgaa ttggctaaca aaatctggaa attcttaccc catattgaat 541 gtgacaatgc ctaacaataa aaatttcgat aaactataca tctgggggat tcatcacccg 601 agctcaaaca aagagcagac aaaattgtat atccaagaat caggacgagt aacagtctca 661 acagaaagaa gtcaacaaac agtaatccct aacatcggat ctagaccgtg ggtcaggggt 721 caatcaggca ggataagcat atactggacc attgtaaaac ctggagatat tctaatgata 781 aacagtaatg gcaacttagt tgcaccgcgg ggatatttta aattgagaac agggaaaagc 841 tctgtaatga gatcagatgc acccataggc acttgtgtgt ctgaatgtat tacaccaaat 901 ggaagcatcc ccaacgacaa accatttcaa aatgtgaaca aagttacata tggaaaatgc 961 cccaagtata tcaggcaaaa cactttaaag ctggccactg ggatgaggaa tgtaccagaa 1021 aagcaaatca ga DEFINITION Influenza A virus (A/eq/Arundel/91/(H3N8)) HAI gene for
HAY subunit of haemagglutinin, genomic RNA.
ACCESSION X85085;

SEQ ID NO: 43

1 atgaagacaa ccattatttt gatactactg acccattggg tctacagtca aaacccaacc 61 agtggcaaca acacagccac attatgtctg ggacaccatg cagtagcaaa tggaacattg 121 gtaaaaacaa taactgatga ccaaattgag gtgacaaatg ctactgaatt agttcagagc 181 atttcaatag ggaaaatatg.caacaactca tatagagttc tagatggaag aaattgcaca 241 ttaatagatg caatgctagg agacccccac tgtgatgtct ttcagtatga gaattgggac 301 ctcttcatag aaagaagcag cgctttcagc aattgctacc catatgacat ccctgactat 361 gcatcgctcc ggtccattgt agcatcctca ggaacattag aattcacagc agagggattc -continued

```
 421 acatggacag gtgtcactca aaacggaaga agtggagcct gcaaaagggg atcagccgat
 481 agtttcttta gccgactgaa ttggctaaca aaatctggaa attcttaccc catattgaat
 541 gtgacaatgc ctaacaataa aaatttcgat aaactataca tctgggggat tcatcacccg
 601 agctcaaaca aagagcagac aaaattgtac atccaagaat caggacgagt aacagtctca
 661 acaaaaagaa gtcaacaaac aataatccct aacatcggat ctagaccgtg ggtcaggggt
 721 caatcaggca ggataagcat atactggacc attgtaaaac ctggagatat cctaatgata
 781 aacagtaatg gcaacttagt tgcaccgcgg ggatatttta aattgagaac agggaaaagc
 841 tctgtaatga gatcagatgc acccatagac atttgtgtgt ctgaatgtat tacaccaaat
 901 ggaagcatcc ccagcgacaa accatttcaa aatgtaaaca aagttacata tggaaaatgc
 961 cccaagtata tcaggcaaaa cactttaaag ctggccactg ggatgaggaa tgtaccagaa
1021 aagcaaatca ga
```

DEFINITION Influenza A virus (A/equine/Suffolk/89(H3N8)) HA gene for haemagglutinin.
ACCESSION X68437;

SEQ ID NO: 44

```
   1 ctgtcaatca tgaagacaac cattattttg atactactga cccattgggt ctacagtcaa
  61 aacccaacca gtggcaacaa cacagccaca ttatgtctgg gacaccatgc agtagcaaat
 121 ggaacattgg taaaaacaat aactgatgac caaattgagg tgacaaatgc tactgaatta
 181 gttcagagca tttcaatagg gaaaatatgc aacaactcat atagggttct agatggaaga
 241 aattgcacat taatagatgc aatgctagga gacccccact gtgatgtttt tcagtatgag
 301 aattgggacc tcttcataga aagaagcagc gctttcagca attgctaccc atatgacatc
 361 cctgactatg catcgctccg gtccattgta gcatcctcag gaacattaga attcacagca
 421 gagggattca catggacagg tgtcactcaa aacggaagaa gtggagcctg caaaagggga
 481 tcagccgata gtttctttag ccgactgaat tggctaacaa aatctggaaa ttcttacccc
 541 atattgaatg tgacaatgcc taacaataaa aatttcgata aactatacat ctgggggatt
 601 catcacccga gctcaaacaa agagcagaca aaattgtata tccaagaatc aggacgagta
 661 acagtctcaa cagaaagaag tcaacaaaca gtaatcccta acatcggatc tagaccgtgg
 721 gtcaggggtc aatcaggcag gataagcata tactggacca ttgtaaaacc tggagatatt
 781 ctaacgataa acagtaatgg caacttagtt gcaccgcggg gatattttaa attgagaaca
 841 gggaaaagct ctgtaatgag atcagatgca cccatagaca cttgtgtgtc tgaatgtatt
 901 acaccaaatg gaagcatccc caacgacaaa ccatttcaaa atgtgaacaa agttacatat
 961 ggaaaatgcc ccaagtatat caggcaaaac actttaaagc tggccaccgg gatgaggaat
1021 gtaccagaaa agcaaatcag aggaatcttt ggagcaatag cgggattcat agaaaacggc
1081 tgggaaggaa tggttgatgg gtggtatgga ttccgatatc aaaactcgga aggaacagga
1141 caagctgcag atctaaagag cactcaagca gccatcgacc agatcaatgg aaaattaaac
1201 agagtgattg aaaggaccaa tgagaaattc catcaaatag agaaggaatt ctcagaagta
1261 gaagggagaa tccaggattt ggagaagtat gtagaagaca ccaaaataga cctatggtcc
1321 tacaatgcag aattgctggt ggctctagaa aatcaacata caattgactt aacagatgca
1381 gaaatgaata aattattcga gaagactagg cgccagttaa gagaaaacgc ggaagacatg
1441 ggaggtggat gtttcaagat ttaccacaaa tgtgataatg catgcattgg atcaataaga
1501 aatgggacat atgaccatta catatacaga gatgaagcat taaacaaccg atttcaaatc
1561 aaaggtgttg agttgaaatc aggctacaaa gattggatac tgtggatttc attcgccata
```

-continued

```
1621 tcatgcttct taatttgcgt tgttctattg ggtttcatta tgtgggcttg ccaaaaaggc

1681 aacatcagat gcaacatttg catttgagta aactgatagt taaaaacacc cttgtttcta

1741 ct
```

DEFINITION Influenza A virus (A/equine/Newmarket/1/77(H7N7)) gene for haemagglutinin.
ACCESSION X62554;

SEQ ID NO: 45

```
   1 nnnnnnnnnn nnnnnnnnna aatgaacact cagattctaa tattagccat ttcggcattc

  61 ctctgtgtac gtgcagataa aatctgccta ggacatcatg ctgtgtctaa tggaaccaaa

 121 gtagacaccc ttactgaaaa gggaatagaa gtcgtcaatg caacagaaac agttgaacaa

 181 aaaaacatcc ccaagatctg ctcaaaaggg aaacagacta ttgaccttgg tcaatgtgga

 241 ttactaggga ccactattgg tcccccccaa tgcgaccaat ttcttgaatt ctctgctaat

 301 ttaataattg agagaagaga aggtgatgat atttgttatc caggcaaatt tgacaatgaa

 361 gaaacattga gacaaatact cagaaaatcc ggaggaatta aaaaggagaa tatgggattc

 421 acatataccg gagtgagaac caatggagag actagcgcct gtagaaggtc aagatcttcc

 481 ttttatgcag aaatgaaatg gctcctatct aacacagaca atggggtatt cccacaaatg

 541 acaaaatcct acaagaacac taagaaggag ccagctctga taatctgggg aatccaccac

 601 tcaggatcaa ctgctgaaca gactagattg tatggaagtg gaaacaagtt gataacagtt

 661 tggagttcca aataccaaca atcttttgcc ccaaaccctg gaccaaggcc gcaaatgaat

 721 ggccaatcag gaagaattga cttttactgg ctgatgttag atcccaatga tactgttaat

 781 ttcagtttta atggggcctt tatagcacct gaccgcgcca gttttctaag aggtaaatct

 841 ctaggaattc agagtgacgc acaacttgac aacaattgtg aaggtgaatg ttatcatatt

 901 ggaggtacca taattagcaa cttgcccttt caaaacatta atagcagagc aattgggaaa

 961 tgccccagat acgtaaagca aaaaagctta atgctagcaa ccggaatgaa aaatgttcct

1021 gaaaattcta cacacaaaca gttaactcat cacatgcgca aaaaaagagg tttatttggt

1081 gcaatagcag gatttattga aaatggatgg gaaggattaa tagatggatg gtatggatac

1141 agacatcaga atgcacaagg agaaggaact gctgcagact acaaaagtac acaatctgct

1201 gtcaatcaaa taaccgggaa attaaacaga ctaatagaaa aaaccaacca gcaatttgaa

1261 ctaatagata atgaattcaa tgaaatagaa aagcaaattg gcaatgttat taactggact

1321 agagattcta tcatcgaaat atggtcatat aatgcagaat tcctcgtggc agtggagaat

1381 caacacacta ttgatttaac tgattcagag atgaacaaat tatatgaaaa ggtaagaaga

1441 cagctgagag aaaatgctga ggaagatggt aatggctgtt ttgaaatatt tcaccaatgt

1501 gacaatgatt gcatggccag cattagaaac aatacatatg atcataaaaa atacagaaag

1561 gaggcaatac aaaacagaat tcagattgat gcagtaaagt tgagcagcgg ttacaaagaa

1621 ataatacttt ggtttagctt cggggcatca tgtttcttat ttcttgccat tgcaatggtt

1681 cttgctttca tatgcataaa aaatggaaac atgcggtgca ctatttgtat ataagtttga

1741 aaaaacaccc ttgtttctan n
```

DEFINITION Influenza A virus HA partial gene for haemagglutinin, genomic RNA, strain A/equine/Newmarket-Bob Champion/89(H3N8).
ACCESSION AJ223193;

SEQ ID NO: 46

```
   1 agtcaaaacc caaccagtgg caacaacaca gccacattat gtctgggaca ccatgcagta

  61 gcaaatggaa cattggtaaa aacaataact gatgaccaaa ttgaggtgac aaatgctact

 121 gaattagttc agagcatttc aatagggaaa atatgcaaca actcatatag ggttctagat
```

-continued

```
 181 ggaagaaatt gcacattaat agatgcaatg ctaggagacc cccactgtga tgtttttcag

 241 tatgagaatt gggacctctt catagaaaga agcagcgctt tcagcaattg ctacccatat

 301 gacatccctg actatgcatc gctccggtcc attgtagcat cctcaggaac attagaattc

 361 acagcagagg gattcacatg gacaggtgtc actcaaaacg gaagaagtgg agcctgcaaa

 421 aggggatcag ccgatagttt ctttagccga ctgaattggc taacaaaatc tggaaattct

 481 taccccatat tgaatgtgac aatgcctaac aataaaaatt tcgataaact atacatctgg

 541 gggattcatc acccgagctc aaacaaagag cagacaaaat tgtatatcca agaatcagga

 601 cgagtaacag tctcaacaga aagaagtcaa caaacagtaa tccctaacat cggatctaga

 661 ccgtgggtca ggggtcaatc aggcaggata agcatatact ggaccattgt aaaacctgga

 721 gatattctaa tgataaacag taatggcaac ttagttgctc cgcggggata ttttaaattg

 781 agaacaggga aaagctctgt aatgagatca gatgcaccca tagacacttg tgtgtctgaa

 841 tgtattacac caaatggaag catccccaac gacaaaccat ttcaaaatgt gaacaaagtt

 901 acatatggaa aatgccccaa gtatatcagg caaaacactt taaagctggc cactgggatg

 961 aggaatgtac cagaaaagca aatcagagga atctttggag caatagaggg attcatagaa

1021 aacggctggg aaggaatggt tgatgggtgg tatggattcc gatatcaaaa ctcggaagga

1081 acaggacaag ctgcag
```

DEFINITION Influenza A virus (A/Equine/NewMarket/D64/79(H3N8)) gene for hemagglutinin precursor, partial cds.
ACCESSION D30677;

SEQ ID NO: 47

```
   1 ctgtcaatca tgaagacaac cattattttg atactactga cccattgggt ctacagtcaa

  61 aacccaacca gtggcaacaa cacagccaca ctatgtctgg gacaccatgc agtagcaaat

 121 ggaacattgg taaaaacaat aactgatgac caaattgagg tgacaaatgc cactgaatta

 181 gttcagagca cttcaatagg gaaaatatgc aacaacccat atagggttct agatggaaga

 241 aactgcacat taatagatgc aatgctagga gatccccact gtgatgtttt tcagtatgag

 301 aattgggacc tcttcataga aagaagcagc gctttcagca attgctaccc atatgacatc

 361 cctgactatg catcgctccg gtctattgtg gcatcttcag gaacattaga attcacagca

 421 gagggattca catggacagg tgtcactcaa aacggaagaa gtggcgcctg cagaagggga

 481 tcagccgata gtttctttag ccgactgaat tggctaacaa aatctggaga ttcttacccc

 541 acattgaatg tgacaatgcc taacaataac aatttcgata aactatacat ctgggggatc

 601 catcacccga gcacaaacaa tgagcagaca aaattgtatg tccaagaatc agggcgagta

 661 acagtctcaa caaaaagaag tcaacaaaca ataatcccca acatcggatc tagaccgtgg

 721 gtcaggggtc aaccaggcag gataagcata tattggacca ttgtgaaacc tggagatatc

 781 ctaatgataa acagtaatgg caacttagtt gcaccgcggg gatatttcaa aatgcgaaca

 841 ggaaaaagct ctataatgag atcagatgca cccatagaca cttgtgtgtc cgagtgtatt

 901 acaccaaatg gaagcatccc caacgacaaa ccatttcaaa atgtgaacaa agttacatat

 961 gggaaatgcc ccaagtatat caagcagaat actttgaagc tggccactgg gatgaggaat

1021 gtaccagaaa agcaaatcag aggaatcttt ggagcaatag cgggattcat agaaaatggc

1081 tgggag
```

DEFINITION Influenza A virus (A/eq/Newmarket/1/77(H7N7)) matrix proteins M1 and M2 (M) gene, complete cds.
ACCESSION AF001686;

SEQ ID NO: 48

```
   1 atgagtcttc tgaccgaggt cgaaacgtac gttctctcta tcgtaccatc aggccccctc
```

-continued

```
 61 aaagccgaga tcgcgcagag acttgaagat gtctttgcag gaaagaacac cgatcttgag

121 gcactcatgg aatggctaaa gacaagacca atcctgtcac ctctgactaa ggggatttta

181 ggatttgtgt tcacgctcac cgtgcccagt gagcgaggac tgcagcgtag acgctttgtc

241 caaaatgccc ttaatgggaa cggagatcca aacaacatgg acagagcagt aaaactgtac

301 aggaagctta aaagggaaat aacattccat ggggcaaaag aggtggcact cagctattcc

361 actggtgcac tagccagctg catgggactc atatacaaca gaatggggac tgtgacaacc

421 gaagtggcat ttggcctggt atgcgccaca tgtgaacaga ttgctgattc ccagcaccga

481 tctcacagac agatggtgac aacaaccaac ccactaatca gacacgagaa cagaatggta

541 ctagccagta ccacagctaa agccatggag cagatggcag ggtcgagtga gcaggcagca

601 gaggccatgg aggttgctag tcaggccagg cagatggtgc aggcaatgag aaccattggg

661 acccacccta gctccagtgc cggtttgaaa aatgatcttc ttgaaaattt gcaggcctac

721 cagaaacgga tgggagtgca aatgcagcga ttcaagtgat cctctcgtta ttgcagcaag

781 tatcattggg atcttgcact tgatattgtg gattcttgat cgtcttttct tcaaatgcat

841 ttatcgtcgt cttaaatacg gtttgaaaag agggccttct acggaaggag tacctgagtc

901 tatgagggaa gaatatcggc aggaacagca gagtgctgtg gatgttgacg atggtcattt

961 tgtcaacata gagctggagt aa
```

DEFINITION Influenza A virus (A/eq/Newmarket/79(H3N8)) matrix proteins M1 and M2 (M) gene, complete cds.
ACCESSION AF001675;

SEQ ID NO: 49

```
  1 atgagtcttc taaccgaggt cgaaacgtac gttctctcta tcgtaccatc aggccccctc

 61 aaagccgaga tcgcgcagag acttgaagat gtctttgcag ggaagaacac cgatcttgag

121 gcactcatgg aatggctaaa gacaagacca atcctgtcac ctctgactaa agggatttta

181 ggatttgtgt tcacgctcac cgtgcccagt gagcgaggac tgcagcgtag acgctttgtc

241 caaaatgccc ttagtggaaa cggagatcca aacaacatgg acagagcagt aaaactgtac

301 aggaagctta aaagagaaat aacattccat ggggcaaaag aggtggcact cagctattcc

361 actggtgcac tagccagctg catgggactc atatacaaca gaatggggac tgtgacaacc

421 gaagtggcat ttggcctggt atgcgccaca tgtgaacaga ttgctgattc ccagcatcga

481 tctcacaggc agatggtgac aacaaccaac ccactaatca gacatgaaaa cagaatggta

541 ctagccagta ccacagctaa agccatggag cagatggcag ggtcgagtga gcaggcagca

601 gaggccatgg aggttgctag taaggccagg cagatggtac aggcaatgag gaccattggg

661 acccacccta gctccagtgc cggtttgaaa gatgatcttc ttgaaaattt gcaggcctac

721 cagaaacgga tgggagtgca aatgcagcga ttcaagtgat cctctcgtta ttgcagcaag

781 tatcattggg atcttgcact tgatattgtg gattcttgat cgccttttct tcaaattcat

841 ttatcgtcgc cttaaatacg gtttgaaaag agggccttct acggaaggag tacctgagtc

901 tatgagggaa gaatatcggc aggaacagca gaatgctgtg gatgttgacg atggtcattt

961 tgtcaacata gagctggagt aa
```

DEFINITION Influenza A virus (A/eq/Newmarket/1/77(H7N7)) nonstructural proteins NS1 and NS2 (NS) gene, complete cds.
ACCESSION AF001663;

SEQ ID NO: 50

```
  1 atggattcca acactgtgtc aagctttcag gtagactgtt ttctttggca tgtccgcaaa

 61 cgatttgcag accaagaact gggtgatgcc ccattccttg accggcttcg ccgagaccag

121 aagtccctaa aaggaagagg cagcactctt ggtctggaca tcgaaacagc cactcatgca
```

-continued

```
181 ggaaagcaga tagtggagcg aattctggaa gaggaatcag atgaggcact taaaatgacc

241 atagcctctg ttcctacttc acgctactta actgacatga ctcttgatga gatgtcaaga

301 gactggttca tgctcatgcc caagcagaaa gtaacaggct ccctatgtat aaggatggac

361 caagcaatca tggataagaa catcatacta aaagcaaact ttagtgtgat tttcgaaagg

421 ctggagacac taatactact tagagctttc accgaagaag gagcagtcgt tggcgaaatt

481 tcaccattgc cttctcttcc aggacatact aatgaggatg tcaaaaatgc aattggggtc

541 ctcatcggag gacttaaatg gaatgataac acagttagag tctctgaaac tctacagaga

601 ttcgcttgga gaagcagtca tgagaatggg agaccttcat tccctccaaa gcagaaacga

661 aaaatggcga gaacaattga gtcagaagtt tgaagaaata aggtggttga ttgaagaagt

721 gagacataga ttgaaaaata cagaaaatag ttttgaacaa ataacattta tgcaagcctt

781 acaactattg cttgaagtag aacaagagat aagaactttc tcgtttcagc ttatttaa
```

DEFINITION Influenza A virus (A/eq/Newmarket/D63/79(H3N8))
nonstructural proteins NS1 and NS2 (NS) gene, complete cds.
ACCESSION AF001662;

SEQ ID NO: 51

```
  1 atggattcca acactgtgtc aagctttcag gtagactgtt ttctttggca tgtccgcaaa

 61 cgatttgcag accaagaact gggtgatgcc ccattccttg accggcttcg ccgagaccag

121 aagtccctaa aaggaagagg cagcactctt ggtctggaca tcgaaacagc cactcgtgca

181 ggaaagcaga tagtggagcg gattctggaa gaggagtcag atgaggcact taaaatgacc

241 attgcctctg ttcctgcttc acgctactta actgacatga ctcttgatga gatgtcaaga

301 gactggttca tgctcatgcc caagcagaaa gtaacaggct ccctatgtat aaggatggac

361 caggcaatca tggataagaa catcatacta aaagcaaact ttagtgtgat tttcgaaagg

421 ctggagacac taatactact tagagccttc accgaagaag gagcagtcgt tggcgaaatt

481 tcaccattgc cttctcttcc aggacatact aatgaggatg tcaaaaatgc aattggggtc

541 ctcatcggag gacttaaatg gaatgataat acagttagag tctctgaaac tctacagaga

601 ttcgcttgga gaagcagtca tgagaatggg agaccttcat tccctccaaa gcagaaacga

661 aaaatggcga gaacaattga gccagaagtt tgaagaaata agatggttga ttgaagaagt

721 gcgacataga ttgaaaaata cagaaaatag ttttgaacaa ataacattta tgcaagcctt

781 acaactattg cttgaagtag aacaagagat aagaactttc tcgtttcagc ttatttaa
```

The invention is further described by the following numbered paragraphs:

1. A method of eliciting an immune response against influenza in a canine, comprising administering a formulation comprising an avipox expression vector comprising a polynucleotide encoding an influenza antigen, epitope or immunogen and a pharmaceutically or veterinarily acceptable carrier, excipient or vehicle in an effective amount for eliciting an immune response.

2. A method of inducing an immune response against influenza in a canine, comprising administering a formulation comprising an avipox expression vector comprising a polynucleotide encoding an influenza antigen, epitope or immunogen and a pharmaceutically or veterinarily acceptable carrier, excipient or vehicle in an effective amount for inducing an immune response.

3. The method of paragraph 1 or 2, wherein the formulation further comprises an adjuvant.

4. The method of any one of paragraphs 1 to 3, wherein the influenza antigen, epitope or immunogen is a hemagglutinin, matrix protein, membrane protein, neuraminidase, nonstructural protein, nucleoprotein, polymerase or any fragment thereof.

5. The method of any one of paragraphs 1 to 4, wherein the influenza antigen, epitope or immunogen is isolated from a canine infected with influenza.

6. The method of paragraph 5 wherein the influenza antigen, epitope or immunogen is isolated from the broncho alveolar lavage and/or lung tissues of the canine.

7. The method of any one of paragraphs 1 to 4, wherein the influenza antigen, epitope or immunogen is isolated from an equine influenza.

8. The method of paragraph 7, wherein the equine influenza is an Ohio equine influenza, a Kentucky equine influenza or a Newmarket equine influenza.

9. The method of any one of paragraphs 1 to 8, wherein the avipox expression vector is an attenuated avipox expression vector.

10. The method of paragraph 9, wherein the avipox expression vector is a canarypox vector.

11. The method of paragraph 10, wherein the canarypox vector is ALVAC.

12. The method of paragraph 10 or 11, wherein the influenza antigen, epitope or immunogen is a hemagglutinin.

13. The method of paragraph 12, wherein the hemagglutinin is H3.

14. The method of paragraph 12 or 13, wherein the canarypox vector is CP1529 or CP1533.

15. A method of eliciting an immune response against influenza in a canine, comprising administering a formulation comprising an inactivated influenza vaccine and a pharmaceutically or veterinarily acceptable carrier, excipient or vehicle in an effective amount for eliciting an immune response.

16. A method of inducing an immune response against influenza in a canine, comprising administering a formulation comprising an inactivated influenza vaccine and a pharmaceutically or veterinarily acceptable carrier, excipient or vehicle in an effective amount for inducing an immune response.

17. The method of paragraph 15 or 16, wherein the formulation further comprises an adjuvant.

18. The method of any one of paragraph 15 to 17, wherein the inactivated influenza vaccine is an inactivated canine influenza.

19. The method of any one of paragraphs 15 to 17, wherein the inactivated influenza vaccine is an inactivated equine influenza.

20. The method of paragraph 19, wherein the equine influenza is an Ohio equine influenza, a Kentucky equine influenza or a Newmarket equine influenza.

21. A kit for performing any one of the methods of paragraphs 1 to 20 comprising the vaccine of any one of paragraphs 1 to 20 and instructions for performing the method of any one of paragraphs 1 to 20.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting an immune response in a canine against an equine strain of influenza, comprising administering a composition comprising a recombinant poxvirus that contains DNA encoding and that expresses in vivo in a canine, equine influenza antigen comprising equine influenza H3 and a pharmaceutically or veterinarily acceptable carrier, excipient or vehicle in an effective amount for eliciting the immune response.

2. The method of claim 1, wherein the composition further comprises an adjuvant.

3. The method of claim 1, wherein the DNA is isolated from a canine infected with equine influenza.

4. The method of claim 3 wherein the DNA is isolated from a broncho alveolar lavage of the infected canine.

5. The method of claim 3, wherein the DNA is isolated from lung tissue of the infected canine.

6. The method of claim 1, wherein the DNA is isolated from an equine influenza virus isolate.

7. The method of claim 6, wherein the equine influenza virus is selected from the group consisting of an Ohio equine influenza virus isolate, a Kentucky equine influenza virus isolate, a Newmarket equine influenza virus isolate or mixtures thereof.

8. The method of claim 1, wherein the poxvirus is an avipox virus.

9. The method of claim 8 wherein the avipox virus is a canarypox virus.

10. The method of claim 1, wherein the canarypox virus is ALVAC.

11. The method of claim 10, wherein the DNA is from a Kentucky equine influenza virus isolate.

12. The method of claim 10, wherein the DNA is from a Newmarket equine influenza virus isolate.

13. The method of claim 9, wherein the canarypox virus is selected from CP1529, CP1533 or CP2242.

14. The method of claim 1 wherein the equine influenza antigen comprises H3N8 codon optimized HA.

15. The method of claim 1 wherein the equine influenza antigen is H3.

16. The method of claim 10 wherein the DNA is from Ohio equine influenza virus isolate.

* * * * *

SEQUENCE LISTING

```
<160> NUMBER OF SEQ ID NOS: 51

<210> SEQ ID NO 1
<211> LENGTH: 3959
<212> TYPE: DNA
<213> ORGANISM: Influenza A virus

<400> SEQUENCE: 1

gtattctaaa ctaggaatag atgaaattat gtgcaaagga gatacctta gatatggatc     60

tgatttattt ggtttttcat aatcataatc taacaacatt ttcactatac tataccttct    120

tgcacaagtc gccattagta gtatagactt atactttgta accatagtat actttagcgc    180

gtcatcttct tcatctaaaa cagatttaca acaataatca tcgtcgtcat cttcatcttc    240

attaaagttt tcatattcaa taactttctt ttctaaaaca tcatctgaat caataaacat    300

agaacggtat agagcgttaa tctccattgt aaaatatact aacgcgttgc tcatgatgta    360

ctttttttc attatttaga aattatgcat tttagatctt tataagcggc cgtgattaac    420

tagtcataaa aacccgggat cgattctaga ctcgagcggc cgccagtgtg atggatatct    480

gcagaattcg gctttggtcc ttactcaaat gcaaatgttg cacctgatgt tgcctttttg    540

gcaagcccac ataatgaaac ccaatagaac aacgcaaatt aagaagcatg atatggcgaa    600

tgaaatccac agtatccaat ctttgtagcc tgatttcaac tcaacacttt tgatttgaaa    660

tcggttgttt aatgcttcat ctctgtatat gtaatggtca tatgtcccat ttcttattga    720

tccaatgcat gcattatcac atttgtggta aatcttgaaa catccacctc ccatgtcttc    780

cgcgttttct cttaactggc gcctagtctt ctcgaataat ttattcattt ctgcatctgt    840

taagtcaatt gtatgttgat tttctagagc caccagcaat tctgcattgt aggaccatag    900

gtctattttg gtgtcttcta catacttctc caaatcctgg attctccctt ctacttctga    960

gaattccttt tctatttgat ggaatttctc attggtcctt tcaatcactc tgtttaattt   1020

tccattgatc tggtctatgg ctgcttgagt gctctttaga tctgcagctt gtcctgttcc   1080

ttccgagttt tgatatcgga atccatacca cccatcaacc attccttccc agccgttttc   1140
```

-continued

```
tatgaatccc gctattgctc caaagattcc tctgatttgc ttttctggta cattcctcat   1200

cccagtggcc agctttaaag tgttttgcct gatatacttg gggcattttc catatgtaat   1260

tttgttcaca ttttgaaatg gtttgtcgtt ggggatgctt ccatttggtg taatacattc   1320

agacacacaa gtgtctatga gtgcatctga tctcattaca gagcttttcc ctgttctcaa   1380

tttaaaatat ccccgcggtg caactaagtt gccattactg tttatcatta gaatatctcc   1440

aggttttaca atggtccagt atatgcttat cctgcctgat tgacccctga cccacggcct   1500

agatccgatg ttagggatta ctgtttgttg acttctttct gttgagactg ttactcgtcc   1560

tgattcttgg atatataatt ttgtctgctc tttgtttgag ctcgggtgat gaatccccca   1620

gatgtatagt ttatcgaaat ttttattgtt aggcattgtc acattcaata tggggtaaga   1680

atttccagat tttgttagcc aattcagtcg gctaaagaaa ctatcggctg atcccctttt   1740

gcaggctcca cttcttccgt tttgagtgac acctgtccat gtgaacccct ctgctgtgaa   1800

ttctaatgtt cctgaggatg ctacaatgga ccggagcgat gcatagtcag ggatgtcata   1860

tgggtagcaa ttgctgaaag cgctgcttct ttctatgaag aggtcccaat tctcatactg   1920

aaaatcatca caatgggggt ctcctagcat tgcatctatt aatgtgcaat ttcttccatc   1980

tagaacccta tatgagttgt tgcatatttt ccctattgaa atgctctgga ctaattcagt   2040

agcatttgtc acctcaattt ggtcatcagt tattgttttt accaatgttc catttgctac   2100

tgcatggtgt cccagacata atgtggctgt gttgttgcca ctggttgggt tttgactgta   2160

gacccaatgg gtcagtagta tcaaaataat ggttgtcttc attacgatac aaacttaacg   2220

gatatcgcga taatgaaata atttatgatt atttctcgct ttcaatttaa cacaaccctc   2280

aagaaccttt gtatttattt tcacttttta agtatagaat aaagaagctc taattaatta   2340

acgagcagat agtctcgttc tcgccctgcc tgatgactaa ttaattaacc cggatccttt   2400

ttatagctaa ttagtcacgt acctttgaga gtaccacttc agctacctct tttgtgtctc   2460

agagtaactt tctttaatca attccaaaac agtatatgat tttccatttc tttcaaagat   2520

gtagtttaca tctgctcctt tgttgaaaag tagcctgagc acttcttttc taccatgaat   2580

tacagctggc aagatcaatt tttcccagtt ctggacattt tattttttt aagtagtgtg   2640

ctacatattt caatatttcc agattgtaca gcgatcatta aaggagtacg tcccatgtta   2700

tccagcaagt cagtatcagc acctttgttc aatagaagtt taaccattgt taaattttta   2760

tttgatacgg ctatatgtag aggagttaac cgatccgtgt ttgaaatatc tacatccgcc   2820

gaatgagcca atagaagttt aaccaaatta actttgttaa ggtaagctgc caaacacaaa   2880

ggagtaaagc ctccgctgta aagaacattg tttacatagt tattcttcaa cagatctttc   2940

actattttgt agtcgtctct caacaccgca tcatgcagac aagaagttgt gcattcagta   3000

actacaggtt tagctccata cctcatcaag atttttatag cctcggtatt cttgaacatt   3060

acagccattt caagaggaga ttgtagagta ccatattccg tgttagggtc gaatccattg   3120

tccaaaaacc tatttagaga tgcattgtca ttatccatga tagcctcaca gacgtatatg   3180

taagccatct tgaatgtata attttgttgt tttcaacaac cgctcgtgaa cagcttctat   3240

actttttcat tttcttcatg attaatatag tttacggaat ataagtatac aaaaagttta   3300

tagtaatctc ataatatctg aaacacatac ataaaacatg gaagaattac acgatgtcgt   3360

tgagataaat ggctttttat tgtcatagtt tacaaattcg cagtaatctt catcttttac   3420

gaatattgca gaatctgttt tatccaacca gtgatttttg tataatataa ctggtatcct   3480

atcttccgat agaatgctgt tatttaacat ttttgcacct attaagttac atctgtcaaa   3540
```

-continued

```
tccatctttc caactgactt tatgtaacga tgcgaaatag catttatcac tatgtcgtac   3600

ccaattatca tgacaagatt ctcttaaata cgtaatctta ttatctcttg catattcgta   3660

atagtaattg taaagagtat acgataacag tatagatata cacgtgatat aaatatttaa   3720

ccccattcct gagtaaaata attacgatat tacatttcct tttattattt ttatgtttta   3780

gttatttgtt aggttataca aaaattatgt ttatttgtgt atatttaaag cgtcgttaag   3840

aataagctta gttaacatat tatcgcttag gttttgtagt atttgaatcc tttctttaaa   3900

tggattattt ttccaatgca tatttatagc ttcatccaaa gtataacatt taacattca    3959
```

<210> SEQ ID NO 2
<211> LENGTH: 3917
<212> TYPE: DNA
<213> ORGANISM: Influenza A virus

<400> SEQUENCE: 2

```
gtattctaaa ctaggaatag atgaaattat gtgcaaagga gataccttta gatatggatc     60

tgatttattt ggtttttcat aatcataatc taacaacatt ttcactatac tataccttct    120

tgcacaagtc gccattagta gtatagactt atactttgta accatagtat actttagcgc    180

gtcatcttct tcatctaaaa cagatttaca acaataatca tcgtcgtcat cttcatcttc    240

attaaagttt tcatattcaa taactttctt ttctaaaaca tcatctgaat caataaacat    300

agaacggtat agagcgttaa tctccattgt aaaatatact aacgcgttgc tcatgatgta    360

cttttttttc attatttaga aattatgcat tttagatctt tataagcggc cgtgattaac    420

tagtcataaa aacccgggat cgattctaga ctcgagggta cctcaaatgc aaatgttgca    480

tctgatgttg cctttttggc aagcccacat aatgaaaccc aatagaacaa cgcaaattaa    540

gaagcatgat atggcgaatg aaatccacag tatccaatct ttgtagcctg atttcaactc    600

aacacctttg atttgaaatc ggttgtttaa tgcttcatct ctgtatatgt aatggtcata    660

tgtcccattt cttattgatc caatgcatgc attatcacat ttgtggtaaa tcttgaaaca    720

tccacctccc atgtcttccg cgttttctct taactggcgt ctagtcttct cgaataattt    780

attcatttct gcatctgtta agtcaattgt atgttgattt tctagagcca ccagcaattc    840

tgcattgtag gaccataggt ctattttggt gtcttctaca tacttctcca agtcctggat    900

tctcccttct acttctgaga attccttctc tatttgatgg aatttctcat tggtcctttc    960

aatcactctg tttaatttc cattaatctg gtcgatggct gcttgagtgc tctttagatc    1020

tgcagcttgt cctgttcctt ccgagttttg atatcggaat ccataccacc catcaaccat   1080

tccttcccag ccgttttcta tgaatcccgc tattgctcca aagattcctc tgatttgctt   1140

ttctggtaca ttcctcatcc cagtggccag ctttaaagtg ttttgcctga tatacttggg   1200

gcattttcca tatgtaactt tgttcacatt ttgaaatggt ttgtcgttgg ggatgcttcc   1260

atttggtgta atacattcag acacacaaat gtctatgggt gcatctgatc tcattacaga   1320

gcttttccct gttttcaatt taaaatatcc ccgcggtgca actaagttgc cattactgtt   1380

tatcattagg atatctccag gttttacaat ggtccagtat atgcttatcc tgcctgattg   1440

acccctgacc cacggtctag atccgatatt agggattatc gtttgttgac ttctttttgt   1500

tgagactgtt actcgtcctg attcttggat gtacaattct gtttgctgtt ggtttgagct   1560

cgggtgatga atcccccaga tgtatagttt gtcgaaattt ttattgttag gcattgtcac   1620

attcaatgtg ggtaagagt ttccagattt tgttagccaa ttcagtcggc taaagaaact    1680
```

-continued

```
atcggctgat ccccttttgc aggctccact tcttccgttt tgagtgacac ctgtccatgt   1740

gaatccctct gctgtgaatt ccaatgttcc tgaggatgct acaatggacc ggagcgatgc   1800

atagtcaggg atgtcatatg ggtagcaatt gctgaaagcg ctgcttcttt ctatgaagag   1860

gtcccaattc tcatactgaa agacatcaca gtgggggtct cctagcattg catctattaa   1920

tgtgcaattt cttccatcta gaactctata tgagttgttg catattttcc ctattgaaat   1980

gctctgaact aattcagtag catttgtcac ctcaatttgg tcatcagtta ttgtttttac   2040

caatgttcca tttgctactg catggtgtcc cagacataat gtggctgtgt tgttgccact   2100

ggttgggttt tgactgtaga cccaatgggt cagtagtatc aaaataatgg ttgtcttcat   2160

tacgatacaa acttaacgga tatcgcgata atgaaataat ttatgattat ttctcgcttt   2220

caatttaaca caaccctcaa gaacctttgt atttattttc actttttaag tatagaataa   2280

agaagctcta attaattaac gagcagatag tctcgttctc gccctgcctg atgactaatt   2340

aattaacccg gatccttttt atagctaatt agtcacgtac ctttgagagt accacttcag   2400

ctacctcttt tgtgtctcag agtaactttc tttaatcaat tccaaaacag tatatgattt   2460

tccatttctt tcaaagatgt agtttacatc tgctcctttg ttgaaaagta gcctgagcac   2520

ttcttttcta ccatgaatta cagctggcaa gatcaatttt tcccagttct ggacatttta   2580

ttttttttaa gtagtgtgct acatatttca atatttccag attgtacagc gatcattaaa   2640

ggagtacgtc ccatgttatc cagcaagtca gtatcagcac ctttgttcaa tagaagttta   2700

accattgtta aatttttatt tgatacggct atatgtagag gagttaaccg atccgtgttt   2760

gaaatatcta catccgccga atgagccaat agaagtttaa ccaaattaac tttgttaagg   2820

taagctgcca aacacaaagg agtaaagcct ccgctgtaaa gaacattgtt tacatagtta   2880

ttcttcaaca gatctttcac tattttgtag tcgtctctca acaccgcatc atgcagacaa   2940

gaagttgtgc attcagtaac tacaggttta gctccatacc tcatcaagat ttttatagcc   3000

tcggtattct tgaacattac agccatttca agaggagatt gtagagtacc atattccgtg   3060

ttagggtcga atccattgtc caaaaaccta tttagagatg cattgtcatt atccatgata   3120

gcctcacaga cgtatatgta agccatcttg aatgtataat tttgttgttt tcaacaaccg   3180

ctcgtgaaca gcttctatac tttttcattt tcttcatgat taatatagtt tacggaatat   3240

aagtatacaa aaagtttata gtaatctcat aatatctgaa acacatacat aaaacatgga   3300

agaattacac gatgtcgttg agataaatgg ctttttattg tcatagttta caaattcgca   3360

gtaatcttca tcttttacga atattgcaga atctgtttta tccaaccagt gatttttgta   3420

taatataact ggtatcctat cttccgatag aatgctgtta tttaacattt ttgcacctat   3480

taagttacat ctgtcaaatc catctttcca actgacttta tgtaacgatg cgaaatagca   3540

tttatcacta tgtcgtaccc aattatcatg acaagattct cttaaatacg taatcttatt   3600

atctcttgca tattcgtaat agtaattgta aagagtatac gataacagta tagatataca   3660

cgtgatataa atatttaacc ccattcctga gtaaaataat tacgatatta catttccttt   3720

tattattttt atgttttagt tatttgttag gttatacaaa aattatgttt atttgtgtat   3780

atttaaagcg tcgttaagaa taagcttagt taacatatta tcgcttaggt tttgtagtat   3840

ttgaatcctt tctttaaatg gattattttt ccaatgcata tttatagctt catccaaagt   3900

ataacattta acattca                                                  3917
```

```
<210> SEQ ID NO 3
<211> LENGTH: 565
```

-continued

<212> TYPE: PRT
<213> ORGANISM: Influenza A virus

<400> SEQUENCE: 3

```
Met Lys Thr Thr Ile Ile Leu Ile Leu Leu Thr His Trp Val Tyr Ser
  1               5                  10                  15

Gln Asn Pro Thr Ser Gly Asn Asn Thr Ala Thr Leu Cys Leu Gly His
             20                  25                  30

His Ala Val Ala Asn Gly Thr Leu Val Lys Thr Ile Thr Asp Asp Gln
         35                  40                  45

Ile Glu Val Thr Asn Ala Thr Glu Leu Val Gln Ser Ile Ser Ile Gly
     50                  55                  60

Lys Ile Cys Asn Asn Ser Tyr Arg Val Leu Asp Gly Arg Asn Cys Thr
 65                  70                  75                  80

Leu Ile Asp Ala Met Leu Gly Asp Pro His Cys Asp Asp Phe Gln Tyr
                 85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Asn Ser Tyr
                165                 170                 175

Pro Ile Leu Asn Val Thr Met Pro Asn Asn Lys Asn Phe Asp Lys Leu
            180                 185                 190

Tyr Ile Trp Gly Ile His His Pro Ser Ser Asn Lys Glu Gln Thr Lys
        195                 200                 205

Leu Tyr Ile Gln Glu Ser Gly Arg Val Thr Val Ser Thr Glu Arg Ser
    210                 215                 220

Gln Gln Thr Val Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Arg Thr Gly Lys Ser Ser Val Met Arg Ser Asp Ala Leu
        275                 280                 285

Ile Asp Thr Cys Val Ser Glu Cys Ile Thr Pro Asn Gly Ser Ile Pro
    290                 295                 300

Asn Asp Lys Pro Phe Gln Asn Val Asn Lys Ile Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400
```

-continued

```
Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Ser Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565
```

<210> SEQ ID NO 4
<211> LENGTH: 565
<212> TYPE: PRT
<213> ORGANISM: Influenza A virus

<400> SEQUENCE: 4

```
Met Lys Thr Thr Ile Ile Leu Ile Leu Leu Thr His Trp Ala Tyr Ser
  1               5                  10                  15

Gln Asn Pro Ile Ser Gly Asn Asn Thr Ala Thr Leu Cys Leu Gly His
             20                  25                  30

His Ala Val Ala Asn Gly Thr Leu Val Lys Thr Ile Ser Asp Asp Gln
         35                  40                  45

Ile Glu Val Thr Asn Ala Thr Glu Leu Val Gln Ser Ile Ser Met Gly
     50                  55                  60

Lys Ile Cys Asn Asn Ser Tyr Arg Ile Leu Asp Gly Arg Asn Cys Thr
 65                  70                  75                  80

Leu Ile Asp Ala Met Leu Gly Asp Pro His Cys Asp Ala Phe Gln Tyr
                 85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
```

-continued

```
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Lys Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 5
<211> LENGTH: 565
<212> TYPE: PRT
<213> ORGANISM: Influenza A virus

<400> SEQUENCE: 5
```

-continued

```
Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Ile Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Lys Thr Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
```

-continued

```
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Lys Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565


<210> SEQ ID NO 6
<211> LENGTH: 3973
<212> TYPE: DNA
<213> ORGANISM: Influenza A virus
<220> FEATURE:
<221> NAME/KEY: CDS
<222> LOCATION: (1800)..(3494)

<400> SEQUENCE: 6

ggaaacagct atgaccatga ttacgaattg cggccgcaat tctgaatgtt aaatgttata     60

ctttggatga agctataaat atgcattgga aaaataatcc atttaaagaa aggattcaaa    120

tactacaaaa cctaagcgat aatatgttaa ctaagcttat tcttaacgac gctttaaata    180

tacacaaata aacataattt ttgtataacc taacaaataa ctaaaacata aaaataataa    240

aaggaaatgt aatatcgtaa ttattttact caggaatggg gttaaatatt tatatcacgt    300

gtatatctat actgttatcg tatactcttt acaattacta ttacgaatat gcaagagata    360

ataagattac gtatttaaga gaatcttgtc atgataattg ggtacgacat agtgataaat    420

gctatttcgc atcgttacat aaagtcagtt ggaaagatgg atttgacaga tgtaacttaa    480

taggtgcaaa aatgttaaat aacagcattc tatcggaaga taggatacca gttatattat    540

acaaaaatca ctggttggat aaaacagatt ctgcaatatt cgtaaaagat gaagattact    600

gcgaatttgt aaactatgac aataaaaagc catttatctc aacgacatcg tgtaattctt    660

ccatgtttta tgtatgtgtt tcagatatta tgagattact ataaactttt tgtatactta    720

tattccgtaa actatattaa tcatgaagaa aatgaaaaag tatagaagct gttcacgagc    780

ggttgttgaa aacaacaaaa ttatacattc aagatggctt acatatacgt ctgtgaggct    840

atcatggata atgacaatgc atctctaaat aggtttttgg acaatggatt cgaccctaac    900

acggaatatg gtactctaca atctcctctt gaaatggctg taatgttcaa gaataccgag    960

gctataaaaa tcttgatgag gtatggagct aaacctgtag ttactgaatg cacaacttct   1020

tgtctgcatg atgcggtgtt gagagacgac tacaaaatag tgaaagatct gttgaagaat   1080

aactatgtaa acaatgttct ttacagcgga ggctttactc ctttgtgttt ggcagcttac   1140

cttaacaaag ttaatttggt taaacttcta ttggctcatt cggcggatgt agatatttca   1200
```

-continued

```
aacacggatc ggttaactcc tctacatata gccgtatcaa ataaaaattt aacaatggtt   1260

aaacttctat tgaacaaagg tgctgatact gacttgctgg ataacatggg acgtactcct   1320

ttaatgatcg ctgtacaatc tggaaatatt gaaatatgta gcacactact taaaaaaaat   1380

aaaatgtcca gaactgggaa aaattgatct tgccagctgt aattcatggt agaaaagaag   1440

tgctcaggct acttttcaac aaaggagcag atgtaaacta catctttgaa agaaatggaa   1500

aatcatatac tgttttggaa ttgattaaag aaagttactc tgagacacaa aagaggtagc   1560

tgaagtggta ctctcaaagg tacgtgacta attagctata aaaggatcc gggttaatta   1620

attagtcatc aggcagggcg agaacgagac tatctgctcg ttaattaatt agagcttctt   1680

tattctatac ttaaaaagtg aaaataaata caaaggttct tgagggttgt gttaaattga   1740

aagcgagaaa taatcataaa ttatttcatt atcgcgatat ccgttaagtt tgtatcgta    1799

atg aaa acc acc atc atc ctg atc ctg ctg acc cac tgg gcc tac agc     1847
Met Lys Thr Thr Ile Ile Leu Ile Leu Leu Thr His Trp Ala Tyr Ser
  1               5                  10                  15

cag aac cct atc agc ggc aac aac acc gcc acc ctg tgc ctg ggc cac     1895
Gln Asn Pro Ile Ser Gly Asn Asn Thr Ala Thr Leu Cys Leu Gly His
             20                  25                  30

cac gcc gtg gcc aac ggc acc ctg gtc aag acc atc agc gac gac cag     1943
His Ala Val Ala Asn Gly Thr Leu Val Lys Thr Ile Ser Asp Asp Gln
         35                  40                  45

atc gaa gtg acc aac gcc acc gag ctg gtg cag agc atc agc atg ggc     1991
Ile Glu Val Thr Asn Ala Thr Glu Leu Val Gln Ser Ile Ser Met Gly
     50                  55                  60

aag atc tgc aac aac agc tac cgc atc ctg gac ggc aga aac tgc acc     2039
Lys Ile Cys Asn Asn Ser Tyr Arg Ile Leu Asp Gly Arg Asn Cys Thr
 65                  70                  75                  80

ctg atc gac gcc atg ctg ggc gac ccc cac tgc gac gcc ttc cag tac     2087
Leu Ile Asp Ala Met Leu Gly Asp Pro His Cys Asp Ala Phe Gln Tyr
                 85                  90                  95

gag aac tgg gac ctg ttc atc gag agg agc agc gcc ttc agc aac tgc     2135
Glu Asn Trp Asp Leu Phe Ile Glu Arg Ser Ser Ala Phe Ser Asn Cys
            100                 105                 110

tac ccc tac gac atc cct gac tac gcc agc ctg aga agc atc gtg gcc     2183
Tyr Pro Tyr Asp Ile Pro Asp Tyr Ala Ser Leu Arg Ser Ile Val Ala
        115                 120                 125

agc agc ggc acc ctg gag ttc acc gcc gag ggc ttc acc tgg acc ggc     2231
Ser Ser Gly Thr Leu Glu Phe Thr Ala Glu Gly Phe Thr Trp Thr Gly
    130                 135                 140

gtg acc cag aac ggc aga agc ggc gcc tgc aag aga ggc agc gcc gac     2279
Val Thr Gln Asn Gly Arg Ser Gly Ala Cys Lys Arg Gly Ser Ala Asp
145                 150                 155                 160

agc ttc ttc agc cgc ctg aac tgg ctg acc aag agc ggc agc agc tac     2327
Ser Phe Phe Ser Arg Leu Asn Trp Leu Thr Lys Ser Gly Ser Ser Tyr
                165                 170                 175

ccc acc ctg aac gtg acc atg ccc aac aac aag aac ttc gac aag ctg     2375
Pro Thr Leu Asn Val Thr Met Pro Asn Asn Lys Asn Phe Asp Lys Leu
            180                 185                 190

tac atc tgg ggc atc cac cac ccc agc agc aac cag gag cag acc aag     2423
Tyr Ile Trp Gly Ile His His Pro Ser Ser Asn Gln Glu Gln Thr Lys
        195                 200                 205

ctg tac atc cag gag agc ggc aga gtg acc gtg tcc acc aag aga agc     2471
Leu Tyr Ile Gln Glu Ser Gly Arg Val Thr Val Ser Thr Lys Arg Ser
    210                 215                 220

cag cag acc atc atc ccc aac atc ggc agc aga cct tgg gtg cgc ggc     2519
Gln Gln Thr Ile Ile Pro Asn Ile Gly Ser Arg Pro Trp Val Arg Gly
```

-continued

```
225                 230                 235                 240

cag tcc ggc agg atc agc atc tac tgg acc atc gtg aag cct ggc gac     2567
Gln Ser Gly Arg Ile Ser Ile Tyr Trp Thr Ile Val Lys Pro Gly Asp
            245                 250                 255

atc ctg atg atc aac agc aac ggc aac ctg gtg gcc ccc aga ggc tac     2615
Ile Leu Met Ile Asn Ser Asn Gly Asn Leu Val Ala Pro Arg Gly Tyr
            260                 265                 270

ttc aag ctg aaa acc ggc aag agc agc gtg atg aga agc gac gtg ccc     2663
Phe Lys Leu Lys Thr Gly Lys Ser Ser Val Met Arg Ser Asp Val Pro
        275                 280                 285

atc gac atc tgc gtg tcc gag tgc atc acc cct aac ggc agc atc agc     2711
Ile Asp Ile Cys Val Ser Glu Cys Ile Thr Pro Asn Gly Ser Ile Ser
    290                 295                 300

aac gac aag ccc ttc cag aac gtg aac aaa gtg acc tac ggc aag tgc     2759
Asn Asp Lys Pro Phe Gln Asn Val Asn Lys Val Thr Tyr Gly Lys Cys
305                 310                 315                 320

ccc aag tac atc cgc cag aac acc ctg aag ctg gcc acc ggc atg aga     2807
Pro Lys Tyr Ile Arg Gln Asn Thr Leu Lys Leu Ala Thr Gly Met Arg
            325                 330                 335

aac gtg ccc gag aag cag atc aga ggc atc ttc ggc gcc atc gcc ggc     2855
Asn Val Pro Glu Lys Gln Ile Arg Gly Ile Phe Gly Ala Ile Ala Gly
            340                 345                 350

ttc atc gag aac ggc tgg gag ggc atg gtg gac ggc tgg tac ggc ttc     2903
Phe Ile Glu Asn Gly Trp Glu Gly Met Val Asp Gly Trp Tyr Gly Phe
        355                 360                 365

aga tac cag aac agc gag ggc acc ggc cag gcc gcc gac ctg aag agc     2951
Arg Tyr Gln Asn Ser Glu Gly Thr Gly Gln Ala Ala Asp Leu Lys Ser
    370                 375                 380

acc cag gcc gcc atc gac cag atc aac ggc aag ctg aac cgc gtg atc     2999
Thr Gln Ala Ala Ile Asp Gln Ile Asn Gly Lys Leu Asn Arg Val Ile
385                 390                 395                 400

gag cgc acc aac gag aag ttc cac cag atc gag aag gag ttc agc gaa     3047
Glu Arg Thr Asn Glu Lys Phe His Gln Ile Glu Lys Glu Phe Ser Glu
            405                 410                 415

gtg gag ggc aga atc cag gac ctg gag aag tac gtg gag gac acc aag     3095
Val Glu Gly Arg Ile Gln Asp Leu Glu Lys Tyr Val Glu Asp Thr Lys
            420                 425                 430

atc gac ctg tgg agc tac aac gcc gag ctg ctg gtc gcc ctg gag aac     3143
Ile Asp Leu Trp Ser Tyr Asn Ala Glu Leu Leu Val Ala Leu Glu Asn
        435                 440                 445

cag cac acc atc gac ctg acc gac gcc gag atg aac aag ctg ttc gaa     3191
Gln His Thr Ile Asp Leu Thr Asp Ala Glu Met Asn Lys Leu Phe Glu
    450                 455                 460

aag acc agg cgc cag ctg aag gaa aac gcc gag gac atg ggc ggc ggc     3239
Lys Thr Arg Arg Gln Leu Lys Glu Asn Ala Glu Asp Met Gly Gly Gly
465                 470                 475                 480

tgc ttc aag atc tac cac aag tgc gac aac gcc tgc atc ggc tcc atc     3287
Cys Phe Lys Ile Tyr His Lys Cys Asp Asn Ala Cys Ile Gly Ser Ile
            485                 490                 495

agg aac ggc acc tac gac cac tac atc tac agg gac gag gcc ctg aac     3335
Arg Asn Gly Thr Tyr Asp His Tyr Ile Tyr Arg Asp Glu Ala Leu Asn
            500                 505                 510

aac cgc ttc cag atc aag ggc gtg gag ctg aag agc ggc tac aag gac     3383
Asn Arg Phe Gln Ile Lys Gly Val Glu Leu Lys Ser Gly Tyr Lys Asp
        515                 520                 525

tgg atc ctg tgg atc agc ttc gcc atc agc tgc ttc ctg atc tgc gtg     3431
Trp Ile Leu Trp Ile Ser Phe Ala Ile Ser Cys Phe Leu Ile Cys Val
    530                 535                 540

gtg ctg ctg ggc ttc atc atg tgg gcc tgc cag aag ggc aac atc cgc     3479
```

-continued

```
Val Leu Leu Gly Phe Ile Met Trp Ala Cys Gln Lys Gly Asn Ile Arg
545                 550                 555                 560

tgc aac atc tgc atc tgatgactcg agggttttta tgactagtta atcacggccg     3534
Cys Asn Ile Cys Ile
                565

cttataaaga tctaaaatgc ataatttcta aataatgaaa aaaagtacat catgagcaac   3594

gcgttagtat attttacaat ggagattaac gctctatacc gttctatgtt tattgattca   3654

gatgatgttt tagaaaagaa agttattgaa tatgaaaact ttaatgaaga tgaagatgac   3714

gacgatgatt attgttgtaa atctgtttta gatgaagaag atgacgcgct aaagtatact   3774

atggttacaa agtataagtc tatactacta atggcgactt gtgcaagaag gtatagtata   3834

gtgaaaatgt tgttagatta tgattatgaa aaaccaaata aatcagatcc atatctaaag   3894

gtatctcctt tgcacataat ttcatctatt cctagtttag aatacctgca gccaagcttg   3954

gcactggccg tcgttttac                                                3973


<210> SEQ ID NO 7
<211> LENGTH: 3973
<212> TYPE: DNA
<213> ORGANISM: Influenza A virus

<400> SEQUENCE: 7

gtaaaacgac ggccagtgcc aagcttggct gcaggtattc taaactagga atagatgaaa     60

ttatgtgcaa aggagatacc tttagatatg gatctgattt atttggtttt tcataatcat    120

aatctaacaa cattttcact atactatacc ttcttgcaca agtcgccatt agtagtatag    180

acttatactt tgtaaccata gtatacttta gcgcgtcatc ttcttcatct aaaacagatt    240

tacaacaata atcatcgtcg tcatcttcat cttcattaaa gttttcatat tcaataactt    300

tcttttctaa aacatcatct gaatcaataa acatagaacg gtatagagcg ttaatctcca    360

ttgtaaaata tactaacgcg ttgctcatga tgtacttttt ttcattattt agaaattatg    420

cattttagat ctttataagc ggccgtgatt aactagtcat aaaaaccctc gagtcatcag    480

atgcagatgt tgcagcggat gttgcccttc tggcaggccc acatgatgaa gcccagcagc    540

accacgcaga tcaggaagca gctgatggcg aagctgatcc acaggatcca gtccttgtag    600

ccgctcttca gctccacgcc cttgatctgg aagcggttgt tcagggcctc gtccctgtag    660

atgtagtggt cgtaggtgcc gttcctgatg gagccgatgc aggcgttgtc gcacttgtgg    720

tagatcttga agcagccgcc gcccatgtcc tcggcgtttt ccttcagctg gcgcctggtc    780

ttttcgaaca gcttgttcat ctcggcgtcg gtcaggtcga tggtgtgctg gttctccagg    840

gcgaccagca gctcggcgtt gtagctccac aggtcgatct tggtgtcctc cacgtacttc    900

tccaggtcct ggattctgcc ctccacttcg ctgaactcct tctcgatctg gtggaacttc    960

tcgttggtgc gctcgatcac gcggttcagc ttgccgttga tctggtcgat ggcggcctgg   1020

gtgctcttca ggtcggcggc ctggccggtg ccctcgctgt tctggtatct gaagccgtac   1080

cagccgtcca ccatgccctc ccagccgttc tcgatgaagc cggcgatggc gccgaagatg   1140

cctctgatct gcttctcggg cacgtttctc atgccggtgg ccagcttcag ggtgttctgg   1200

cggatgtact tggggcactt gccgtaggtc actttgttca cgttctggaa gggcttgtcg   1260

ttgctgatgc tgccgttagg ggtgatgcac tcggacacgc agatgtcgat gggcacgtcg   1320

cttctcatca cgctgctctt gccggttttc agcttgaagt agcctctggg ggccaccagg   1380

ttgccgttgc tgttgatcat caggatgtcg ccaggcttca cgatggtcca gtagatgctg   1440
```

-continued

```
atcctgccgg actggccgcg cacccaaggt ctgctgccga tgttggggat gatggtctgc   1500
tggcttctct tggtggacac ggtcactctg ccgctctcct ggatgtacag cttggtctgc   1560
tcctggttgc tgctggggtg gtggatgccc cagatgtaca gcttgtcgaa gttcttgttg   1620
ttgggcatgg tcacgttcag ggtggggtag ctgctgccgc tcttggtcag ccagttcagg   1680
cggctgaaga agctgtcggc gctgcctctc ttgcaggcgc cgcttctgcc gttctgggtc   1740
acgccggtcc aggtgaagcc ctcggcggtg aactccaggg tgccgctgct ggccacgatg   1800
cttctcaggc tggcgtagtc agggatgtcg taggggtagc agttgctgaa ggcgctgctc   1860
ctctcgatga acaggtccca gttctcgtac tggaaggcgt cgcagtgggg gtcgcccagc   1920
atggcgtcga tcagggtgca gtttctgccg tccaggatgc ggtagctgtt gttgcagatc   1980
ttgcccatgc tgatgctctg caccagctcg gtggcgttgg tcacttcgat ctggtcgtcg   2040
ctgatggtct tgaccagggt gccgttggcc acggcgtggt ggcccaggca cagggtggcg   2100
gtgttgttgc cgctgatagg gttctggctg taggcccagt gggtcagcag gatcaggatg   2160
atggtggttt tcattacgat acaaacttaa cggatatcgc gataatgaaa taatttatga   2220
ttatttctcg ctttcaattt aacacaaccc tcaagaacct ttgtatttat tttcactttt   2280
taagtataga ataaagaagc tctaattaat taacgagcag atagtctcgt tctcgccctg   2340
cctgatgact aattaattaa cccggatcct tttatagct aattagtcac gtacctttga   2400
gagtaccact tcagctacct cttttgtgtc tcagagtaac tttctttaat caattccaaa   2460
acagtatatg attttccatt tctttcaaag atgtagttta catctgctcc tttgttgaaa   2520
agtagcctga gcacttcttt tctaccatga attacagctg gcaagatcaa tttttcccag   2580
ttctggacat tttatttttt ttaagtagtg tgctacatat ttcaatattt ccagattgta   2640
cagcgatcat taaaggagta cgtcccatgt tatccagcaa gtcagtatca gcacctttgt   2700
tcaatagaag tttaaccatt gttaaatttt tatttgatac ggctatatgt agaggagtta   2760
accgatccgt gtttgaaata tctacatccg ccgaatgagc caatagaagt ttaaccaaat   2820
taactttgtt aaggtaagct gccaaacaca aaggagtaaa gcctccgctg taaagaacat   2880
tgtttacata gttattcttc aacagatctt tcactatttt gtagtcgtct ctcaacaccg   2940
catcatgcag acaagaagtt gtgcattcag taactacagg tttagctcca tacctcatca   3000
agatttttat agcctcggta ttcttgaaca ttacagccat ttcaagagga gattgtagag   3060
taccatattc cgtgttaggg tcgaatccat tgtccaaaaa cctatttaga gatgcattgt   3120
cattatccat gatagcctca cagacgtata tgtaagccat cttgaatgta taattttgtt   3180
gttttcaaca accgctcgtg aacagcttct atactttttc attttcttca tgattaatat   3240
agtttacgga atataagtat acaaaaagtt tatagtaatc tcataaatatc tgaaacacat   3300
acataaaaca tggaagaatt acacgatgtc gttgagataa atggcttttt attgtcatag   3360
tttacaaatt cgcagtaatc ttcatctttt acgaatattg cagaatctgt tttatccaac   3420
cagtgatttt tgtataatat aactggtatc ctatcttccg atagaatgct gttatttaac   3480
atttttgcac ctattaagtt acatctgtca aatccatctt tccaactgac tttatgtaac   3540
gatgcgaaat agcatttatc actatgtcgt acccaattat catgacaaga ttctcttaaa   3600
tacgtaatct tattatctct tgcatattcg taatagtaat tgtaaagagt atacgataac   3660
agtatagata tacacgtgat ataaatattt aaccccattc ctgagtaaaa taattacgat   3720
attacatttc cttttattat ttttatgttt tagttatttg ttaggttata caaaaattat   3780
gtttatttgt gtatatttaa agcgtcgtta agaataagct tagttaacat attatcgctt   3840
```

-continued aggttttgta gtatttgaat cctttcttta aatggattat ttttccaatg catatttata 3900
gcttcatcca aagtataaca tttaacattc agaattgcgg ccgcaattcg taatcatggt 3960
catagctgtt tcc 3973

<210> SEQ ID NO 8
<211> LENGTH: 890
<212> TYPE: DNA
<213> ORGANISM: Influenza A virus

<400> SEQUENCE: 8
agcaaaagca gggtgacaaa aacataatgg attccaacac tgtgtcaagc tttcaggtag 60
actgttttct ttggcatgtc cgcaaacgat tcgcagacca agaactgggt gatgccccat 120
tccttgaccg gcttcgccga gaccagaagt ccctaagggg aagaggtatc actcttggtc 180
tggacatcga aacagccact catgcaggaa agcagatagt ggagcagatt ctggaaaagg 240
aatcagatga ggcacttaaa atgaccattg cctctgttcc tacttcacgc tacttaactg 300
acatgactct tgatgagatg tcaagagact ggttcatgct catgcccaag caaaaagtaa 360
caggctccct atgtataaga atggaccagg caatcatgga taagaacatc atacttaaag 420
caaactttag tgtgattttc gaaaggctgg aaacactaat actacttaga gccttcaccg 480
aagaaggagc agtcgttggc gaaatttcac cattaccttc tcttccagga catactaatg 540
aggatgtcaa aaatgcaatt ggggtcctca tcggaggact taaatggaat gataatacgg 600
ttagaatctc tgaaactcta cagagattcg cttggagaag cagtcatgag aatgggagac 660
cttcattccc ttcaaagcag aaatgaaaaa tggagagaac aattaagcca gaaatttgaa 720
gaaataagat ggttgattga agaagtgcga catagattga aaaatacaga aaatagtttt 780
gaacaaataa catttatgca agccttacaa ctattgcttg aagtagaaca agagataaga 840
actttctcgt ttcagcttat ttaatgataa aaaacaccct tgtttctact 890

<210> SEQ ID NO 9
<211> LENGTH: 1027
<212> TYPE: DNA
<213> ORGANISM: Influenza A virus

<400> SEQUENCE: 9
agcaaaagca ggtagatatt taaagatgag tcttctgacc gaggtcgaaa cgtacgttct 60
ctctatcgta ccatcaggcc ccctcaaagc cgagatcgcg cagagacttg aagatgtctt 120
tgcagggaag aacaccgatc ttgaggcact catggaatgg ctaaagacaa gaccaatcct 180
gtcacctttg actaaaggga ttttaggatt tgtattcacg ctcaccgtgc ccagtgagcg 240
aggactgcag cgtagacgct ttgtccaaaa tgcccttagt ggaaacggag atccaaacaa 300
catggacaga gcagtaaaac tgtacaggaa gcttaaaaga gaaataacat tccatggggc 360
aaaagaggtg gcactaagct attccactgg tgcactagcc agctgcatgg gactcatata 420
caacagaatg ggaactgtga caaccgaagt ggcatttggc ctggtatgcg ccacatgtga 480
acagattgct gattcccagc atcgatctca caggcagatg gtgacaacaa ccaaccccatt 540 aatcagacat gaaaacagaa tggtattagc cagtaccacg gctaaagcca tggaacagat 600
ggcaggatca agtgagcagg cagcagaggc catggaggtt gctagtaagg ctaggcagat 660
ggtacaggca atgagaacca ttgggaccca ccctagctcc agtgccggtt tgaaagatga 720
tctccttgaa aatttacagg cctaccagaa acggatggga gtgcaaatgc agcgattcaa 780

-continued gtgatcctct cgttattgca gcaagtatca ttgggatctt gcacttgata ttgtggattc 840
ttgatcgtct tttcttcaaa ttcatttatc gtcgccttaa atacgggttg aaaagagggc 900
cttctacgga aggagtacct gagtctatga gggaagaata tcggcaggaa cagcagaatg 960
ctgtggatgt tgacgatggt cattttgtca acatagagct ggagtaaaaa actaccttgt 1020
ttctact 1027

<210> SEQ ID NO 10
<211> LENGTH: 1460
<212> TYPE: DNA
<213> ORGANISM: Influenza A virus

<400> SEQUENCE: 10
agcaaaagca ggagtttaaa atgaatccaa atcaaaagat aatagcaatt ggatttgcat 60
cattggggat attaatcatt aacgtcattc tccatgtagt cagcattata gtaacagtac 120
tggtcctcaa taacaatgga acaggtctga actgcaaagg gacgatcata agagagtaca 180
atgaaacagt aagagtagaa aaaattactc aatggtataa taccagtgca attaagtaca 240
tagagagacc tccaaatgaa tactacatga acaacaccga accactttgt gaggcccaag 300
gctttgcacc attttccaaa gataatggaa tacgaattgg gtcgagaggc catgtttttg 360
tgataagaga accttttgta tcatgttcgc cctcagaatg tagaaccttt ttcctcacac 420
agggctcatt actcaatgac aaacattcta acggcacagt aaaggaccga agtccatata 480
ggactttgat gagtgtcaaa atagggcaat cacctaatgt gtatcaagct aggtttgaat 540
cggtggcatg gtcagcaaca gcatgccatg atggaaaaaa atggatgaca gttggagtca 600
cagggcccga caatcaagca attgcagtag tgaactatgg aggtgttccg gttgatatta 660
ttaattcatg ggcaggggat atcttaagaa cccaagaatc atcatgcacc tgcattaaag 720
gagactgtta ttgggtaatg actgatggac cggcaaatag gcaagctaaa tataggatat 780
tcaaagcaaa agatggaaga gtaattggac agactgatat aagtttcaat gggggacaca 840
tagaggagtg ttcttgttac cccaatgaag ggaaggtgga atgcatatgc agggacaatt 900
ggactggaac aaatagacca attctggtaa tatcttctga tctatcgtac acagttggat 960
atttgtgtgc tggcattccc actgacactc ctaggggaga ggatagtcaa ttcacaggct 1020
catgtacaag acctttggga aataaaggat acggtgtaaa aggtttcggg tttcgacaag 1080
gaactgacgt atgggccgga aggacaatta gtaggacttc aagatcagga ttcgaaataa 1140
taaaaatcag gaatggttgg acacagaaca gtaaagacca aatcaggagg caagtgatta 1200
tcgatgaccc aaattggtca ggatatagcg gttctttcac attgccggtt gaactaacaa 1260
aaaagggatg tttggtcccc tgtttctggg ttgaaatgat tagaggtaaa cctgaagaaa 1320
caacaatatg gacctctagc agctccattg tgatgtgtgg agtagatcat aaaattgcca 1380
gttggtcatg gcacgatgga gctattcttc cctttgacat cgataagatg taatttacga 1440
aaaaactcct tgtttctact 1460

<210> SEQ ID NO 11
<211> LENGTH: 1565
<212> TYPE: DNA
<213> ORGANISM: Influenza A virus

<400> SEQUENCE: 11
agcaaaagca gggtagataa tcactcactg agtgacatca aagtcatggc gtctcaaggc 60
accaaacgat cctatgaaca gatggaaact gatggggaac gccagaatgc aactgaaatc 120

-continued

```
agagcatctg tcggaaggat ggtgggagga atcggccggt tttatgttca gatgtgtact    180
gagcttaaac taaacgacca tgaagggcgg ctgattcaga acagcataac aatagaaagg    240
atggtacttt cggcattcga cgaaagaaga aacaagtatc tcgaggagca tcccagtgct    300
ggaaaagacc ctaagaaaac gggaggcccg atatacagaa ggaaagatgg gaaatggatg    360
agggaactca tcctccatga taaagaagaa atcatgagaa tctggcgtca ggccaacaat    420
ggtgaagacg ctactgctgg tcttactcat atgatgatct ggcactccaa tctcaatgac    480
accacatacc aaagaacaag ggctcttgtt cggactggga tggatcccag aatgtgctct    540
ctgatgcaag gctcaaccct cccacggaga tctggagccg ctggtgctgc agtaaaaggt    600
gttggaacaa tggtaatgga actcatcaga atgatcaaac gcggaataaa tgatcggaat    660
ttctggagag gtgaaaatgg tcgaaggacc agaattgctt atgaaagaat gtgcaatatc    720
ctcaaaggga aatttcagac agcagcacaa cgggctatga tggaccaggt gagggaaggc    780
cgcaatcctg gaaacgctga gattgaggat ctcattttct tagcacgatc agcacttatt    840
ttgagaggat cagtagccca taaatcatgc ctacctgcct gtgtttatgg ccttgcagta    900
accagtgggt atgactttga gaaggaagga tactctctgg ttggaattga tcctttcaaa    960
ctactccaga acagtcaaat tttcagtcta atcagaccaa aagaaaaccc agcacacaag   1020
agccagttgg tgtggatggc atgccattct gcagcatttg aggacctgag agttttgaat   1080
ttcattagag gaaccaaagt aatcccaaga ggacagttaa caaccagagg agttcaaatt   1140
gcttcaaatg aaaacatgga gacaatagat tctagcacac ttgaactgag aagcaaatat   1200
tgggcaataa ggaccagaag tggaggaaac accagtcaac agagagcatc tgcaggacag   1260
ataagtgtgc aacctacttt ctcagtacag agaaatcttc cctttgagag agcaaccatt   1320
atggctgcat tcactggtaa cactgaaggg aggacttccg acatgagaac ggaaatcata   1380
aggatgatgg aaagtgccaa atcagaagat gtgtctttcc aggggcgggg agtcttcgag   1440
ctctcggacg aaaaggcaac gaacccgatc gtgccttcct ttgacatgag caatgaaggg   1500
tcttatttct tcggagacaa tgctgaggaa tttgacagtt aaagaaaaat acccttgttt   1560
ctact                                                                1565
```

<210> SEQ ID NO 12
<211> LENGTH: 1762
<212> TYPE: DNA
<213> ORGANISM: Influenza A virus

<400> SEQUENCE: 12

```
agcaaaagca ggggatattt ctgtcaatca tgaagacaac cattattttg atactactga     60
cccattgggc ctacagtcaa aacccaatca gtggcaacaa cacagccaca ttgtgtctgg    120
gacaccatgc agtagcaaat ggaacattgg taaaaacaat aagtgatgat caaattgagg    180
tgacaaatgc tacagaatta gttcagagca tttcaatggg gaaaatatgc aacaactcat    240
atagaattct agatggaaga aattgcacat taatagatgc aatgctagga gacccccact    300
gtgacgtctt tcagtatgag aattgggacc tctttataga aagaagcagc gctttcagca    360
attgctaccc atatgacatc cctgactatg catcgctccg atccattgta gcatcctcag    420
gaacattgga attcacagca gagggattca catggacagg tgtcactcaa aacggaagaa    480
gtggagcctg caaaagggga tcagccgata gtttctttag ccgactgaat tggctaacaa    540
aatctggaaa ctcttacccc acattgaatg tgacaatgcc taacaataaa aatttcgaca    600
```

-continued

```
agctatacat ctgggggatt catcacccga gctcaaatca agagcagaca aaattgtaca    660

tccaagaatc aggacgagta acagtctcaa caaaaagaag tcaacaaaca ataatcccta    720

acatcggatc tagaccgtgg gtcagaggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgca cccatagaca    900

tttgtgtgtc tgaatgtatt acaccaaatg gaagcatctc caacgacaag ccattccaaa    960

atgtgaacaa agttacatat ggaaaatgcc ccaagtatat caggcaaaac actttaaagt   1020

tggccactgg gatgaggaat gtaccagaaa agcaaatcag aggaatcttt ggagcaatag   1080

cgggattcat cgaaaacggc tgggaaggaa tggttgatgg gtggtatggg ttccgatatc   1140

aaaactctga aggaacaggg caagctgcag atctaaagag cactcaagca gccatcgacc   1200

agattaatgg aaagttaaac agagtgattg aaagaaccaa tgagaaattc catcaaatag   1260

agaaggaatt ctcagaagta gaaggaagaa ttcaggactt ggagaaatat gtagaagaca   1320

ccaaaataga cctatggtcc tacaatgcag aattgctggt ggctctagaa aatcaacata   1380

caattgactt aacagatgca gaaatgaata aattattcga gaagactaga cgccagttaa   1440

gagaaaacgc agaagacatg ggaggtggat gtttcaagat ttaccacaaa tgtgataatg   1500

catgcattgg atcaataaga aatgggacat atgaccatta catatacaga gatgaagcat   1560

taaacaaccg atttcaaatc aaaggtgttg agttgaaatc aggctacaaa gattggatac   1620

tgtggatttc attcgccata tcatgcttct taatttgcgt tgttctattg ggtttcatta   1680

tgtgggcttg ccaaaaaggc aacatcagat gcaacatttg catttgagta aactgatagt   1740

taaaaacacc cttgtttcta ct                                            1762
```

```
<210> SEQ ID NO 13
<211> LENGTH: 2233
<212> TYPE: DNA
<213> ORGANISM: Influenza A virus

<400> SEQUENCE: 13
```

```
agcgaaagca ggtactgatc caaaatggaa gactttgtgc gacagtgctt caatccaatg     60

atcgtcgagc ttgcggaaaa ggcaatgaaa gaatatggag aggacccgaa aatcgaaaca    120

aacaaatttg cagcaatatg cactcacttg gaagtctgct tcatgtactc ggatttccac    180

tttattaatg aactgggtga gtcagtggtc atagagtctg gtgacccaaa tgctcttttg    240

aaacacagat ttgaaatcat tgaggggaga gatcgaacaa tggcatggac agtggtaaac    300

agcatctgca acaccacaag agctgaaaaa cctaaatttc ttccagattt atacgactat    360

aaggagaaca gatttgttga aattggtgtg acaaggagag aagttcacat atactacctg    420

gagaaggcca acaaaataaa gtctgagaaa acacatatcc acattttctc atttacagga    480

gaggaaatgg ctacaaaagc ggactatact cttgatgaag agagtagagc caggatcaag    540

accagactat tcactataag acaagaaatg gccagtagag gcctctggga ttcctttcgt    600

cagtccgaga gaggcgaaga gacaattgaa gaaagatttg aaatcacagg gacgatgcgc    660

aagcttgcca attacagtct cccaccgaac ttctccagcc ttgaaaattt tagagtctat    720

gtggatggat tcgaaccgaa cggctgcatt gagagtaagc tttctcaaat gtccaaagaa    780

gtaaatgcca gaatcgaacc attttcaaag acaacacccc gaccactcaa aatgccaggt    840

ggtccaccct gccatcagcg atctaaattc ttgctaatgg atgctctgaa actgagcatt    900

gaggacccaa gtcacgaggg agagggaata ccactatatg atgcaatcaa atgcatgaaa    960
```

-continued

```
actttctttg gatggaaaga gcccagtatt gttaaaccac atgaaaaggg tataaacccg   1020

aactatctcc aaacttggaa gcaagtatta gaagaaatac aagaccttga gaacgaagaa   1080

aggaccccca agaccaagaa tatgaaaaaa acaagccaat tgaaatgggc actaggtgaa   1140

aatatggcac cagagaaagt ggattttgag gattgtaaag acatcagtga tttaaaacag   1200

tatgacagcg atgagccaga aacaaggtct cttgcaagtt ggattcaaag tgagttcaac   1260

aaagcttgtg agctgacaga ttcaagctgg atagagctcg atgaaattgg ggaggatgtc   1320

gccccaatag aatacattgc gagcatgagg agaaattatt ttactgctga gatttcccat   1380

tgtagagcaa cagaatatat aatgaaagga gtgtacatca acactgctct actcaatgca   1440

tcctgtgctg cgatggatga atttcaatta attccgatga taagtaaatg caggaccaaa   1500

gaagggagaa ggaaaacaaa tttatatgga ttcataataa agggaaggtc ccatttaaga   1560

aatgatactg acgtggtgaa ctttgtaagt atggaatttt ctctcactga tccaagattt   1620

gagccacaca aatgggaaaa atactgcgtt ctagaaattg gagacatgct tctaaggact   1680

gctgtaggtc aagtgtcaag acccatgttt ttgtatgtaa ggacaaatgg aacctctaaa   1740

attaaaatga aatggggaat ggaaatgagg cgctgcctcc ttcagtctct gcaacagatt   1800

gaaagcatga tcgaagctga gtcctcagtc aaagaaaagg acatgaccaa agaatttttt   1860

gagaacaaat cagagacatg gcctatagga gagtccccca aaggagtgga agagggctca   1920

atcgggaagg tttgcaggac cttattagca aaatctgtgt ttaacagttt atatgcatct   1980

ccacaactgg aagggttttc agctgaatct aggaaattac ttctcattgt tcaggctctt   2040

agggataacc tggaacctgg aacctttgat attggggggt tatatgaatc aattgaggag   2100

tgcctgatta atgatccctg ggttttgctt aatgcatctt ggttcaactc cttccttaca   2160

catgcactga agtagttgtg gcaatgctac tatttgctat ccatactgtc caaaaaagta   2220

ccttgtttct act                                                      2233
```

<210> SEQ ID NO 14
<211> LENGTH: 2341
<212> TYPE: DNA
<213> ORGANISM: Influenza A virus

<400> SEQUENCE: 14

```
agcgaaagca ggcaaaccat ttgaatggat gtcaatccga ctctactttt cttaaaggtg     60

ccagcgcaaa atgctataag cacaacattc ccttatactg gagatcctcc ctacagtcat    120

ggaacaggga caggatacac catggatact gtcaacagaa cacaccaata ttcagaaaag    180

gggaaatgga caacaaacac tgagattgga gcaccacaac ttaatccaat cgatggacca    240

cttcctgaag acaatgaacc aagtgggtac gcccaaacag attgtgtatt ggaagcaatg    300

gctttccttg aagaatccca tcccggaatc tttgaaaatt cgtgtcttga aacgatggag    360

gtgattcagc agacaagagt ggacaaacta acacaaggcc gacaaactta tgattggacc    420

ttgaatagga atcaacctgc cgcaacagca cttgctaata caattgaagt gttcagatca    480

aatggtctga cttccaatga atcagggagg ttgatggact tcctcaaaga tgtcatggag    540

tccatgaaca aggaagaaat ggaaataaca acacacttcc aacgaaagag aagagtaaga    600

gacaacatga caaagagaat ggtaacacag agaaccatag ggaagaaaaa acaacgatta    660

aacagaaaga gttatctaat cagaacatta accctaaaca caatgaccaa ggacgctgag    720

agagggaaat tgaaacgacg agcaatcgca accccaggga tgcagataag aggatttgta    780
```

-continued

```
tattttgttg aaacactagc ccgaagaata tgtgaaaagc ttgaacaatc aggattgcca    840

gttggcggta atgagaaaaa ggccaaactg gctaatgtcg tcagaaaaat gatgactaat    900

tcccaagaca ctgaactctc cttcaccatc actggggaca ataccaaatg gaatgaaaat    960

cagaacccac gcatattcct ggcaatgatc acatacataa ctagaaacca gccagaatgg   1020

ttcagaaatg ttctaagcat tgcaccgatt atgttctcaa ataaaatggc aagactgggg   1080

aaaggatata tgtttgaaag caaaagtatg aaactgagag ctcaaatacc agcagaaatg   1140

ctagcaagca ttgacctgaa atatttcaat gattcaacaa aaaagaaaat taaaaagata   1200

cgaccacttc tggttgacgg gactgcttca ctgagtcctg gcatgatgat gggaatgttc   1260

aacatgttga gcactgtgct gggtgtatcc atattaaacc tgggccagag gaaatacaca   1320

aagaccacat actggtggga tggtctgcaa tcatccgatg actttgcttt gatagtgaat   1380

gcgcctaatc atgaaggaat acaagctgga gtagacagat tctatagaac ttgcaaactg   1440

gtcgggatca acatgagcaa aaagaagtcc tacataaata gaaccggaac attcgaattc   1500

acaagctttt tctaccggta tggttttgta gccaatttca gcatggaact acccagtttt   1560

ggggtttccg gaataaatga atctgcagac atgagcattg gagtgacagt catcaaaaac   1620

aacatgataa ataatgatct cggtcctgcc acggcacaaa tggcactcca actcttcatt   1680

aaggattacc ggtacacata ccggtgccat agaggtgata cccagataca aaccagaaga   1740

tcttttgagt tgaagaaact gtgggaacag actcgatcaa agactggtct actggtatca   1800

gatgggggtc caaacctata taacatcaga aacctacaca tcccggaagt ttgtttaaaa   1860

tgggagctaa tggatgaaga ttataagggg aggctatgca atccattaaa tcctttcgtt   1920

agtcacaaag aaattgaatc agtcaacagt gcagtagtaa tgcctgcgca tggccctgcc   1980

aaaagcatgg agtatgatgc tgttgcaaca acacattctt ggatccccaa gaggaaccgg   2040

tccatattga acacaagcca aaggggaata ctcgaagatg agcagatgta tcagaaatgc   2100

tgcaacctgt ttgaaaaatt cttccccagc agctcataca gaagaccagt cggaatttct   2160

agtatggttg aggccatggt gtccagggcc cgcattgatg cacgaattga cttcgaatct   2220

ggacggataa agaaggatga gttcgctgag atcatgaaga tctgttccac cattgaagag   2280

ctcagacggc aaaaatagtg aatttagctt gatcttcatg aaaaaatgcc ttgtttctac   2340

t                                                                   2341
```

```
<210> SEQ ID NO 15
<211> LENGTH: 2341
<212> TYPE: DNA
<213> ORGANISM: Influenza A virus

<400> SEQUENCE: 15

agcgaaagca ggtcaaatat attcaatatg gagagaataa aagaactgag agatctgatg     60

ttacaatccc gcacccgcga gatactaaca aaaactactg tggaccacat ggccataatc    120

aagaaataca catcaggaag acaagagaag aaccctgcac ttaggatgaa atggatgatg    180

gcaatgaaat acccaattac agcagataag aggataatgg agatgattcc tgagagaaat    240

gaacagggac aaaccctttg gagcaaaacg aacgatgctg gctcagaccg cgtaatggta    300

tcacctctgg cagtgacatg gtggaatagg aatggaccaa caacgagcac aattcattat    360

ccaaaagtct acaaaactta ttttgaaaag gttgaaagat tgaaacacgg aacctttggc    420

cccgttcatt ttaggaatca agtcaagata agacgaagag ttgatgtaaa ccctggtcac    480

gcggacctca gtgccaaaga agcacaagat gtgatcatgg aagttgtttt cccaaatgaa    540
```

-continued gtgggagcca gaattctaac atcggaatca caactaacaa taaccaaaga gaaaaaggaa 600
gaacttcagg actgcaaaat tgctcccttg atggtagcat acatgctaga aagagagttg 660
gtccgaaaaa caaggttcct cccagtggca ggcggaacaa gcagtgtata cattgaagtg 720
ttgcatctga ctcagggaac atgctgggag caaatgtaca ccccaggagg agaagttaga 780
aacgatgata ttgatcaaag tttaattatt gcagcccgga acatagtgag aagagcgaca 840
gtatcagcag atccactagc atccctactg gaaatgtgcc acagtacaca gattggtgga 900
ataaggatgg tagacatcct taagcagaat ccaacagagg aacaagctgt ggatatatgc 960
aaagcagcaa tgggattgag aattagctca tcattcagct ttggtggatt caccttcaaa 1020
agaacaagtg gatcatcagt caagagagaa gaagaaatgc ttacgggcaa ccttcaaaca 1080
ttgaaaataa gagtgcatga gggctatgaa gaattcacaa tggtcggaag aagagcaaca 1140
gccattctca gaaaggcaac cagaagattg attcaattga tagtaagtgg gagagatgaa 1200
caatcaattg ctgaagcaat aattgtagcc atggtgtttt cgcaagaaga ttgcatgata 1260
aaagcagttc gaggcgattt gaactttgtt aatagagcaa atcagcgttt gaaccccatg 1320
catcaactct tgaggcattt ccaaaaagat gcaaaagtgc ttttccaaaa ttggggaatt 1380
gaacccatcg acaatgtaat gggaatgatt ggaatattgc ctgacatgac cccaagcacc 1440
gagatgtcat tgagaggagt gagagtcagc aaaatgggag tggatgagta ctccagcact 1500
gagagagtgg tggtgagcat tgaccgtttt ttaagagttc gggatcaaag gggaaacata 1560
ctactgtccc ctgaagaagt cagtgaaaca caaggaacgg aaaagctgac aataatttat 1620
tcgtcatcaa tgatgtggga gattaatggt cccgaatcag tgttggtcaa tacttatcaa 1680
tggatcatca ggaactggga aattgtaaaa attcagtggt cacaggaccc cacaatgtta 1740
tacaataaga tagaatttga gccattccag tccctggtcc ctagggccac cagaagccaa 1800
tacagcggtt tcgtaagaac cctgtttcag caaatgcgag atgtacttgg aacatttgat 1860
actgctcaaa taataaaact cctccctttt gccgctgctc ctccggaaca gagtaggatg 1920
cagttctctt ctttgactgt taatgtaaga ggatcgggaa tgaggatact tgtaagaggc 1980
aattccccag tgttcaacta caataaagcc actaaaaggc tcacagtcct cggaaaggat 2040
gcaggtgcgc ttactgagga cccagatgaa ggtacggctg gagtagaatc tgctgttcta 2100
agagggtttc tcattttagg taaagaaaac aagagatatg gcccagcact aagcatcaat 2160
gaactaagca aacttgcaaa aggggagaaa gccaatgtac taattgggca aggggacgta 2220
gtgttggtaa tgaaacggaa acgtgactct agcatactta ctgacagcca gacagcgacc 2280
aaaaggattc ggatggccat caattagtgt tgaattgttt aaaaacgacc ttgtttctac 2340
t 2341

<210> SEQ ID NO 16
<211> LENGTH: 1762
<212> TYPE: DNA
<213> ORGANISM: Influenza A virus

<400> SEQUENCE: 16
agcaaaagca ggggatattt ctgtcaatca tgaagacaac cattattttg atactactga 60
cccattgggt ctacagtcaa aacccaacca gtggcaacaa cacagccaca ttatgtctgg 120
gacaccatgc agtagcaaat ggaacattgg taaaaacaat aactgatgac caaattgagg 180
tgacaaatgc tactgaatta gttcagagca tttcaatagg gaaaatatgc aacaactcat 240

-continued

```
atagagttct agatggaaga aattgcacat taatagatgc aatgctagga gacccccact     300

gtgatgtctt tcagtatgag aattgggacc tcttcataga aagaagcagc gctttcagca     360

gttgctaccc atatgacatc cctgactatg catcgctccg gtccattgta gcatcctcag     420

gaacattgga attcacagca gagggattca catggacagg tgtcactcaa aacggaagaa     480

gtggatcctg caaaagggga tcagccgata gtttctttag ccgactgaat tggctaacaa     540

aatctggaaa ctcttacccc acattgaatg tgacaatgcc taacaataaa aatttcgaca     600

aactatacat ctgggggatt catcacccga gctcaaacga agagcagaca aaattgtaca     660

tccaagaatc aggacgagta acagtctcaa caaaaagaag tcaacaaaca ataatcccta     720

acatcggatc tagaccgtgg gtcaggggtc aatcaggcag gataagcata tactggacca     780

ttgtaaaacc tggagatatc ctaatgataa acagtaatgg caacttagtt gcaccgcggg     840

gatattttaa attgaaaaca gggaaaagct ctgtaatgag atcagatgca cccatagaca     900

tttgtgtgtc tgaatgtatt acaccaaatg gaagcatccc caacgacaaa ccatttcaaa     960

atgtgaacaa agttacatat ggaaaatgcc ccaagtatat caggcaaaac actttaaagc    1020

tggccactgg gatgaggaat gtaccagaaa agcaaatcag aggaatcttt ggagcaatag    1080

cgggattcat agaaaacggc tgggaaggaa tggttgatgg gtggtatgga ttccgatatc    1140

aaaactcgga aggaacagga caagctgcag atctaaagag cactcaagca gccatcgacc    1200

agatcaatgg aaaattaaac agagtgattg aaaggaccaa tgagaaattc catcaaatag    1260

agaaggaatt ctcagaagta gaagggagaa tccaggattt ggagaagtat gtagaagaca    1320

ccaaaataga cctatggtcc tacaatgcag aattgctggt ggctctagaa aatcaacata    1380

caattgactt aacagatgca gaaatgaata aattattcga gaagactaga cgccagttaa    1440

gagaaaacgc ggaagacatg ggaggtggat gtttcaagat ataccacaaa tgtgataatg    1500

catgcattgg atcaataaga aatgggacat atgaccatta catatacaga gatgaagcat    1560

taaacaaccg gtttcaaatc aaaggtgttg agttgaaatc aggctacaaa gattggatac    1620

tgtggatttc attcgccata tcatgcttct taatttgcgt tgttctattg ggtttcatta    1680

tgtgggcttg ccaaaaaggc aacatcagat gcaacatttg catttgagta aactgatagt    1740

taaaaacacc cttgtttcta ct                                             1762
```

<210> SEQ ID NO 17
<211> LENGTH: 1762
<212> TYPE: DNA
<213> ORGANISM: Influenza A virus

<400> SEQUENCE: 17

```
agcaaaagca ggggatattt ctgtcaatca tgaagacaac cattattttg atactactga      60

cccattgggt ctacagtcaa aacccaacca gtggcaacaa cacagccaca ttatgtctgg     120

gacaccatgc agtagcaaat ggaacattgg taaaaacaat aactgatgac caaattgagg     180

tgacaaatgc tactgaatta gttcagagca tttcaatagg gaaaatatgc aacaactcat     240

atagggttct agatggaaga aattgcacat taatagatgc aatgctagga gacccccact     300

gtgatgtctt tcagtatgag aattgggacc tcttcataga aagaagcagc gctttcagca     360

attgctaccc atatgacatc cctgactatg catcgctccg gtccattgta gcatcctcag     420

gaacattaga attcacagca gagggattca catggacagg tgtcactcaa aacggaagaa     480

gtggagcctg caaaagggga tcagccgata gtttctttag ccgactgaat tggctaacaa     540

aatctggaaa ctcttacccc acattgaatg tgacaatgcc taacaataaa aatttcgaca     600
```

-continued

```
aactatacat ctgggggatt catcacccga gctcaaacaa tgagcagaca aaattgtata    660

tccaagaaac aggacgagta acagtctcaa caaaaagaag tcaacaaaca ataatcccta    720

acatcggatc tagaccgtgg gtcaggggtc aatcaggcag gataagcata tactggacca    780

ttgtaaaacc tggagatatc ctaatgataa acagcaatgg caacttagtt gcaccgcggg    840

gatattttaa attgagaaca gggagaagct ctgtaatgag atcagatgca cccatagaca    900

tttgtgtgtc tgaatgtatt acaccaaatg gaagcatccc caacgacaaa ccatttcaaa    960

atgtgaacaa agttacatat ggaaaatgcc ccaaatatat caggcaaaac actttaaagc   1020

tggccactgg gatgaggaat gtaccagaaa agcaaatcag aggaatcttt ggagcaatag   1080

cgggattcat agaaaacggc tgggaaggaa tggttgatgg gtggtatgga ttccgatatc   1140

aaaactcgga aggaacagga caagctgcag atctaaagag cactcaagca gccatcgacc   1200

agatcaatgg aaaattaaac agagtgattg aaaggaccaa tgagaaattc catcaaatag   1260

agaaggaatt ctcagaagta gaagggagaa tccaggattt ggagaagtat gtagaagaca   1320

ccaaaataga cctatggtcc tacaatgcag aattgctagt ggctctagaa aatcaacata   1380

caattgactt aacagacgca gaaatgaata aattattcga gaagactaga cgccagttaa   1440

gagaaaacgc ggaagacatg ggaggtggat gtttcaagat ttaccacaaa tgtgataatg   1500

catgcattgg atcaataaga aatgggacat atgaccatta catatacaga gatgaagcat   1560

taaacaaccg atttcaaatc aaaggtgttg aattaaaatc aggctacaaa gattggatac   1620

tgtggatttc attcgccata tcatgcttct taatttgtgt tgttctattg ggtttcatta   1680

tgtgggcttg ccaaaaaggc aacatcagat gcaacatttg catttgagta aactgatagt   1740

taaaaacacc cttgtttcta ct                                            1762
```

```
<210> SEQ ID NO 18
<211> LENGTH: 1762
<212> TYPE: DNA
<213> ORGANISM: Influenza A virus

<400> SEQUENCE: 18

agcaaaagca ggggatattt ctgtcaatca tgaaaacaac cattattttg atactactga     60

cccattgggt ctacagtcaa aacccaacca gtggcaacaa cacagccaca ttatgtctgg    120

gacaccatgc agtagcaaat ggaacattgg taaaaacaat aactgatgac caaattgagg    180

tgacaaatgc tactgaatta gttcagagca tttcaatagg aaaaatatgc aacaactcat    240

atagggttct agatggaaga aattgcacat taatagatgc aatgctagga gaccctcact    300

gtgatgtctt tcagtatgag aattgggacc tcttcataga aagaagcagc gctttcagca    360

attgctaccc atatgacatc cctgactatg catcgctccg gtccattgta gcatcctcag    420

gaacattaga attcacagca gagggattca catggacagg tgtcactcaa aacggaggaa    480

gtggagcctg caaaagagga tcagccgata gtttctttag ccgactgaat tggctaacaa    540

aatctggaaa ctcttacccc acattgaatg tgacaatgcc taacaataaa aatttcgaca    600

aactatacat ctgggggatt catcacccga gctcaaacaa tgagcagaca aaattgtata    660

tccaagaatc aggacgagta acagtctcaa caaaaagaag tcaacaaaca ataatcccta    720

acatcggatc tagaccgtgg gtcaggggtc aatcaggcag gataagcata tactggacca    780

ttgtaaaacc tggagatatc ctaatgataa acagtaatgg caacttagtt gcaccgcggg    840

gatattttaa attgagaaca gggaaaagct ctgtaatgag atcagatgca cccatagaca    900
```

-continued

```
cttgtgtgtc tgaatgtatt acaccaaatg gaagcatccc caacgacaaa ccatttcaaa     960

atgtgaacaa agttacatat ggaaaatgcc ccaagtatat caggcaaaac actttaaagc    1020

tggccactgg gatgaggaat gtaccagaaa agcaaatcag aggaatcttt ggagcaatag    1080

cgggattcat agaaaacggc tgggaaggaa tggttgatgg gtggtatgga ttccgatatc    1140

aaaactcgga aggaacagga caagctgcag atctaaagag cactcaagca gccatcgacc    1200

agatcaatgg aaaattaaac agagtgattg aaaggaccaa tgagaaattc catcaaatag    1260

agaaggaatt ctcagaagta gaagggagaa tcaaggactt ggagaagtat gtagaagaca    1320

ccaaaataga cctatggtcc tacaatgcag aattgctggt ggctctagaa aatcaacata    1380

caattgactt aacagatgca gaaatgaata aattattcga gaagactaga cgccagttaa    1440

gagaaaacgc ggaagacatg ggaggtggat gtttcaagat ctaccacaaa tgtgataatg    1500

catgcattgg atcaataaga aatgggacat atgaccatta catatacaaa gatgaagcat    1560

taaacaaccg atttcaaatc aaaggtgttg agttgaaatc aggctacaaa gattggatac    1620

tgtggatttc attcgccata tcatgcttct taatttgcgt tgttctattg ggtttcatta    1680

tgtgggcttg ccaaaaaggc aacatcagat gcaacatttg catttgagta aactgatagt    1740

taaaaacacc cttgtttcta ct                                             1762
```

```
<210> SEQ ID NO 19
<211> LENGTH: 1762
<212> TYPE: DNA
<213> ORGANISM: Influenza A virus

<400> SEQUENCE: 19

agcaaaagca ggggatattt ctgtcaatca tgaagacaac cattattttg atactactga      60

cccattgggt ctacagtcaa aacccaacca gtggcaacaa cacagccaca ttatgtctgg     120

gacaccatgc agtagcaaat ggaacattgg taaaaacaat aactgatgac caaattgagg     180

tgacaaatgc tactgaatta gttcagagca tttcaatagg gaaaatatgc aacaactcat     240

atagagttct agatggaaga aattgcacat taatagatgc aatgctagga gacccccact     300

gtgatgtctt tcagtatgag aattgggacc tcttcataga aagaagcagc gctttcagca     360

attgctaccc atatgacatc cctgactatg catcgctccg gtccattgta gcatcctcag     420

gaacattgga attcacagca gagggattca catggacagg tgtcactcaa aacggaagaa     480

gtggagcctg caaaagggga tcagccgata gtttctttag ccgactgaat tggctaacaa     540

aatctggaaa ctcttacccc acattgaatg tgacaatgcc taacaataaa aatttcgaca     600

aactatacat ctgggggatt catcacccga gctcaaacca acagcaaaca gaattgtaca     660

tccaagaatc aggacgagta acagtctcaa caaaaaagaag tcaacaaacg ataatcccta     720

atatcggatc tagaccgtgg gtcaggggtc aatcaggcag gataagcata tactggacca     780

ttgtaaaacc tggagatatc ctaatgataa acagtaatgg caacttagtt gcaccgcggg     840

gatattttaa attgaaaaca gggaaaagct ctgtaatgag atcagatgca cccatagaca     900

tttgtgtgtc tgaatgtatt acaccaaatg gaagcatccc caacgacaaa ccatttcaaa     960

atgtgaacaa agttacatat ggaaaatgcc ccaagtatat caggcaaaac actttaaagc    1020

tggccactgg gatgaggaat gtaccagaaa agcaaatcag aggaatcttt ggagcaatag    1080

cgggattcat agaaaacggc tgggaaggaa tggttgatgg gtggtatgga ttccgatatc    1140

aaaactcgga aggaacagga caagctgcag atctaaagag cactcaagca gccatcgacc    1200

agattaatgg aaaattaaac agagtgattg aaaggaccaa tgagaaattc catcaaatag    1260
```

-continued

```
agaaggaatt ctcagaagta gaagggagaa tccaggactt ggagaagtat gtagaagaca   1320

ccaaaataga cctatggtcc tacaatgcag aattgctggt ggctctagaa aatcaacata   1380

caattgactt aacagatgca gaaatgaata aattattcga gaagactaga cgccagttaa   1440

gagaaaacgc ggaagacatg ggaggtggat gtttcaagat ttaccacaaa tgtgataatg   1500

catgcattgg atcaataaga aatgggacat atgaccatta catatacaga gatgaagcat   1560

taaacaaccg atttcaaatc aaaggtgttg agttgaaatc aggctacaaa gattggatac   1620

tgtggatttc attcgccata tcatgcttct taatttgcgt tgttctattg ggtttcatta   1680

tgtgggcttg ccaaaaaggc aacatcagat gcaacatttg catttgagta aactgatagt   1740

taaaaacacc cttgtttcta ct                                            1762
```

<210> SEQ ID NO 20
<211> LENGTH: 1565
<212> TYPE: DNA
<213> ORGANISM: Influenza A virus

<400> SEQUENCE: 20

```
agcaaaagca gggtagataa tcactcactg agtgacatca aagtcatggc gtctcaaggc     60

accaaacgat cttatgagca gatggaaact ggtggggaac gccagaatgc aactgaaatc    120

agagcatctg ttggaaggat ggtgggagga atcggccggt tctatgttca aatgtgtact    180

gagcttaaac tcaacgacca tgaagggcgg ctgattcaga acagcataac aatagaaagg    240

atggtacttt cggcattcga cgaaagaaga aacaagtacc tcgaggagca tcccagtgct    300

gggaaagacc ccaagaaaac gggaggcccg atatacagaa ggagagatgg gaaatggatg    360

agagaactca tcctccatga taaagaagaa atcatgagga tctggcgtca ggccaacaat    420

ggtgaagacg ctactgctgg tcttactcat atgatgatct ggcactccaa tctcaatgac    480

accacctacc aaagaacaag ggctcttgtt cgggctggga tggatcccag aatgtgctct    540

ctgatgcaag gatcaactct cccacggaga tctggagctg ccggtgctgc agtgaagggt    600

gttggaacaa tggtaatgga actcatcagg atgatcaaac gcgggataaa tgatcgaaac    660

ttctggagag gtgaaaatgg tcgaagaacc agaattgctt atgaaagaat gtgcaacatc    720

ctcaagggga aattccaaac agcagcacaa cgagcaatga tggaccaagt gagggagggc    780

cgcaatcctg gaaatgctga gattgaggat ctcattttct tggcacgatc agcactcatt    840

ctgagaggat cagtagccca taaatcatgc ctacctgcct gtgtttatgg ccttgcagta    900

gccagtgggt atgactttga gaaagaggga tactctctgg ttggaattga tcctttcaaa    960

ctactccaga acagccaaat tttcagtcta atcagaccga aagaaaatcc agcacacaag   1020

agccagctgg tgtggatggc atgccattct gcagcatttg aggacctgag agtttcgaat   1080

ttcattagag gaaccaaagt aatcccaaga ggacagttag caaccagggg agtgcaaatt   1140

gcttcaaatg aaaacatgga gacaatagat tctagcacac tcgaactgag gagcagatat   1200

tgggcaataa ggaccaggag tgggggaaac accagtcaac agagagcatc tgcaggacag   1260

ataagtgtgc aacccacttt ctcagtgcag agaaatcttc cctttgaaag agcaaccatt   1320

atggctgcat tcactggaaa cactgagggg aggacttccg acatgagaac ggaaatcata   1380

aggatgatgg aaaatgccag atcagaagat gtgtctttcc aggggcgggg agtcttcgag   1440

ctctcggacg aaaaggcaac gaacccgatc gtgccttcct ttgacatgag caatgaaggg   1500

tcttatttct tcggagacaa tgctgaggag tttgacagtt aaagaaaaat acccttgttt   1560
```

-continued

```
ctact                                                               1565

<210> SEQ ID NO 21
<211> LENGTH: 1096
<212> TYPE: DNA
<213> ORGANISM: Influenza A virus

<400> SEQUENCE: 21

gtcaatcatg aagacaacca ttattttgat actactgacc cattgggtct acagtcaaaa     60

cccaaccagt ggcaacaaca cagccacatt atgtctggga caccatgcag tagcaaatgg    120

aacattggta aaaacaataa ctgatgacca aattgaggtg acaaatgcta ctgaattagt    180

tcagagcatt tcaataggga aaatatgcaa caactcatat agggttctag atggaagaaa    240

ttgcacatta atagatgcaa tgctaggaga cccccactgt gatgtctttc agtatgagaa    300

ttgggacctc ttcatagaaa gaagcagcgc tttcagcaat tgctacccat atgacatccc    360

tgactatgca tcgctccggt ccattgtagc atcctcagga acattagaat tcacagcaga    420

gggattcaca tggacaggtg tcactcaaaa cggaggaagt ggagcctgca aaaggggatc    480

agccgatagt ttctttagcc gactgaattg gctaacaaaa tctggaaact cttaccccac    540

attgaatgtg acaatgccta acaataaaaa tttcgacaaa ctatacatct gggggattca    600

tcacccgagc tcaaacaatg agcagacaaa attgtatatc caagaaacag gacgagtaac    660

agtctcaaca aaaagaagtc aacaaacaat aatccctaac atcggatcta gaccgtgggt    720

caggggtcaa tcaggcagga taagcatata ctggaccatt gtaaaacctg gagatatcct    780

aatgataaac agcaatggca acttagttgc accgcgggga tattttaaat tgagaacagg    840

gagaagctct gtaatgagat cagatgcacc catagacatt tgtgtgtctg aatgtattac    900

accaaatgga agcatcccca acgacaaacc atttcaaaat gtgaacaaag ttacatatgg    960

aaaatgcccc aaatatatca ggcaaaacac tttaaagctg gccactggga tgaggaatgt   1020

accagaaaag caaatcagag gaatctttgg agcaatagcg ggattcatag aaaacggctg   1080

ggaaggaatg gttgat                                                   1096

<210> SEQ ID NO 22
<211> LENGTH: 1061
<212> TYPE: DNA
<213> ORGANISM: Influenza A virus

<400> SEQUENCE: 22

agcaaaagca ggggatattt ctgtcaatca tgaagacaac cattattttg atactactga     60

cccattgggc ctacagtcaa aacccaatca gtggcaacaa cacagccaca ttgtgtctgg    120

gacaccatgc agtagcaaat ggaacattgg taaaaacaat aactgatgat caaattgagg    180

tgacaaatgc tactgaatta gttcagagca tttcaatggg gaaaatatgc aacaactcat    240

atagagttct agatggaaga aattgcacat taatagatgc aatgctagga gacccccact    300

gtgatgtctt tcagtatgag aattgggacc tctttataga aagaagcagc gctttcagca    360

attgctaccc atatgacatc cctgactatg catcgctccg gtccattgta gcatcctcag    420

gaacattgga attcacagca gagggattca catggacagg tgtcactcaa aacggaagaa    480

gtggagcctg caaaagggga tcagccgata gtttctttag ccgactgaat tggctaacaa    540

aatctggaaa ctcttacccc acattgaatg tgacaatgcc taacaataaa aatttcgaca    600

aactatacat ctgggggatt catcacccga gctcaaacca agagcagaca aaattgtaca    660

tccaagaatc aggacgagta acagtctcaa caaaaagaag tcaacaaaca ataatcccta    720
```

-continued

```
acatcggatc tagaccgtgg gtcaggggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgca cccatagaca    900

tttgtgtgtc tgaatgtatt acaccaaatg gaagcatctc caacgacaaa ccattccaaa    960

atgtgaacaa agttacatat ggaaaatgcc ccaagtatat caggcaaaac actttaaagc   1020
tggccactgg gatgaggaat gaaccagaaa agcaaatcag a                       1061
```

<210> SEQ ID NO 23
<211> LENGTH: 1061
<212> TYPE: DNA
<213> ORGANISM: Influenza A virus

<400> SEQUENCE: 23

```
agcaaaagca ggggatattt ctgtcaatca tgaagacaac cattattttg atactactga     60

cccattgggt ctacagtcaa aacccaacca gtggcaacaa cacagccaca ttatgtctgg    120

gacaccatgc agtagcaaat ggaacattgg taaaaacaat aactgatgac caaattgagg    180

tgacaaatgc tactgaatta gttcagagca tttcaatagg gaaaatatgc aacaactcat    240

atagagttct agatggaaga aattgcacat taatagatgc aatgctagga gacccccact    300

gtgatgtctt ccagtatgag aattgggacc tcttcataga aagaagcagc gctttcagca    360

attgctaccc atatgacatc cctgactatg catcgctccg gtccattgta gcatcctcag    420

gaacattaga attcacagca gagggattca catggacagg tgtcactcaa aacggaagaa    480

gtggagcctg caaaagggga tcagccgata gtttctttag ccgactgaat tggctaacaa    540

aatctggaaa ctcttacccc acattgaatg tgacaatgcc taacaataaa aatttcgaca    600

aactatacat ctgggggatt catcacccga gctcaaacca aaagcagaca gaattgtaca    660

tccaagaatc aggacgagta acagtctcaa caaaaagaag tcaacaaacg ataatcccta    720

atatcggatc tagaccgtgg gttaggggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgca cccatagaca    900

tttgtgtgtc tgaatgtatt acaccaaatg gaagcatccc caacgacaaa ccatttcaaa    960

atgtgaacaa agttacatat ggaaaatgcc ccaagtatat caggcaaaac actttaaagc   1020

tggccactgg gatgaggaat gtaccagaaa agcaaatcag a                       1061
```

<210> SEQ ID NO 24
<211> LENGTH: 1061
<212> TYPE: DNA
<213> ORGANISM: Influenza A virus

<400> SEQUENCE: 24

```
agcaaaagca ggggatattt ctgtcaatca tgaagacaac cattattttg atactactga     60

cccattgggt ctacagtcaa aacccaacca gtggaaacaa cacagccaca ttatgtctgg    120

gacaccatgc agtagcaaat ggaacattgg taaaaacaat aactgatgac caaattgagg    180

tgacaaatgc tactgaatta gttcagagca tttcaatagg gaaaatatgc aacaactcat    240

atagagttct agatggaaga aattgcacat taatagatgc aatgctagga gacccccact    300

gtgatgtctt ccagtatgag aattgggacc tcttcataga aagaagcagc gctttcagca    360
```

-continued

```
attgctaccc atatgacatc cctgactatg catcgctccg gtccattgta gcatcctcag    420

gaacattgga attcacagca gagggattca catggacagg tgtcactcaa aacggaagaa    480

gtggagcctg caaaagggga tcagccgata gtttctttag ccgactgaat tggctaacaa    540

aatctggaaa ctcttacccc acattgaatg tgacaatgcc taacaataaa aatttcgaca    600

aactatacat ctgggggatt catcacccga gctcaaacca aaagcagaca gaattgtaca    660

tccaagaatc aggacgagta acagtctcaa caaaaagaag tcaacaaacg ataatcccta    720

atatcggatc tagaccgtgg gtcaggggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgca cccatagaca    900

tttgtgtgtc tgaatgtatt acaccaaatg gaagcatccc caacgacaaa ccatttcaaa    960

atgtgaacaa agttacatat ggaaaatgcc ccaagtatat caggcaaaac actttaaagc   1020

tggccactgg gatgaggaat gtaccagaaa agcaaatcag a                       1061
```

<210> SEQ ID NO 25
<211> LENGTH: 1061
<212> TYPE: DNA
<213> ORGANISM: Influenza A virus

<400> SEQUENCE: 25

```
agcaaaagca ggggatattt ctgtcaatca tgaagacaac cattattttg atactactga     60

cccattgggt ctacagtcaa aacccaacca gtggaaacaa cacagccaca ttatgtctgg    120

gacaccatgc agtagcaaat ggaacattgg taaaaacaat aactgatgac caaattgagg    180

tgacaaatgc tactgaatta gttcagagca tttcaatagg gaaaatatgc aacaactcat    240

ataaagttct agatggaaga aattgcacat taatagatgc aatgctagga gacccccact    300

gtgatgtctt ccagtatgag aattgggacc tcttcataga aagaagcagc gctttcagca    360

attgctaccc atatgacatc cctgactatg catcgctccg gtccattgta gcatcctcag    420

gaacattaga attcacagca gagggattca catggacagg tgtcactcaa aacggaagaa    480

gtggagcctg caaaagggga tcagccgata gtttctttag ccgactgaat tggctaacaa    540

aatctggaaa ctcttacccc acattgaatg tgacaatgcc taacaataaa aatttcgaca    600

aactatacat ctgggggatt catcacccga gctcaaacca acagcagaca gaattgtaca    660

tccaagaatc aggacgagta acagtctcaa caaaaagaag tcaacaaacg atagtcccta    720

atatcggatc tagaccgtgg gttaggggtc aatcaggcag gataagcata tactggacca    780

ttgtaaaacc tggagatatc ctaatgataa acagtaatgg caacttagtt gcaccgcggg    840

gatattttaa attgaaaaca gggaaaagct ctgtaatgag atcagatgca cccatagaca    900

tttgtgtgtc tgaatgtatt acaccaaatg gaagcatccc caacgacaaa ccatttcaaa    960

atgtgaacaa agttacatat ggaaaatgcc ccaagtatat caggcaaaac actttaaagc   1020

tggccactgg gatgaggaat ataccagaaa agcaaatcag a                       1061
```

<210> SEQ ID NO 26
<211> LENGTH: 1763
<212> TYPE: DNA
<213> ORGANISM: Influenza A virus

<400> SEQUENCE: 26

```
agcaaaagca ggggatactt tctgtcaatc atgaagacaa ccattatttt gatactactg     60

acccattggg tctacagtca aaacccaacc agtggcaaca acacagccac actatgtctg    120
```

-continued

```
ggacaccatg cagtagcaaa tggaacattg gtaaaaacaa taactgatga ccaaattgag    180

gtgacaaatg ctactgaatt agttcagagc acttcaatag ggaaaatatg caacaaccca    240

tatagggttc tagatggaag aaactgcaca ttaatagatg caatgctagg agatccccac    300

tgtgatgttt ttcagtatga gaattgggac ctcttcatag aaagaagcag cgctttcagc    360

aattgctacc catatgacat ccctgactat gcatcgctcc ggtctattgt ggcatcttca    420

ggaacattag aattcacagc agagggattc acatggacag gtgtcactca aaacggagga    480

agtggagcct gcagaagggg gtcagccgat agtttcttta gccgactgaa ttggctaaca    540

aaatctggaa attcttaccc cacattgaat gtaacaatgc ctaacaataa caatttcgat    600

aaactataca tctgggggat ccatcacccg agcacaaaca atgagcagac aaaattgtat    660

atccaagaat cagggcgagt aacagtctca acaaaaagaa gtcaacaaac aataatcccc    720

aacatcggat ctagaccgtg ggtcaggggt caatcaggca ggataagcat atattggacc    780

attgtgaaac ctggagatat cctaatgata aacagtaatg gcaacttagt tgcaccgcgg    840

ggatatttta aaatgcgaac agggaaaagc tctgtaatga gatcagatgc acccatagac    900

acttgtgtgt ccgagtgtat tacaccaaat ggaagcatcc ccaacgacaa accatttcaa    960

aatgtgaaca aagttacata tggaaaatgc cccaagtata tcaagcagaa tactttgaag   1020

ctggccactg ggatgaggaa tgtaccagaa aagcaaatca gaggaatctt tggagcaata   1080

gcgggattca tagaaaacgg ctgggaagga atggttgatg ggtggtatgg attccgatat   1140

cagaattcgg aaggaacagg acaagctgca gatctaaaga gcactcaagc agccatcgac   1200

cagatcaatg gaaaattgaa cagagtgatt gaaaggacca atgagaaatt ccatcaaata   1260

gagaaggaat tctcagaagt agaagggaga atccaggact tggagaagta tgtagaagac   1320

accaaaatag acctatggtc ctacaatgca gagttactgg tggctctaga aaatcaacat   1380

acgattgact taacagatgc agaaatgaat aaattattcg agaagactag gcgccagtta   1440

agagaaaacg cggaagacat ggggggtgga tgtttcaaga tttatcacaa atgtgataat   1500

gcatgcattg gatcaataag aaatgggaca tatgaccatt acatatacag agatgaagca   1560

ttaaacaacc gatttcaaat taaaggtgtt gaattgaaat caggctacaa agattggata   1620

ctgtggattt cattcgccat atcatgcttc ttaatttgcg ttgttctatt gggtttcatc   1680

atgtgggctt gccaaaaagg caacatcaga tgcaacattt gcatttgagt aaactgataa   1740

ttaaaaacac ccttgtttct act                                           1763
```

<210> SEQ ID NO 27
<211> LENGTH: 1027
<212> TYPE: DNA
<213> ORGANISM: Influenza A virus

<400> SEQUENCE: 27

```
agcaaaagca ggtagatatt taaagatgag tcttctaacc gaggtcgaaa cgtacgttct     60

ctctattgta ccatcaggcc ccctcaaagc cgagatcgcg cagagacttg aagatgtctt    120

tgcagggaag aacaccgatc ttgaggcact catggaatgg ctaaagacaa gaccaatcct    180

gtcacctctg actaaaggga ttttaggatt tgtgttcacg ctcaccgtgc ccagtgagcg    240

aggactgcaa cgtagacgct ttgtccaaaa tgcccttagt ggaaacggag atccaaataa    300

catggacaga gcagtaaaac tgtacaagaa gcttaaaaga gaaataacat tccatggggc    360

aaaagaggtg gcactcagct attccactgg tgcactagcc agctgcatgg gactcatata    420
```

-continued

```
caacagaatg gggactgtga caaccgaagt ggcatttggc ctggtatgcg ccacatgtga    480

acagattgct gattcccagc atcgatctca caggcagatg gtgacaacaa ccaacccact    540

aatcagacat gaaaacagaa tggtactagc cagtaccaca gctaaaacca tggagcaggt    600

ggcagggtcg agtgagcagg cagcagaggc catggaggtt gctagtaagg ccaggcagat    660

ggtgcaggca atgaggacca ttgggaccca ccctagctcc agtgccggtt tgaaagatga    720

tcttcttgaa aatttgcagg cctaccagaa acggatggga gtgcaaatgc agcggttcaa    780

gtgatcctct cgttattgca gcaagtatca ttgggatctt gcacttgata ttgtggattc    840

ttgatcgcct tttcttcaaa ttcatttatc gtctccttaa atacggtttg aaaagagggc    900

cttctacgga aggagtacct gagtctatga gggaagaata tcggcaggaa cagcagaatg    960

ctgtggatgt tgacgatggt cattttgtca acatagagct ggagtaaaaa actaccttgt   1020

ttctact                                                             1027
```

<210> SEQ ID NO 28
<211> LENGTH: 890
<212> TYPE: DNA
<213> ORGANISM: Influenza A virus

<400> SEQUENCE: 28

```
agcaaaagca gggtgacaaa aacataatgg attccaacac tgtgtcaagc tttcaggtag     60

actgttttct ttggcatgtc cgcaaacgat ttgcagacca agaactgggt gatgccccat    120

tccttgaccg gcttcgccga gaccagaagt ccctaaaagg aagaggcagc actcttggtc    180

tggacatcga aacagccact cgtgcaggaa agcagatagt ggagcggatt ctggaagagg    240

agtcagatga ggcacttaaa atgaccattg cctctgttcc tgcttcacgc tacttaactg    300

acatgactct tgatgagatg tcaagagact ggttcatgct catgcccaag cagaaagtaa    360

caggctccct atgtataagg atggaccagg caatcatgga taagaacatc atactaaaag    420

caaactttag tgtgattttc gaaaggctgg agacactaat actacttaga gctttcaccg    480

aagaaggagc agtcgttggc gaaatttcac cattgccttc tcttccagga catactaatg    540

aggatgtcaa aaatgcaatt ggggtcctca tcggaggact taaatggaat gataacacag    600

ttagaatctc tgaaactcta cagagattcg cttggagaag cagtcatgag aatgggagac    660

cttcattccc tccaaagcag aaacgaaaaa tggcgagaac aattgagtca gaagtttgaa    720

gaaataaggt ggttgattga agaagtgcga catagattga aaaatacaga aaatagtttt    780

gaacaaataa catttatgca agccttacaa ctattgcttg aagtagaaca agagataaga    840

actttctcgt ttcagcttat ttaatgataa aaaacaccct tgtttctact              890
```

<210> SEQ ID NO 29
<211> LENGTH: 982
<212> TYPE: DNA
<213> ORGANISM: Influenza A virus

<400> SEQUENCE: 29

```
atgagtcttc tgaccgaggt cgaaacgtac gttctctcta tcgtaccatc aggccccctc     60

aaagccgaga tcgcgcagag acttgaagat gtctttgcag ggaagaacac cgatcttgag    120

gcactcatgg aatggctaaa gacaagacca atcctgtcac ctctgactaa agggatttta    180

ggattcgtat tcacgctcac cgtgcccagt gagcgaggac tgcagcgtag acgctttgtc    240

caaaatgccc ttagtggaaa cggagatcca aacaacatgg acagagcagt aaaactgtac    300

aggaaactta aaagagaaat aacattccat ggggcaaaag aggtggcact cagctattcc    360
```

-continued

```
actggtgcac tagccagctg catgggactc atatacaaca gaatgggaac tgtgacaacc    420

gaagtggcat ttggcctagt atgcgccaca tgtgaacaga ttgctgattc ccagcatcga    480

tctcacaggc agatggtgac aacaaccaac ccattaatca gacatgaaaa cagaatggta    540

ttagccagta ccacggctaa agccatggag cagatggcag ggtcgagtga gcaggcagca    600

gaggccatgg aggttgctag taaggctagg cagatggtac aggcaatgag gaccattggg    660

acccacccta gctccagtgc cggtttgaaa aatgatctcc ttgaaaattt gcaggcctac    720

cagaaacgga tgggagtgca aatgcagcga ttcaagtgat cctctcgtta ttgcagcaag    780

tatcattggg atcttgcact tgatattgtg gattcttgat cgccttttct tcaaattcat    840

ttatcgtcgc cttaaatacg ggttgaaaag agggccttct acggaaggag tacctgagtc    900

tatgagggaa gaatatcggc aggaacagca gaatgctgtg gatgttgacg atggtcattt    960

tgtcaacata gagctggagt aa                                             982
```

<210> SEQ ID NO 30
<211> LENGTH: 982
<212> TYPE: DNA
<213> ORGANISM: Influenza A virus

<400> SEQUENCE: 30

```
atgagtcttc taaccgaggt cgaaacgtac gttctctcta tcgtaccatc aggccccctc     60

aaagccgaga tcgcgcagag acttgaagat gtctttgcag ggaagaacac cgatcttgag    120

gcactcatgg aatggctaaa gacaagacca atcctgtcac ctctgactaa agggatttta    180

ggatttgtgt tcacgctcac cgtgcccagt gagcgaggac tgcagcgtag acgctttgtc    240

caaaatgccc ttagtggaaa cggagatcca aacaacatgg acagagcagt aaaactgtac    300

aggaagctta aaagagaaat aacattccat ggggcaaaag aggtggcact cagctattcc    360

actggtgcac tagccagctg catgggactc atatacaaca gaatggggac tgtgacaacc    420

gaagtggcat ttggcctggt atgcgccaca tgtgaacaga ttgctgattc ccagcatcga    480

tctcacaggc agatggtgac aacaaccaac ccactaatca gacatgaaaa cagaatggta    540

ctagccagta ccacagctaa agccatggaa cagatggcag ggtcgagtga gcaggcagca    600

gaggccatgg aggttgctag taaggccagg cagatggtac aggcaatgag gaccattggg    660

acccacccta gctccagtgc cggtttgaaa gatgatcttc ttgaaaattt gcaggcctac    720

cagaaacgga tgggagtgca aatgcagcga ttcaagtgac cctctcgtta ttgcagcaag    780

tatcattggg atcttgcact tgatattgtg gattcttgat cgccttttct tcaaattcat    840

ttatcgtcgc cttaaatacg gtttgaaaag agggccttct acggaaggag tacctgagtc    900

tatgagggaa gaatatcggc aggaacagca gaatgctgtg gatgttgacg atggtcattt    960

tgtcaacata gagctggagt aa                                             982
```

<210> SEQ ID NO 31
<211> LENGTH: 838
<212> TYPE: DNA
<213> ORGANISM: Influenza A virus

<400> SEQUENCE: 31

```
atggattcca acactgtgtc aagctttcag gtagactgtt ttctttggca tgtccgcaaa     60

cgattcgcag accaagaact gggtgatgcc ccattccttg accggcttcg ccgagaccag    120

aagtccctaa aaggaagagg tagcactctt ggtctggaca tcgaaacagc cactcgtgca    180
```

-continued

```
ggaaagcaga tagtggagca gattctggaa gaggaatcag atgaggcact taaaatgacc    240

attgcctctg ttcctgcttc acgctactta actgacatga ctcttgatga gatgtcaaga    300

gactggttca tgctcatgcc caagcagaaa gtaacaggct ccctatgtat aagaatggac    360

caggcaatca tggataagaa catcatactt aaagcaaact ttagtgtgat tttcgaaagg    420

ctggaaacac taatactact tagagccttc accgaagaag gagcagtcgt tggcgaaatt    480

tcaccattgc cttctcttcc aggacatact aatgaggatg tcaaaaatgc aattggggtc    540

ctcatcggag gacttaaatg gaatgataat acggttagaa tctctgaaac tctacagaga    600

ttcgcttgga gaagcagtca tgagaatggg agaccttcat tccctccaaa gcagaaacga    660

aaaatggaga gaacaattga gccagaagtt tgaagaaata agatggttga ttgaagaagt    720

gcgacataga ttgaaaaata cagaaaatag ttttgaacaa ataacattta tgcaagcctt    780

acaactattg cttgaagtag aacaagagat aagaactttc tcgtttcagc ttatttaa      838
```

<210> SEQ ID NO 32
<211> LENGTH: 838
<212> TYPE: DNA
<213> ORGANISM: Influenza A virus

<400> SEQUENCE: 32

```
atggattcca acactgtgtc aagctttcag gtagactgtt ttctttggca tgtccgcaaa     60

cgatttgcag accaagaact gggtgatgcc ccattccttg accggcttcg ccgagaccag    120

aagtccctaa aaggaagagg cagcactctt ggtctggaca tcgaaacagc cactcgtgca    180

ggaaagcaga tagtggagca gattctggaa gaggaatcag atgaggcact taaaatgacc    240

attgcctctg ttcctgcttc acgctactta actgacatga ctcttgatga gatgtcaaga    300

gactggttca tgctcatgcc caagcagaaa gtaacaggct ccctatgtat aaggatggac    360

caggcaatca tggataagaa catcatacta aaagcaaact ttagtgtgat tttcgaaagg    420

ctggagacac taatactact tagagccttc accgaagaag gagcagtcgt tggcgaaatt    480

tcaccattgc cttctcttcc aggacatact aatgaggatg tcaaaaatgc aattggggtc    540

ctcatcggag gacttaaatg gaatgataat acagttagag tctctgaaac tctacagaga    600

ttcgcttgga gaagcagtca tgagaatggg agaccttcat tccctccaaa gcagaaacga    660

aaaatggcga gaacaattga gccagaagtt tgaagaaata agatggttga ttgaagaagt    720

gcgacataga ttgaaaaata cagaaaatag ttttgaacaa ataacattta tgcaagcctt    780

acaactattg cttgaagtag aacaagagat aagaactttc tcgtttcagc ttatttaa      838
```

<210> SEQ ID NO 33
<211> LENGTH: 1565
<212> TYPE: DNA
<213> ORGANISM: Influenza A virus

<400> SEQUENCE: 33

```
agcaaaagca gggtagataa tcactcactg agtgacatca aagtcatggc gtctcaaggc     60

accaaacgat cttatgagca gatggaaact ggtggggaac gccagaatgc aactgaaatc    120

agagcatctg tcggaaggat ggtgggagga atcggccggt tctatgttca gatgtgtact    180

gagcttaaac tcaacgacca tgaagggcgg ctgattcaga acagcataac aatagaaagg    240

atggtacttt cggcattcga cgaaagaaga aacaagtacc tcgaggagca tcccagtgct    300

gggaaagacc ccaagaaaac gggaggcccg atatacagaa ggaaagatgg gaaatggatg    360

agagaactca tcctccatga taaagaagaa atcatgagga tctggcgtca ggccaacaat    420
```

-continued ggtgaagacg ctactgctgg tcttactcat atgatgatct ggcactccaa tctcaatgac 480
accacatacc aaagaacaag ggctcttgtt cgggctggga tggatcccag aatgtgctct 540
ctgatgcaag gatcaaccct cccacggaga tctggagctg ccggtgctgc agtaaaaggt 600
gttggaacaa tggtaatgga actcatcagg atgatcaaac gcgggataaa tgatcgaaat 660
ttctggagag gtgaaaatgg tcgaagaacc agaattgctt atgaaagaat gtgcaatatc 720
ctcaaaggga aattccaaac agcagcacaa cgggcaatga tggaccaagt gagggagggc 780
cgcaatcctg gaaatgctga gattgaggat ctcattttct tggcacgatc agcactcatt 840
ttgagaggat cagtagccca taaatcatgc ctacctgcct gtgtttatgg ccttgcagta 900
gccagtgggt atgactttga gaaggaagga tactctctgg ttggaattga tcctttcaaa 960
ctactccaga acagccaaat tttcagtcta atcagaccga aagaaaatcc agcacacaag 1020
agccagttgg tgtggatggc atgccattct gcagcatttg aggacctgag agttttgaat 1080
ttcattagag gaaccaaagt aatcccaaga ggacagttag caaccagagg agtgcaaatt 1140
gcttcaaatg aaaacatgga gacaatagat tctagcacac tcgaactgag gagcagatat 1200
tgggcaataa ggaccaggag tggagggaac accagtcaac agagagcatc tgcaggacag 1260
ataagtgtgc aacccacttt ctcagtgcag agaaatcttc cctttgaaag agcaaccatt 1320
atggctgcat tcactgggaa cactgagcgg aggacttccg acatgagaac ggaaatcata 1380
aggatgatgg aaaatgccag atcagaagat gtgtctttcc aggggcgggg agtcttcgag 1440
ctctcggacg aaaaggcaac gaacccgatc gtgccttcct ttgacatgag caatgaaggg 1500
tcttatttct tcggagacaa tgctgaggag tttgacagtt aaagaaaaat acccttgttt 1560
ctact 1565

<210> SEQ ID NO 34
<211> LENGTH: 2341
<212> TYPE: DNA
<213> ORGANISM: Influenza A virus

<400> SEQUENCE: 34
agcaaaagca ggtcaaatat attcaatatg gagagaataa aagaactgag agatctaatg 60
tcacagtccc gcacccgcga gatactaaca aaaactactg tggaccatat ggccataatc 120
aagaaataca catcaggaag acaagagaag aaccccgcac ttaggatgaa gtggatgatg 180
gcaatgaaat acccaattac agcagataag aggataatgg aaatgattcc tgagagaaat 240
gaacaggggc aaaccctttg gagcaaaacg aacgatgctg gctcagaccg cgtaatggta 300
tcacctctgg cagtgacatg gtggaatagg aatggaccaa caacgagcac aattcattat 360
ccaaaagtct acaaaactta ttttgaaaaa gttgaaaggt taaaacacgg aacctttggc 420
cccgttcatt ttaggaatca agtcaagata agacggagag ttgacgtaaa ccctggtcac 480
gcggacctca gtgccaaaga agcacaagat gtgatcatgg aagttgtttt cccaaatgaa 540
gtgggagcca gaattctaac atcggaatca caactaacaa taaccaaaga gaaaaaagaa 600
gaacttcagg actgcaaaat tgccccccttg atggtagcat acatgctaga aagagagttg 660
gtccgaaaaa caaggttcct cccagtggct ggcggaacaa gcagtgtata cattgaggtg 720
ttgcatctga ctcagggaac gtgctgggaa caaatgtaca ccccaggagg agaagttaga 780
aacgatgaca ttgatcaaag tttaattatt gctgcccgga acatagtgaa aagagcgaca 840
gtatcagcag atccactagc atccctgctg gagatgtgcc acagtacaca gattggtgga 900

-continued

```
ataaggatgg tagacatcct taagcagaat ccaacagagg aacaagctgt ggatatatgc    960
aaagcagcaa tggggttaag aattagctca tcattcagct ttggtggatt cacctttaag   1020
agaacaagtg gatcatcagt caagagagaa gaagaaatgc ttacgggcaa ccttcaaaca   1080
ttgaaaataa gagtgcatga gggctatgaa gaattcacaa tggtcggaag aagagcaaca   1140
gccattctca gaaagacaac cagaagattg attcaattga tagtaagtgg gagagatgaa   1200
cagtcaattg ctgaagcaat aattgtagcc atggtgtttt cgcaagaaga ttgcatgata   1260
aaagcagttc gaggcgattt gaacttcgtt aatagagcaa atcagcgctt gaaccccatg   1320
catcaactct tgaggcattt ccaaaaggat gcaaaagtgc ttttccagaa ttgggggatt   1380
gaacccatcg acaatgtgat gggaatgatc ggaatattgc ccgacatgac cccaagcacc   1440
gagatgtcat tgagaggagt gagagtcagc aaaatgggag tggatgagta ctccagcact   1500
gagagagtgg tggtgagcat tgaccgtttt ttaagagttc gggatcaaag gggaaacata   1560
ctactgtccc ctgaagaggt cagtgaaaca caaggaacgg aaaagctgac aataatttat   1620
tcatcatcaa tgatgtggga gattaatggt cccgagtcag tgttggtcaa tacttatcaa   1680
tggatcatca gaaactggga aattgtgaaa attcaatggt cacaggatcc cacaatgtta   1740
tacaataaga tagaatttga gccattccag tccctggtcc ctagggccac cagaagccaa   1800
tacagcggtt tcgtaaggac cctgtttcag caaatgcgag atgtacttgg aacatttgac   1860
actgctcaaa taataaaact cctccctttt gccgctgctc ctccggaaca gagtagaatg   1920
cagttctctt ctttgactgt taatgtaaga ggatcgggaa tgaggatact tgtaagaggc   1980
aattccccag tgttcaacta caacaaagcc actaagaggc tcacagtcct cggaaaggat   2040
gcaggtgcgc ttactgaaga cccagatgaa ggtacggctg gagtagaatc tgctgttctg   2100
agagggtttc tcatcttagg taaagaaaac aagagatatg gcccagcact aagcatcaat   2160
gaactgagca aacttacaaa aggggagaaa gctaatgtgc taattgggca aggggacgtg   2220
gtgttggtaa tgaaacggaa acgtgactct agcatactta ctgacagtca gacagcgacc   2280
aaaaggattc ggatggccat caattagtgt tgaattgttt aaaaacgacc ttgtttctac   2340
t                                                                   2341
```

<210> SEQ ID NO 35
<211> LENGTH: 1762
<212> TYPE: DNA
<213> ORGANISM: Influenza A virus
<220> FEATURE:
<221> NAME/KEY: modified_base
<222> LOCATION: (313)
<223> OTHER INFORMATION: a, c, g, t, unknown or other

<400> SEQUENCE: 35

```
agcaaaagca ggggatattt ctgtcaatca tgaagacaac cattgttttg atactactga     60
cccattgggt ctacagtcaa aacccaacca gtggcaacaa cacagccaca ttatgtctgg    120
gacaccatgc agtagcaaat ggaacactgg taaaaacaat aactgatgac cagattgagg    180
tgacaaatgc tactgaatta gttcagagca tttcaatagg gaaaatatgc aacaactcat    240
atagggttct agatggaaga aattgcacat taatagatgc aatgctagga gacccccact    300
gtgatgtttt tcngtatgag aattgggacc tcttcataga aagaagcagc gctttcagca    360
attgctaccc atatgacatc cctgactatg catcgctccg gtctattgtg gcatcctcag    420
gaacattaga attcacagca gagggattca catggacagg tgtcactcaa aacggaagaa    480
gtggagcctg caaaagggga tcagccgata gtttctttag ccgactgaat tggctaacaa    540
```

-continued aatctggaaa ttcttacccc acattgaatg tgacaatgcc taacaataac aatttcgata 600
aactatacat ctgggggatt catcacccga gctcaaacaa tgagcagaca aaattgtata 660
tccaagaatc aggacgagta acagtctcaa caaaaagaag tcaacaaaca ataatcccca 720
acatcggatc tagaccgtgg gtcaggggtc aatcaggcag gataagcata tattggacca 780
ttgtgaaacc tggagatatc ctaatgataa acagtaatgg caacttagtt gcaccgcggg 840
gatatttcaa attgagaaca gggaaaagct ctgtaatgag atcagatgca cccatagaca 900
cttgtgtgtc tgaatgtatt acaccaaatg gaagcatccc caacgacaaa ccattccaaa 960
atgtgaacaa agttacatat ggaaaatgcc ccaagtatat caggcaaaac actttgaagc 1020
tggccactgg gatgaggaat gtaccagaaa agcaaatcag aggaatcttt ggagcaatag 1080
cgggattcat agaaaacggc tgggaaggaa tggttgatgg gtggtatgga ttccgatatc 1140
aaaattcgga aggaacagga caagctggag atctaaagag cactcaagca gccatcgacc 1200
agatcaatgg aaaattaaac agagtgattg aaaggaccaa tgagaaattc catcaaatag 1260
agaaggaatt ctcagaagta gaagggagaa tccaggactt ggagaagtat gtagaagaca 1320
ccaaaataga cctatggtcc tacaatgcag aattgctggt ggctctagaa aatcaacata 1380
caattgactt aacagatgca gaaatgaata aattattcga gaagactagg cgccagttaa 1440
gagaaaacgc ggaagacatg ggaggtggat gtttcaggat ttaccacaaa tgtgataatg 1500
catgcattgg atcaataaga aatgggacat atgaccatta catatacaga gatgaagcat 1560
taaacaaccg atttcaaatt aaaggtgttg agttgaaatc aggctacaaa gattggatac 1620
tgtggatttc attcgccata tcatgcttct taatttgcgt tgttctattg ggtttcatta 1680
tgtgggcttg ccaaaaaggc aacatcagat gcaacatttg catttgagta aactgatagt 1740
taaaaacacc cttgtttcta ct 1762

<210> SEQ ID NO 36
<211> LENGTH: 1762
<212> TYPE: DNA
<213> ORGANISM: Influenza A virus
<220> FEATURE:
<221> NAME/KEY: modified_base
<222> LOCATION: (313)
<223> OTHER INFORMATION: a, c, g, t, unknown or other

<400> SEQUENCE: 36
agcaaaagca ggggatattt ctgtcaatca tgaagacaac cattattttg atactactga 60
cccattgggt ctacagtcaa aacccaacca gtggcaacaa cacagccaca ttatgtctgg 120
gacaccatgc agtagcaaat ggaacattgg taaaaacaat aactgatgac caaattgagg 180
tgacaaatgc tactgaatta gttcagagca tttcaatagg gaaaatatgc aacaactcat 240
atagggttct agatggaaga aattgcacat taatagatgc aatgctagga gacccccact 300
gtgatgtttt tcngtatgag aattgggacc tcttcataga aagaagcagc gcttccagca 360
attgctaccc atatgacatc cctgactatg catcgctccg gtctattgtg gcatcctcag 420
gaacattaga attcacagca gagggattca catggacagg tgtcactcaa aacggaagaa 480
gtggagcctg caaaagggga tcagccgata gtttctttag ccgactgaat tggctaacaa 540
aatctggaaa ttcttacccc acattgaatg tgacaatgcc taacaataac aatttcgata 600
agctatacat ctgggggatc catcacccga gctcaaacaa tgagcagaca aaattgtata 660
tccaagaatc aggacgagta acagtctcaa caaaaagaag tcaacaaaca ataatcccca 720

-continued

```
acatcggatc tagaccgtgg gtcaggggtc aatcaggcag gataagcata tattggacca     780

ttgtgaaacc tggagatatc ctaataataa acagtaatgg caacttagtt gcaccgcggg     840

gatatttcaa attgcgaaca gggaaaagct ctgtaatgag atcagatgca cccatagaca     900

cttgtgtgtc tgaatgtatt acaccaaatg gaagcatccc caacgacaaa ccatttcaaa     960

atgtgaacaa agttacatat ggaaaatgcc ccaagtatat caggcaaaac actttgaagc    1020

tggccactgg gatgaggaat gtaccagaaa agcaaatcag aggaatcttt ggagcaatag    1080

cgggattcat agaaaacggc tgggaaggaa tggttgatgg gtggtatgga ttccgatatc    1140

aaaactcgga aggaacagga caagctggag atctaaagag cactcaagca gccatcgacc    1200

agatcaatgg aaaattgaac agagtgattg aaaggaccaa tgagaaattc catcaaatag    1260

agaaggaatt ctcagaagta gaagggagaa tccaggactt ggagaagtat gtagaagaca    1320

ccaaaataga cctatggtcc tacaatgcag agttgctggt ggctctagaa aatcaacata    1380

caattgactt aacagatgca gaaatgaata aactattcga gaagactagg cgccagttaa    1440

gagaaaacgc ggaagacatg ggaggtggat gtttcaagat ttatcacaaa tgtgataatg    1500

catgcattgg atcaataaga aatgggacat atgaccatta catatacaga gatgaagcat    1560

taaacaaccg atttcaaatt aaaggtgtag agctgaaatc aggctacaaa gattggatac    1620

tgtggatttc attcgccata tcatgcttct taatttgcgt tgttctattg ggtttcatta    1680

tgtgggcttg ccaaaaaggc aacatcagat gcaacatttg catttgagta aactgatagt    1740

taaaaacacc cttgtttcta ct                                             1762
```

<210> SEQ ID NO 37
<211> LENGTH: 693
<212> TYPE: DNA
<213> ORGANISM: Influenza A virus

<400> SEQUENCE: 37

```
atggattcca acactgtgtc aagctttcag gtagactgtt ttctttggca tgtccgcaaa      60

cgatttgcag accaagaact gggtgatgcc ccattccttg accggcttcg ccgagaccag     120

aagtccctaa aaggaagagg tagcactctt ggtctggaca tcgaaacagc cactcgtgca     180

ggaaagcaga tagtggagca gattctggaa gaggaatcag atgaggcatt taaaatgacc     240

attgcctctg ttcctgcttc acgctactta actgacatga ctcttgatga gatgtcaaga     300

gactggttca tgctcatgcc caagcagaaa gtaacaggct ccctatgtat aagaatggac     360

caggcaatca tggataagaa catcatactt aaagcaaact ttagtgtgat tttcgaaagg     420

ctggagacac taatactact cagggccttc accgaagaag gagcagtcgt tggcgaaatt     480

tcaccattgc cttctcttcc aggacatact aatgaggatg tcaaaaatgc aattggggtc     540

ctcatcggag gacttaaatg gaatgataat acggttagag tctctgaaac tctacagaga     600

ttcgcttgga gaagcagtca tgagaatggg agaccttcat tccctccaaa gcagaaacga     660

aaaatggaga gaacaattga gtcagaagtt tga                                  693
```

<210> SEQ ID NO 38
<211> LENGTH: 1032
<212> TYPE: DNA
<213> ORGANISM: Influenza A virus

<400> SEQUENCE: 38

```
atgaagacaa ccattatttt gatactactg acccattggg tctacagtca aaacccaacc      60

agtggcaaca acacagccac attatgtctg ggacaccatg cagtagcaaa tggaacattg     120
```

-continued

```
gtaaaaacaa taactgatga ccaaattgag gtgacaaatg ctactgaatt agtccagagc    180
atttcaatag ggaaaatatg caacaactca tatagggttc tagatggaag aaattgcaca    240
ttaatagatg caatgctagg agacccccat tgtgatgatt ttcagtatga gaattgggac    300
ctcttcatag aaagaagcag cgctttcagc aattgctacc catatgacat ccctgactat    360
gcatcgctcc ggtccattgt agcatcctca ggaacattag aattcacagc agaggggttc    420
acatggacag gtgtcactca aaacggagga agtggagcct gcaaaagggg atcagccgat    480
agtttcttta gccgactgaa ttggctaaca aaatctggaa attcttaccc catattgaat    540
gtgacaatgc ctaacaataa aaatttcgat aaactataca tctgggggat tcatcacccg    600
agctcaaaca aagagcagac aaaattatat atccaagaat caggacgagt aacagtctca    660
acagaaagaa gtcaacaaac agtaatccct aacatcggat ctaggccgtg ggtcaggggt    720
caatcaggca ggataagcat atactggacc attgtaaaac ctggagatat tctaatgata    780
aacagtaatg gcaacttagt tgcaccgcgg ggatatttta aattgagaac agggaaaagc    840
tctgtaatga gatcagatgc actcatagac acttgtgtgt ctgaatgtat tacaccaaat    900
ggaagcatcc ccaacgacaa accatttcaa aatgtgaaca aaattacata tggaaaatgc    960
cccaagtata tcaggcaaaa cactttaaag ctggccactg ggatgaggaa tgtaccagaa   1020
aagcaaatca ga                                                       1032
```

<210> SEQ ID NO 39
<211> LENGTH: 1032
<212> TYPE: DNA
<213> ORGANISM: Influenza A virus

<400> SEQUENCE: 39

```
atgaagacaa ccattatttt gatactactg acccattggg tctacagtca aaacccaacc     60
agtggcaaca acacagccac attatgtctg ggacaccatg cagtagcaaa tggaacattg    120
gtaaaaacaa taactgatga ccaaattgag gtgacaaatg ctactgaatt agttcagagc    180
atttcaatag ggaaaatatg caacaactca tatagagttc tagatggaag aaattgcaca    240
ttaatagatg caatgctagg agacccccac tgtgatgtct ttcagtatga gaattgggac    300
ctcttcatag aaagaagcag cgctttcagc aattgctacc catatgacat ccctgactat    360
gcatcgctcc ggtccattgt agcatcctca ggaacattgg aattcacagc agagggattc    420
acatggacag gtgtcactca aaacggaaga agtggagcct gcaaaagggg atcagccgat    480
agtttcttta gccgactgaa ttggctaaca aaatctggaa actcttaccc cacattgaat    540
gtgacaatgc ctaacaataa aaatttcgac aaactataca tctgggggat tcatcacccg    600
agctcaaacc aacagcagac agaattgtac atccaagaat caggacgagt aacagtctca    660
acaaaaagaa gtcaacaaac gataatccct aatatcggat ctagaccatg ggtcaggggt    720
caatcaggca ggataagcat atactggacc attgtaaaac ctggagatat cctaatgata    780
aacagtaatg gcaacttagt tgcaccgcgg ggatatttta aattgaaaac agggaaaagc    840
tctgtaatga gatcagatgc acccatagac atttgtgtgt ctgaatgtat tacaccaaat    900
ggaagcatcc ccaacgacaa accatttcaa aatgtgaaca aagttacata tggaaaatgc    960
cccaagtata tcaggcaaaa cactttaaag ctggccactg ggatgaggaa tgtaccagaa   1020
aagcaaatca ga                                                       1032
```

<210> SEQ ID NO 40

-continued

<211> LENGTH: 1032
<212> TYPE: DNA
<213> ORGANISM: Influenza A virus

<400> SEQUENCE: 40
atgaagacaa ccattatttt gatactactg acccattggg tctacagtca aaacccaacc 60
agtggcaaca acacagccac attatgtctg ggacaccatg cagtagcaaa tggaacattg 120
gtaaaaacaa taactgatga ccaaattgag gtgacaaatg ctactgaatt agttcagagc 180
atttcaatag ggaaaatatg caacaactca tatagggttc tagatggaag aaattgcaca 240
ttaatagatg caatgctagg agacccccac tgtgatgttt ttcagtatga gaattgggac 300
ctcttcatag aaagaagcag cgctttcagc aattgctacc catatgacat ccctgactat 360
gcatcgctcc ggtccattgt agcatcctca ggaacattag aattcacagc agagggattc 420
acatggacag gtgtcactca aaacggaaga agtggagcct gcaaaagggg atcagccgat 480
agtttcttta gccgactgaa ttggctaaca aaatctggaa attcttaccc catattgaat 540
gtgacaatgc ctaacaataa aaatttcgat aaactataca tctgggggat tcatcacccg 600
agctcaaaca aagagcagac aaaattgtat atccaagaat caggacgagt aacagtctca 660
acagaaagaa gtcaacaaac agtaatccct aacatcggat ctagaccgtg ggtcaggggt 720
caatcaggca ggataagcat atactggacc attgtaaaac ctggagatat tctaatgata 780
aacagtaatg gcaacttagt tgcaccgcgg ggatatttta aattgagaac agggaaaagc 840
tctgtaatga gatcagatgc actcataggc acttgtgtgt ctgaatgtat tacaccaaat 900
ggaagcatcc ccaacgacaa accatttcaa aatgtgaaca aagttacata tggaaaatgc 960
cccaagtata tcaggcaaaa cactttaaag ctggccactg ggatgaggaa tgtaccagaa 1020
aagcaaatca ga 1032

<210> SEQ ID NO 41
<211> LENGTH: 1032
<212> TYPE: DNA
<213> ORGANISM: Influenza A virus

<400> SEQUENCE: 41
atgaagacaa ccattatttt gatactactg acccattggg tctacagtca aaacccaacc 60
agtggcaaca acacagccac attatgtctg ggacaccatg cagtagcaaa tggaacattg 120
gtaaaaacaa taactgatga ccaaattgag gtgacaaatg ctactgaatt agttcagagc 180
atttcaatag ggaaaatatg caacaactca tatagggttc tagatggaag aaattgcaca 240
ttaatagatg caatgctagg agacccccat tgtgatgatt ttcagtatga gaattgggac 300
ctcttcatag aaagaagcag tgctttcagc aattgctacc catatggcat ccctgactat 360
gcatcgctcc ggtccattgt agcatcctca ggaacattag aattcacagc agaggggttc 420
acatggacag gtgtcactca aaacggaaga agtggagcct gcaaaagggg atcagccgat 480
agtttcttta gccgactcaa ttggctaaca aaatctggaa attcttaccc catattgaat 540
gtgacaatgc ctaacaataa aaatttcgat aaactataca tctgggggat tcatcacccg 600
agctcaaaca aagagcagac aaaattatat atccaagaat caggacgagt aacagtctca 660
acagaaagaa gtcaacaaac agtaatccct aacatcggat ctaggccgtg ggtcaggggt 720
caatcaggca ggataagcat atactggacc attgtaaaac ctggagatat tctaatgata 780
aacaataatg gcaacttagt tgcaccgcgg ggatatttta aattgagaac agggaaaagc 840
tctgtaatga gatcagatgc actcatagac acttgtgtgt ctgaatgtat tacaccaaat 900

-continued

```
ggaagcatcc ccaacgacaa accatttcaa aatgtgaaca aagttacata tggaaaatgc    960

cccaagtata tcaggcaaaa cactttaaag ctggccactg ggatgaggaa tataccagaa   1020

aagcaaatca ga                                                       1032
```

<210> SEQ ID NO 42
<211> LENGTH: 1032
<212> TYPE: DNA
<213> ORGANISM: Influenza A virus

<400> SEQUENCE: 42

```
atgaagacaa ccattatttt gatactactg acccattggg tctacagtca aaacccaacc     60

agtggcaaca acacagccac attatgtctg ggacaccatg cagtagcaaa tggaacattg    120

gtaaaaacaa taactgatga ccaaattgag gtgacaaatg ctactgaatt agttcagagc    180

atttcaatag ggaaaatatg caacaactca tatagggttc tagatggaag aaattgcaca    240

ttaatagatg caatgctagg agacccccac tgtgatgttt ttcagtatga gaattgggac    300

ctcttcatag aaagaagcag cgctttcagc aattgctacc catatgacat ctctgactat    360

gcatcgctcc ggtccattgt agcatcctca ggaacattag aattcacagc agagggattc    420

acatggacag gtgtcactca aaacggaaga agtggagcct gcaaaagggg atcagccgat    480

agtttcttta gccgactgaa ttggctaaca aaatctggaa attcttaccc catattgaat    540

gtgacaatgc ctaacaataa aaatttcgat aaactataca tctgggggat tcatcacccg    600

agctcaaaca aagagcagac aaaattgtat atccaagaat caggacgagt aacagtctca    660

acagaaagaa gtcaacaaac agtaatccct aacatcggat ctagaccgtg ggtcaggggt    720

caatcaggca ggataagcat atactggacc attgtaaaac ctggagatat tctaatgata    780

aacagtaatg gcaacttagt tgcaccgcgg ggatatttta aattgagaac agggaaaagc    840

tctgtaatga gatcagatgc acccataggc acttgtgtgt ctgaatgtat tacaccaaat    900

ggaagcatcc ccaacgacaa accatttcaa aatgtgaaca aagttacata tggaaaatgc    960

cccaagtata tcaggcaaaa cactttaaag ctggccactg ggatgaggaa tgtaccagaa   1020

aagcaaatca ga                                                       1032
```

<210> SEQ ID NO 43
<211> LENGTH: 1032
<212> TYPE: DNA
<213> ORGANISM: Influenza A virus

<400> SEQUENCE: 43

```
atgaagacaa ccattatttt gatactactg acccattggg tctacagtca aaacccaacc     60

agtggcaaca acacagccac attatgtctg ggacaccatg cagtagcaaa tggaacattg    120

gtaaaaacaa taactgatga ccaaattgag gtgacaaatg ctactgaatt agttcagagc    180

atttcaatag ggaaaatatg caacaactca tatagagttc tagatggaag aaattgcaca    240

ttaatagatg caatgctagg agacccccac tgtgatgtct ttcagtatga gaattgggac    300

ctcttcatag aaagaagcag cgctttcagc aattgctacc catatgacat ccctgactat    360

gcatcgctcc ggtccattgt agcatcctca ggaacattag aattcacagc agagggattc    420

acatggacag gtgtcactca aaacggaaga agtggagcct gcaaaagggg atcagccgat    480

agtttcttta gccgactgaa ttggctaaca aaatctggaa attcttaccc catattgaat    540

gtgacaatgc ctaacaataa aaatttcgat aaactataca tctgggggat tcatcacccg    600
```

-continued

```
agctcaaaca aagagcagac aaaattgtac atccaagaat caggacgagt aacagtctca    660

acaaaaagaa gtcaacaaac aataatccct aacatcggat ctagaccgtg ggtcaggggt    720

caatcaggca ggataagcat atactggacc attgtaaaac ctggagatat cctaatgata    780

aacagtaatg gcaacttagt tgcaccgcgg ggatatttta aattgagaac agggaaaagc    840

tctgtaatga gatcagatgc acccatagac atttgtgtgt ctgaatgtat tacaccaaat    900

ggaagcatcc ccagcgacaa accatttcaa aatgtaaaca aagttacata tggaaaatgc    960

cccaagtata tcaggcaaaa cactttaaag ctggccactg ggatgaggaa tgtaccagaa   1020

aagcaaatca ga                                                       1032
```

<210> SEQ ID NO 44
<211> LENGTH: 1742
<212> TYPE: DNA
<213> ORGANISM: Influenza A virus

<400> SEQUENCE: 44

```
ctgtcaatca tgaagacaac cattattttg atactactga cccattgggt ctacagtcaa     60

aacccaacca gtggcaacaa cacagccaca ttatgtctgg gacaccatgc agtagcaaat    120

ggaacattgg taaaaacaat aactgatgac caaattgagg tgacaaatgc tactgaatta    180

gttcagagca tttcaatagg gaaaatatgc aacaactcat atagggttct agatggaaga    240

aattgcacat taatagatgc aatgctagga gacccccact gtgatgtttt tcagtatgag    300

aattgggacc tcttcataga aagaagcagc gctttcagca attgctaccc atatgacatc    360

cctgactatg catcgctccg gtccattgta gcatcctcag gaacattaga attcacagca    420

gagggattca catggacagg tgtcactcaa aacggaagaa gtggagcctg caaaagggga    480

tcagccgata gtttctttag ccgactgaat tggctaacaa aatctggaaa ttcttacccc    540

atattgaatg tgacaatgcc taacaataaa aatttcgata aactatacat ctgggggatt    600

catcacccga gctcaaacaa agagcagaca aaattgtata tccaagaatc aggacgagta    660

acagtctcaa cagaaagaag tcaacaaaca gtaatcccta acatcggatc tagaccgtgg    720

gtcaggggtc aatcaggcag gataagcata tactggacca ttgtaaaacc tggagatatt    780

ctaacgataa acagtaatgg caacttagtt gcaccgcggg gatattttaa attgagaaca    840

gggaaaagct ctgtaatgag atcagatgca cccatagaca cttgtgtgtc tgaatgtatt    900

acaccaaatg gaagcatccc caacgacaaa ccatttcaaa atgtgaacaa agttacatat    960

ggaaaatgcc ccaagtatat caggcaaaac actttaaagc tggccaccgg gatgaggaat   1020

gtaccagaaa agcaaatcag aggaatcttt ggagcaatag cgggattcat agaaaacggc   1080

tgggaaggaa tggttgatgg gtggtatgga ttccgatatc aaaactcgga aggaacagga   1140

caagctgcag atctaaagag cactcaagca gccatcgacc agatcaatgg aaaattaaac   1200

agagtgattg aaaggaccaa tgagaaattc catcaaatag agaaggaatt ctcagaagta   1260

gaagggagaa tccaggattt ggagaagtat gtagaagaca ccaaaataga cctatggtcc   1320

tacaatgcag aattgctggt ggctctagaa aatcaacata caattgactt aacagatgca   1380

gaaatgaata aattattcga gaagactagg cgccagttaa gagaaaacgc ggaagacatg   1440

ggaggtggat gtttcaagat ttaccacaaa tgtgataatg catgcattgg atcaataaga   1500

aatgggacat atgaccatta catatacaga gatgaagcat taaacaaccg atttcaaatc   1560

aaaggtgttg agttgaaatc aggctacaaa gattggatac tgtggatttc attcgccata   1620

tcatgcttct taatttgcgt tgttctattg ggtttcatta tgtgggcttg ccaaaaaggc   1680
```

-continued aacatcagat gcaacatttg catttgagta aactgatagt taaaaacacc cttgtttcta 1740
ct 1742

<210> SEQ ID NO 45
<211> LENGTH: 1761
<212> TYPE: DNA
<213> ORGANISM: Influenza A virus
<220> FEATURE:
<221> NAME/KEY: modified_base
<222> LOCATION: (1)..(19)
<223> OTHER INFORMATION: a, c, g, t, unknown or other
<220> FEATURE:
<221> NAME/KEY: modified_base
<222> LOCATION: (1760)..(1761)
<223> OTHER INFORMATION: a, c, g, t, unknown or other

<400> SEQUENCE: 45
nnnnnnnnnn nnnnnnnnna aatgaacact cagattctaa tattagccat ttcggcattc 60
ctctgtgtac gtgcagataa aatctgccta ggacatcatg ctgtgtctaa tggaaccaaa 120
gtagacaccc ttactgaaaa gggaatagaa gtcgtcaatg caacagaaac agttgaacaa 180
aaaaacatcc ccaagatctg ctcaaaaggg aaacagacta ttgaccttgg tcaatgtgga 240
ttactaggga ccactattgg tcccccccaa tgcgaccaat ttcttgaatt ctctgctaat 300
ttaataattg agagaagaga aggtgatgat atttgttatc caggcaaatt tgacaatgaa 360
gaaacattga gacaaatact cagaaaatcc ggaggaatta aaaaggagaa tatgggattc 420
acatataccg gagtgagaac caatggagag actagcgcct gtagaaggtc aagatcttcc 480
ttttatgcag aaatgaaatg gctcctatct aacacagaca atggggtatt cccacaaatg 540
acaaaatcct acaagaacac taagaaggag ccagctctga taatctgggg aatccaccac 600
tcaggatcaa ctgctgaaca gactagattg tatggaagtg gaaacaagtt gataacagtt 660
tggagttcca aataccaaca atcttttgcc ccaaaccctg gaccaaggcc gcaaatgaat 720
ggccaatcag gaagaattga cttttactgg ctgatgttag atcccaatga tactgttaat 780
ttcagtttta atggggcctt tatagcacct gaccgcgcca gttttctaag aggtaaatct 840
ctaggaattc agagtgacgc acaacttgac aacaattgtg aaggtgaatg ttatcatatt 900
ggaggtacca taattagcaa cttgcccttt caaaacatta atagcagagc aattgggaaa 960
tgccccagat acgtaaagca aaaaagctta atgctagcaa ccggaatgaa aaatgttcct 1020
gaaaattcta cacacaaaca gttaactcat cacatgcgca aaaaaagagg tttatttggt 1080
gcaatagcag gatttattga aaatggatgg gaaggattaa tagatggatg gtatggatac 1140
agacatcaga atgcacaagg agaaggaact gctgcagact acaaaagtac acaatctgct 1200
gtcaatcaaa taaccgggaa attaaacaga ctaatagaaa aaaccaacca gcaatttgaa 1260
ctaatagata atgaattcaa tgaaatagaa aagcaaattg gcaatgttat taactggact 1320
agagattcta tcatcgaaat atggtcatat aatgcagaat tcctcgtggc agtggagaat 1380
caacacacta ttgatttaac tgattcagag atgaacaaat tatatgaaaa ggtaagaaga 1440
cagctgagag aaaatgctga ggaagatggt aatggctgtt ttgaaatatt tcaccaatgt 1500
gacaatgatt gcatggccag cattagaaac aatacatatg atcataaaaa atacagaaag 1560
gaggcaatac aaaacagaat tcagattgat gcagtaaagt tgagcagcgg ttacaaagaa 1620
ataatacttt ggtttagctt cggggcatca tgtttcttat ttcttgccat tgcaatggtt 1680
cttgctttca tatgcataaa aaatggaaac atgcggtgca ctatttgtat ataagtttga 1740

-continued aaaaacaccc ttgtttctan n 1761

<210> SEQ ID NO 46
<211> LENGTH: 1096
<212> TYPE: DNA
<213> ORGANISM: Influenza A virus

<400> SEQUENCE: 46
agtcaaaacc caaccagtgg caacaacaca gccacattat gtctgggaca ccatgcagta 60
gcaaatggaa cattggtaaa aacaataact gatgaccaaa ttgaggtgac aaatgctact 120
gaattagttc agagcatttc aatagggaaa atatgcaaca actcatatag ggttctagat 180
ggaagaaatt gcacattaat agatgcaatg ctaggagacc cccactgtga tgtttttcag 240
tatgagaatt gggacctctt catagaaaga agcagcgctt tcagcaattg ctacccatat 300
gacatccctg actatgcatc gctccggtcc attgtagcat cctcaggaac attagaattc 360
acagcagagg gattcacatg gacaggtgtc actcaaaacg gaagaagtgg agcctgcaaa 420
aggggatcag ccgatagttt ctttagccga ctgaattggc taacaaaatc tggaaattct 480
taccccatat tgaatgtgac aatgcctaac aataaaaatt tcgataaact atacatctgg 540
gggattcatc acccgagctc aaacaaagag cagacaaaat tgtatatcca agaatcagga 600
cgagtaacag tctcaacaga aagaagtcaa caaacagtaa tccctaacat cggatctaga 660
ccgtgggtca ggggtcaatc aggcaggata agcatatact ggaccattgt aaaacctgga 720
gatattctaa tgataaacag taatggcaac ttagttgctc cgcggggata ttttaaattg 780
agaacaggga aaagctctgt aatgagatca gatgcaccca tagacacttg tgtgtctgaa 840
tgtattacac caaatggaag catccccaac gacaaaccat ttcaaaatgt gaacaaagtt 900
acatatggaa aatgccccaa gtatatcagg caaaacactt taaagctggc cactgggatg 960
aggaatgtac cagaaaagca aatcagagga atctttggag caatagaggg attcatagaa 1020
aacggctggg aaggaatggt tgatgggtgg tatggattcc gatatcaaaa ctcggaagga 1080
acaggacaag ctgcag 1096

<210> SEQ ID NO 47
<211> LENGTH: 1086
<212> TYPE: DNA
<213> ORGANISM: Influenza A virus

<400> SEQUENCE: 47
ctgtcaatca tgaagacaac cattattttg atactactga cccattgggt ctacagtcaa 60
aacccaacca gtggcaacaa cacagccaca ctatgtctgg gacaccatgc agtagcaaat 120
ggaacattgg taaaaacaat aactgatgac caaattgagg tgacaaatgc cactgaatta 180
gttcagagca cttcaatagg gaaaatatgc aacaacccat atagggttct agatggaaga 240
aactgcacat taatagatgc aatgctagga gatccccact gtgatgtttt tcagtatgag 300
aattgggacc tcttcataga aagaagcagc gctttcagca attgctaccc atatgacatc 360
cctgactatg catcgctccg gtctattgtg gcatcttcag gaacattaga attcacagca 420
gagggattca catggacagg tgtcactcaa aacggaagaa gtggcgcctg cagaagggga 480
tcagccgata gtttctttag ccgactgaat tggctaacaa aatctggaga ttcttacccc 540
acattgaatg tgacaatgcc taacaataac aatttcgata aactatacat ctgggggatc 600
catcacccga gcacaaacaa tgagcagaca aaattgtatg tccaagaatc agggcgagta 660
acagtctcaa caaaaagaag tcaacaaaca ataatcccca acatcggatc tagaccgtgg 720

-continued gtcaggggtc aaccaggcag gataagcata tattggacca ttgtgaaacc tggagatatc 780
ctaatgataa acagtaatgg caacttagtt gcaccgcggg gatatttcaa aatgcgaaca 840
ggaaaaagct ctataatgag atcagatgca cccatagaca cttgtgtgtc cgagtgtatt 900
acaccaaatg gaagcatccc caacgacaaa ccatttcaaa atgtgaacaa agttacatat 960
gggaaatgcc ccaagtatat caagcagaat actttgaagc tggccactgg gatgaggaat 1020
gtaccagaaa agcaaatcag aggaatcttt ggagcaatag cgggattcat agaaaatggc 1080
tgggag 1086

<210> SEQ ID NO 48
<211> LENGTH: 982
<212> TYPE: DNA
<213> ORGANISM: Influenza A virus

<400> SEQUENCE: 48
atgagtcttc tgaccgaggt cgaaacgtac gttctctcta tcgtaccatc aggccccctc 60
aaagccgaga tcgcgcagag acttgaagat gtctttgcag gaaagaacac cgatcttgag 120
gcactcatgg aatggctaaa gacaagacca atcctgtcac ctctgactaa ggggatttta 180
ggatttgtgt tcacgctcac cgtgcccagt gagcgaggac tgcagcgtag acgctttgtc 240
caaaatgccc ttaatgggaa cggagatcca aacaacatgg acagagcagt aaaactgtac 300
aggaagctta aaagggaaat aacattccat ggggcaaaag aggtggcact cagctattcc 360
actggtgcac tagccagctg catgggactc atatacaaca gaatggggac tgtgacaacc 420
gaagtggcat ttggcctggt atgcgccaca tgtgaacaga ttgctgattc ccagcaccga 480
tctcacagac agatggtgac aacaaccaac ccactaatca gacacgagaa cagaatggta 540
ctagccagta ccacagctaa agccatggag cagatggcag ggtcgagtga gcaggcagca 600
gaggccatgg aggttgctag tcaggccagg cagatggtgc aggcaatgag aaccattggg 660
acccacccta gctccagtgc cggtttgaaa aatgatcttc ttgaaaattt gcaggcctac 720
cagaaacgga tgggagtgca aatgcagcga ttcaagtgat cctctcgtta ttgcagcaag 780
tatcattggg atcttgcact tgatattgtg gattcttgat cgtcttttct tcaaatgcat 840
ttatcgtcgt cttaaatacg gtttgaaaag agggccttct acggaaggag tacctgagtc 900
tatgagggaa gaatatcggc aggaacagca gagtgctgtg gatgttgacg atggtcattt 960
tgtcaacata gagctggagt aa 982

<210> SEQ ID NO 49
<211> LENGTH: 982
<212> TYPE: DNA
<213> ORGANISM: Influenza A virus

<400> SEQUENCE: 49
atgagtcttc taaccgaggt cgaaacgtac gttctctcta tcgtaccatc aggccccctc 60
aaagccgaga tcgcgcagag acttgaagat gtctttgcag ggaagaacac cgatcttgag 120
gcactcatgg aatggctaaa gacaagacca atcctgtcac ctctgactaa agggatttta 180
ggatttgtgt tcacgctcac cgtgcccagt gagcgaggac tgcagcgtag acgctttgtc 240
caaaatgccc ttagtggaaa cggagatcca aacaacatgg acagagcagt aaaactgtac 300
aggaagctta aaagagaaat aacattccat ggggcaaaag aggtggcact cagctattcc 360
actggtgcac tagccagctg catgggactc atatacaaca gaatggggac tgtgacaacc 420

-continued gaagtggcat ttggcctggt atgcgccaca tgtgaacaga ttgctgattc ccagcatcga 480
tctcacaggc agatggtgac aacaaccaac ccactaatca gacatgaaaa cagaatggta 540
ctagccagta ccacagctaa agccatggag cagatggcag ggtcgagtga gcaggcagca 600
gaggccatgg aggttgctag taaggccagg cagatggtac aggcaatgag gaccattggg 660
acccacccta gctccagtgc cggtttgaaa gatgatcttc ttgaaaattt gcaggcctac 720
cagaaacgga tgggagtgca aatgcagcga ttcaagtgat cctctcgtta ttgcagcaag 780
tatcattggg atcttgcact tgatattgtg gattcttgat cgcctttttct tcaaattcat 840 ttatcgtcgc cttaaatacg gtttgaaaag agggccttct acggaaggag tacctgagtc 900
tatgagggaa gaatatcggc aggaacagca gaatgctgtg gatgttgacg atggtcattt 960
tgtcaacata gagctggagt aa 982

<210> SEQ ID NO 50
<211> LENGTH: 838
<212> TYPE: DNA
<213> ORGANISM: Influenza A virus

<400> SEQUENCE: 50
atggattcca acactgtgtc aagctttcag gtagactgtt ttctttggca tgtccgcaaa 60
cgatttgcag accaagaact gggtgatgcc ccattccttg accggcttcg ccgagaccag 120
aagtccctaa aaggaagagg cagcactctt ggtctggaca tcgaaacagc cactcatgca 180
ggaaagcaga tagtggagcg aattctggaa gaggaatcag atgaggcact taaaatgacc 240
atagcctctg ttcctacttc acgctactta actgacatga ctcttgatga gatgtcaaga 300
gactggttca tgctcatgcc caagcagaaa gtaacaggct ccctatgtat aaggatggac 360
caagcaatca tggataagaa catcatacta aaagcaaact ttagtgtgat tttcgaaagg 420
ctggagacac taatactact tagagctttc accgaagaag gagcagtcgt tggcgaaatt 480
tcaccattgc cttctcttcc aggacatact aatgaggatg tcaaaaatgc aattggggtc 540
ctcatcggag gacttaaatg gaatgataac acagttagag tctctgaaac tctacagaga 600
ttcgcttgga gaagcagtca tgagaatggg agaccttcat tccctccaaa gcagaaacga 660
aaaatggcga gaacaattga gtcagaagtt tgaagaaata aggtggttga ttgaagaagt 720
gagacataga ttgaaaaata cagaaaatag ttttgaacaa ataacattta tgcaagcctt 780
acaactattg cttgaagtag aacaagagat aagaactttc tcgtttcagc ttatttaa 838

<210> SEQ ID NO 51
<211> LENGTH: 838
<212> TYPE: DNA
<213> ORGANISM: Influenza A virus

<400> SEQUENCE: 51
atggattcca acactgtgtc aagctttcag gtagactgtt ttctttggca tgtccgcaaa 60
cgatttgcag accaagaact gggtgatgcc ccattccttg accggcttcg ccgagaccag 120
aagtccctaa aaggaagagg cagcactctt ggtctggaca tcgaaacagc cactcgtgca 180
ggaaagcaga tagtggagcg gattctggaa gaggagtcag atgaggcact taaaatgacc 240
attgcctctg ttcctgcttc acgctactta actgacatga ctcttgatga gatgtcaaga 300
gactggttca tgctcatgcc caagcagaaa gtaacaggct ccctatgtat aaggatggac 360
caggcaatca tggataagaa catcatacta aaagcaaact ttagtgtgat tttcgaaagg 420
ctggagacac taatactact tagagccttc accgaagaag gagcagtcgt tggcgaaatt 480

-continued

```
tcaccattgc cttctcttcc aggacatact aatgaggatg tcaaaaatgc aattggggtc    540

ctcatcggag gacttaaatg gaatgataat acagttagag tctctgaaac tctacagaga    600

ttcgcttgga gaagcagtca tgagaatggg agaccttcat tccctccaaa gcagaaacga    660

aaaatggcga gaacaattga gccagaagtt tgaagaaata agatggttga ttgaagaagt    720

gcgacataga ttgaaaaata cagaaaatag ttttgaacaa ataacattta tgcaagcctt    780

acaactattg cttgaagtag aacaagagat aagaactttc tcgtttcagc ttatttaa      838
```